(12) United States Patent
Beau-Larvor et al.

(10) Patent No.: US 9,624,308 B2
(45) Date of Patent: Apr. 18, 2017

(54) ANTIGEN BINDING PROTEINS

(71) Applicant: PIERRE FABRE MEDICAMENT, Boulogne-Billancourt (FR)

(72) Inventors: Charlotte Beau-Larvor, Jonzier Epagny (FR); Liliane Goetsch, Ayze (FR); Nicolas Boute, Cernex (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 14/440,491

(22) PCT Filed: Nov. 5, 2013

(86) PCT No.: PCT/EP2013/073036
§ 371 (c)(1),
(2) Date: May 4, 2015

(87) PCT Pub. No.: WO2014/068139
PCT Pub. Date: May 8, 2014

(65) Prior Publication Data
US 2016/0046725 A1 Feb. 18, 2016

(30) Foreign Application Priority Data

Nov. 5, 2012 (EP) ..................... 12290383

(51) Int. Cl.
C07K 16/28 (2006.01)
C07K 16/40 (2006.01)
A61K 47/48 (2006.01)
C07K 16/30 (2006.01)

(52) U.S. Cl.
CPC ........ C07K 16/40 (2013.01); A61K 47/48469 (2013.01); A61K 47/48561 (2013.01); C07K 16/2863 (2013.01); C07K 16/30 (2013.01); *C07K 2317/33* (2013.01); *C07K 2317/565* (2013.01); *C07K 2317/73* (2013.01); *C07K 2317/76* (2013.01); *C07K 2317/77* (2013.01)

(58) Field of Classification Search
CPC .......................... C07K 16/00–16/468
See application file for complete search history.

(56) References Cited

U.S. PATENT DOCUMENTS

| | | |
|---|---|---|
| 4,970,198 A | 11/1990 | Lee et al. |
| 5,079,233 A | 1/1992 | Lee |
| 5,246,019 A | 9/1993 | Godfrey et al. |
| 5,530,101 A | 6/1996 | Queen et al. |
| 5,585,089 A | 12/1996 | Queen et al. |
| 5,606,040 A | 2/1997 | McGahren et al. |
| 5,639,641 A | 6/1997 | Pedersen et al. |
| 5,693,761 A | 12/1997 | Queen et al. |
| 5,693,762 A | 12/1997 | Queen et al. |
| 5,739,116 A | 4/1998 | Hamann et al. |
| 5,767,285 A | 6/1998 | Hamann et al. |
| 5,773,001 A | 6/1998 | Hamann et al. |
| 5,877,293 A | 3/1999 | Adair et al. |
| 5,886,152 A | 3/1999 | Nakatani et al. |
| 6,054,297 A | 4/2000 | Carter et al. |
| 6,180,370 B1 | 1/2001 | Queen et al. |
| 9,173,962 B2 * | 11/2015 | Beau-Larvor .......... C07K 14/71 |

FOREIGN PATENT DOCUMENTS

| | | |
|---|---|---|
| EP | 0682040 A1 | 11/1995 |
| EP | 0939127 A2 | 9/1999 |
| WO | WO 91/06279 A2 | 5/1991 |
| WO | WO 92/11018 A1 | 7/1992 |
| WO | WO 2008/047242 A1 | 4/2008 |
| WO | WO 2011/014457 A1 | 2/2011 |
| WO | WO 2011/1599801 A1 | 12/2011 |

OTHER PUBLICATIONS

Alley et al., "The Pharmacologic Basis for Antibody-Auristatin Conjugate Activity," The Journal of Pharmacology and Experimental Therapeutics, vol. 330, No. 3, 2009, pp. 932-938.

Bebbington et al., "High-Level Expression of a Recombinant Antibody From Myeloma Cells Using a Glutamine Synthetase Gene as an Amplifiable Selectable Marker," Bio/Technology, vol. 10, No. 2, Feb. 1992, pp. 169-175.

Beck et al., "The Next Generation of Antibody-drug Conjugates Comes of Age," Discovery Medicine, vol. 10, No. 53, Oct. 16, 2010, pp. 329-339 (13 pages).

Fraker et al., "Protein and Cell Membrane Iodinations with a Sparingly Soluble Chloroamide, 1,3,4,6-Tetrachloro-3a,6a-Diphenylglycoluril," Biochemical and Biophysical Research Communications, vol. 80, No. 4, Feb. 28, 1978, pp. 849-857.

Hafizi et al., "Gas6 and protein S Vitamin K-dependent ligands for the Axl receptor tyrosine kinase subfamily," The FEBS Journal, vol. 273, 2006, pp. 5231-5244.

Harlow et al., "Proteolytic Fragments of Antibodies," Antibodies A Laboratory Manual, Chapter 15, 1988, pp. 626-627.

Holland et al., "Multiple Roles for the Receptor Tyrosine Kinase Axl in Tumor Formation," Cancer Research, vol. 65, No. 20, Oct. 15, 2005, pp. 9294-9303.

Hong et al., "Receptor tyrosine kinase AXL is induced by chemotherapy drugs and overexpression of AXL confers drug resistance in acute myeloid leukemia," Cancer Letters, vol. 268, 2008 (published online May 27, 2008), pp. 314-324.

(Continued)

*Primary Examiner* — Jessica H Roark
(74) *Attorney, Agent, or Firm* — Birch, Stewart, Kolasch & Birch, LLP

(57) ABSTRACT

The present invention relates to novel antigen binding proteins, in particular monoclonal antibodies, capable of binding to the protein Axl as well as the amino and nucleic acid sequences coding for said proteins. From one aspect, the invention relates to novel antigen binding proteins, or antigen binding fragments, capable of binding to Axl and, by inducing internalization of Axl, being internalized into the cell. The invention also comprises the use of said antigen binding proteins as addressing products in conjugation with other anti-cancer compounds, such as toxins, radio-elements or drugs, and the use of same for the treatment of certain cancers.

14 Claims, 34 Drawing Sheets

(56) References Cited

OTHER PUBLICATIONS

Figure 1A:
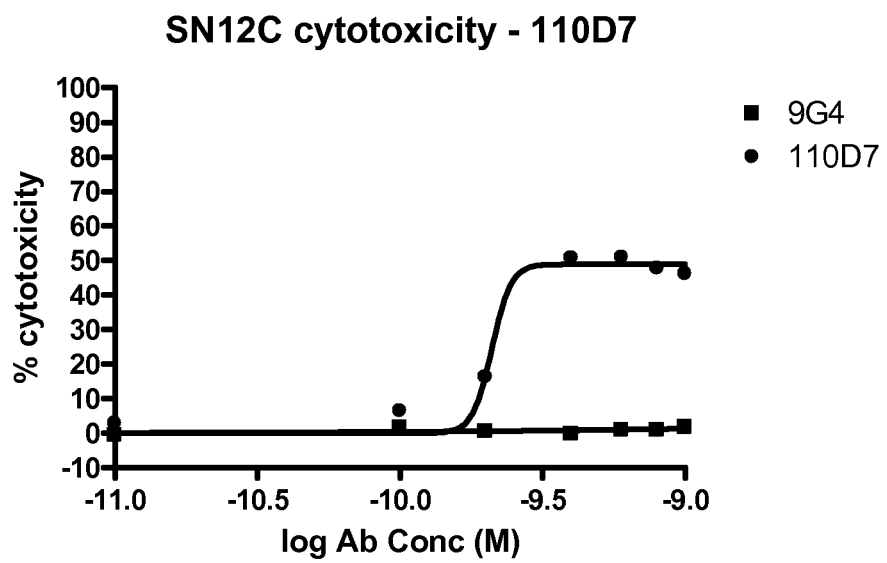

Jones et al., "Replacing the complementarity-determining regions in a human antibody with those from a mouse," Nature, vol. 321, May 29, 1986, pp. 522-525.
Kaas et al., "IMGT Colliers de Perles: Standardized Sequence-Structure Representations of the IgSF and MhcSF Superfamily Domains," Current Bioinformatics, vol. 2, No. 1, 2007, pp. 21-30.
Kaas et al., "IMGT/3Dstructure-DB and IMGT/StructuralQuery, a database and a tool for immunoglobulin, T cell receptor and MHC structural data," Nucleic Acids Research, Database issue, vol. 32, 2004, pp. D208-D210.
Kabat et al., "Sequences of Proteins of Immunological Interest," Fifth Edition, vol. 1, 1991, 12 pages, e-book.
Keating et al., "Inhibition of Mer and Axl Receptor Tyrosine Kinases in Astrocytoma Cells Leads to Increased Apoptosis and Improved Chemosensitivity," Molecular Cancer Therapeutics, vol. 9, No. 5, May 2010 (Published Online first Apr. 27, 2010), pp. 1298-1307.
Köhler et al., "Continuous cultures of fused cells secreting antibody of predefined specificity," Nature, vol. 256, Aug. 7, 1975, pp. 495-497.
Korshunov et al., "Axl Mediates Vascular Remodeling Induced by Deoxycorticosterone Acetate-Salt Hypertension," Hypertension, vol. 50, Dec. 2007 (originally published online Oct. 8, 2007), pp. 1057-1062.
Korshunov et al., "Axl, A Receptor Tyrosine Kinase, Mediates Flow-Induced Vascular Remodeling," Circulation Research, vol. 98, Jun. 9, 2006 (originally published online Apr. 20, 2006), pp. 1446-1452.
Lay et al., "Sulfasalazine Suppresses Drug Resistance and Invasiveness of Lung Adenocarcinoma Cells Expressing AXL," Cancer Research, vol. 67, No. 8, Apr. 15, 2007, pp. 3878-3887.
Ledford, "Toxic antibodies blitz tumours," Nature, vol. 476, Aug. 25, 2011, pp. 380-381.
Lefranc et al., "IMGT unique numbering for immunoglobulin and T cell receptor variable domains and Ig superfamily V-like domains," Developmental and Comparative Immunology, vol. 27, 2003, pp. 55-77.
Lefranc, "The IMGT Unique Numbering for Immunoglobulins, T-Cell Receptors, and Ig-Like Domains," The Immunologist, vol. 7, No. 4, 1999, pp. 132-136.
Lefranc, "Unique database numbering system for immunogenetic analysis," Immunology Today, vol. 18, No. 11, Nov. 1997, p. 509.
Lemke et al., "Immunobiology of the TAM receptors," Nature Reviews Immunology, vol. 8, No. 5, May 2008, pp. 327-336.
Lewis Phillips et al., "Targeting HER2-Positive Breast Cancer with Trastuzumab-DM1, an Antibody-Cytotoxic Drug Conjugate," Cancer Research, vol. 68, No. 22, Nov. 15, 2008, pp. 9280-9290.
Li et al., "Axl as a potential therapeutic target in cancer: role of Axl in tumor growth, metastasis and angiogenesis," Oncogene, vol. 28, 2009 (published online Jul. 27, 2009), pp. 3442-3455, XP-002601155.
Linger et al., "TAM Receptor Tyrosine Kinases: Biologic Functions, Signaling, and Potential Therapeutic Targeting in Human Cancer," Advance Cancer Research, vol. 100, 2008, pp. 35-83 (41 pages).
Liu et al., "Novel Mechanism of Lapatinib Resistance in HER2-Positive Breast Tumor Cells: Activation of AXL," Cancer Research, vol. 69, No. 17, Sep. 1, 2009 (Published Online first Aug. 11, 2009), pp. 6871-6878.
Macleod et al., "Altered ErbB Receptor Signaling and Gene Expression in Cisplatin-Resistant Ovarian Cancer," Cancer Research, vol. 65, No. 15, Aug. 1, 2005, pp. 6789-6800.
Mahadevan et al., "A novel tyrosine kinase switch is a mechanism of imatinib resistance in gastrointestinal stromal tumors," Oncogene, vol. 26, 2007 (Published online Feb. 26, 2007), pp. 3909-3919.

Manfioletti et al., "The Protein Encoded by a Growth Arrest-Specific Gene (gas6) Is a New Member of the Vitamin K-Dependent Proteins Related to Protein S, a Negative Coregulator in the Blood Coagulation Cascade," Molecular and Cellular Biology, vol. 13, No. 8, Aug. 1993, pp. 4976-4985.
Maxfield et al., "Endocytic Recycling," Nature Reviews, Molecular Cell Biology, vol. 5, Feb. 2004, pp. 121-132.
Mountain et al., "Engineering Antibodies for Therapy," Biotechnology and Genetic Engineering Reviews, vol. 10, Dec. 1992, pp. 1-142.
Nagata et al., "Identification of the Product of Growth Arrest-specific Gene 6 as a Common Ligand for Axl, Sky, and Mer Receptor Tyrosine Kinases," The Journal of Biological Chemistry, vol. 271, No. 47, Nov. 22, 1996, pp. 30022-30027.
Needleman et al., "A General Method Applicable to the Search for Similarities in the Amino Acid Sequence of Two Proteins," Journal of Molecular Biology, vol. 48, 1970, pp. 443-453.
Pearson et al., "Improved tools for biological sequence comparison," Proceedings of the National Adademy of Sciences, vol. 85, Apr. 1988, pp. 2444-2448.
Riechmann et al., "Reshaping human antibodies for therapy," Nature, vol. 332, Mar. 24, 1988, pp. 323-327.
Ruiz et al., "IMGT gene identification and Colliers de Perles of human immunoglobulins with known 3D structures," Immunogenetics, vol. 53, No. 10-11, 2002 (published online Jan. 30, 2002), pp. 857-883.
Singer et al., "Optimal Humanization of 1B4, an Anti-CD18 Murine Monoclonal Antibody, Is Achieved by Correct Choice of Human V-Region Framework Sequences," The Journal of Immunology, vol. 150, No. 7, Apr. 1, 1993, pp. 2844-2857.
Smith et al., "Comparison of Biosequences," Advances in Applied Mathematics, vol. 2, 1981, pp. 482-489.
Tatusova et al., "Blast 2 Sequences, a new tool for comparing protein and nucleotide sequences," FEMS Microbiology Letters, vol. 174, 1999, pp. 247-250.
Thiery, "Epithelial-mesenchymal transitions in development and pathologies," Current Opinion in Cell Biology, vol. 15, 2003, pp. 740-746.
Varnum et al., "Axl receptor tyrosine kinase stimulated by the vitamin K-dependent protein encoded by growth-arrest-specific gene 6," Nature, vol. 373, Feb. 16, 1995, pp. 623-626.
Verhoeyen et al., "Engineering of Antibodies," BioEssays, vol. 8, No. 2, Feb./Mar. 1988, pp. 74-78.
Verhoeyen et al., "Reshaping Human Antibodies: Grafting an Antilysozyme Activity," Science, vol. 239, Mar. 25, 1988, pp. 1534-1536.
Verma et al., "Targeting Axl and Mer Kinases in Cancer," Molecular Cancer Therapeutics, vol. 10, No. 10, Oct. 2011 (Published Online first Sep. 20, 2011), pp. 1763-1773.
Wiseman et al., "Ibritumomab tiuxetan radioimmunotherapy for patients with relapsed or refractory non-Hodgkin lymphoma and mild thrombocytopenia: a phase II multicenter trial," Blood, vol. 99, No. 12, Jun. 15, 2002, pp. 4336-4342.
Wiseman et al., "Phase I/II $^{90}$ Y-Zevalin (yttrium-90 ibritumomab tiuxetan, IDEC-Y2B8) radioimmunotherapy dosimetry results in relapsed or refractory non-Hodgkin's lymphoma," European Journal of Nuclear Medicine, vol. 27, No. 7, Jul. 2000, pp. 766-777.
Witzig et al., "Randomized Controlled Trial of Yttrium-90-Labeled Ibritumomab Tiuxetan Radioimmunotherapy Versus Rituximab Immunotherapy for Patients with Relapsed or Refractory Low-Grade, Follicular . . . ," Journal of Clinical Oncology, vol. 20, No. 10, May 15, 2002, pp. 2453-2463.
Witzig et al., "Treatment With Ibritumomab Tiuxetan Radioimmunotherapy in Patients With Rituximab-Refractory Follicular Non-Hodgkin's Lymphoma," Journal of Clinical Oncology, vol. 20, No. 15, Aug. 1, 2002, pp. 3262-3269.
Ye et al., "An anti-Axl monoclonal antibody attenuates xenograft tumor growth and enhances the effect of multiple anticancer therapies," Oncogene, vol. 29, 2010 (published online Jul. 5, 2010), pp. 5254-5264, XP-002671996.
International Search Report issued in PCT/EP2013/073036, mailed on Feb. 20, 2014.

\* cited by examiner

|  | 1003A2 |
|---|---|
| Sigmoidal dose-response (variable slope) | |
| Best-fit values | |
|   BOTTOM | 0.0770 |
|   TOP | 2.842 |
|   LOGEC50 | -8.630 |
|   HILLSLOPE | 1.410 |
|   EC50 | 2.345e-009 |

| | Calu-1 | MCF7 | MDAMB231 | MDAMB435S | NCI-H125 | Panc1 | SN12C |
|---|---|---|---|---|---|---|---|
| Sigmoidal dose-response (variable slope) | | | | | | | |
| Best-fit values | | | | | | | |
| BOTTOM | 12.00 | 12.00 | 12.00 | 12.00 | 12.00 | 12.00 | 12.00 |
| TOP | 878.3 | 4.591 | 334.4 | 76.16 | 31.72 | 285.9 | 1100 |
| LOGEC50 | -9.562 | -4.487 | -9.993 | -10.27 | -10.20 | -9.936 | -9.898 |
| HILLSLOPE | 1.365 | -0.1147 | 1.894 | 7.115 | 23.90 | 1.082 | 1.811 |
| EC50 | 2.742e-010 | 3.257e-005 | 1.017e-010 | 5.368e-011 | 6.324e-011 | 1.158e-010 | 1.266e-010 |
| | Calu-1 | MCF7 | MDAMB231 | MDAMB435S | NCI-H125 | Panc1 | SN12C |
| $R^2$ | 0.9841 | 0.3716 | 0.9785 | 0.9338 | 0.8622 | 0.9867 | 0.9863 |

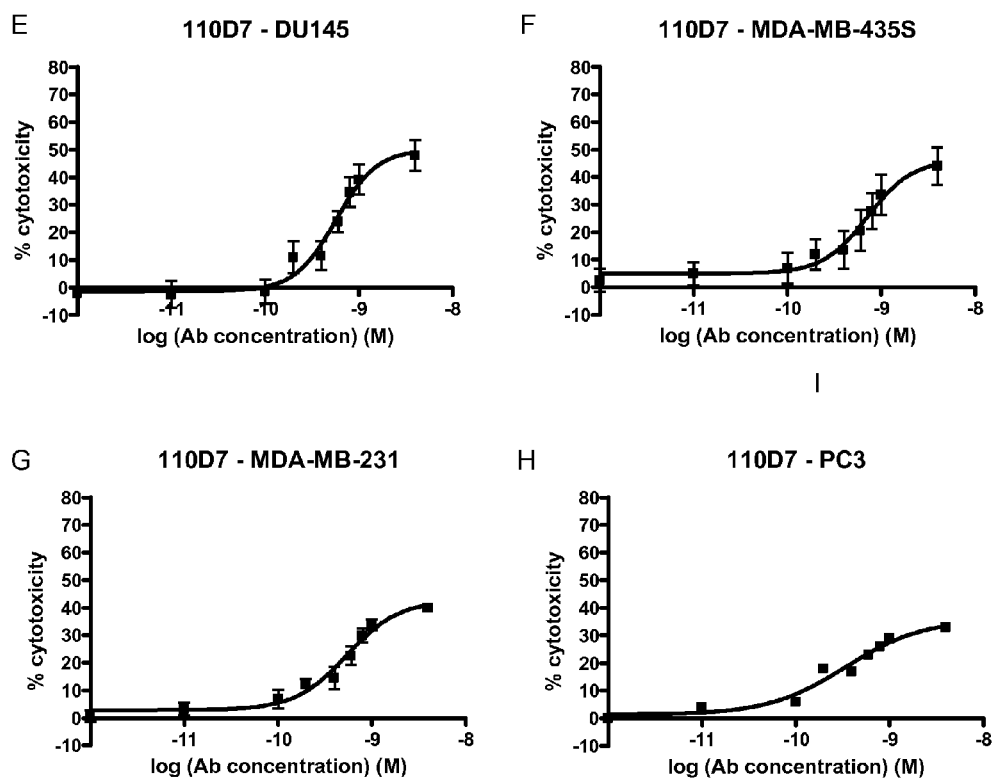
FIGURES 11A-11K (suite)

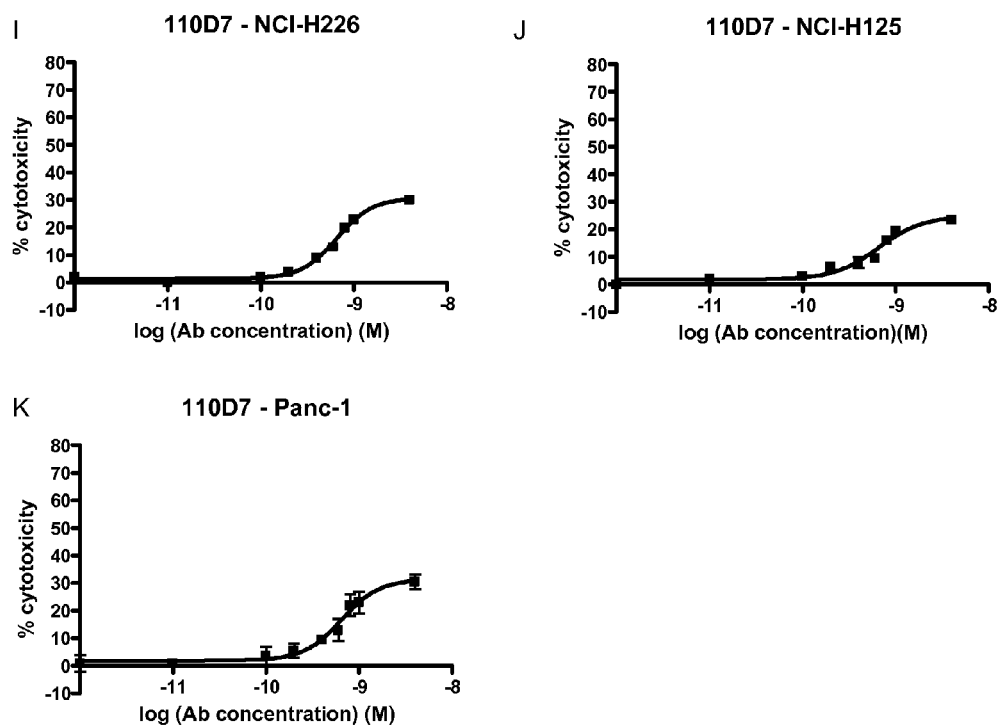
FIGURES 11A-11K (suite)

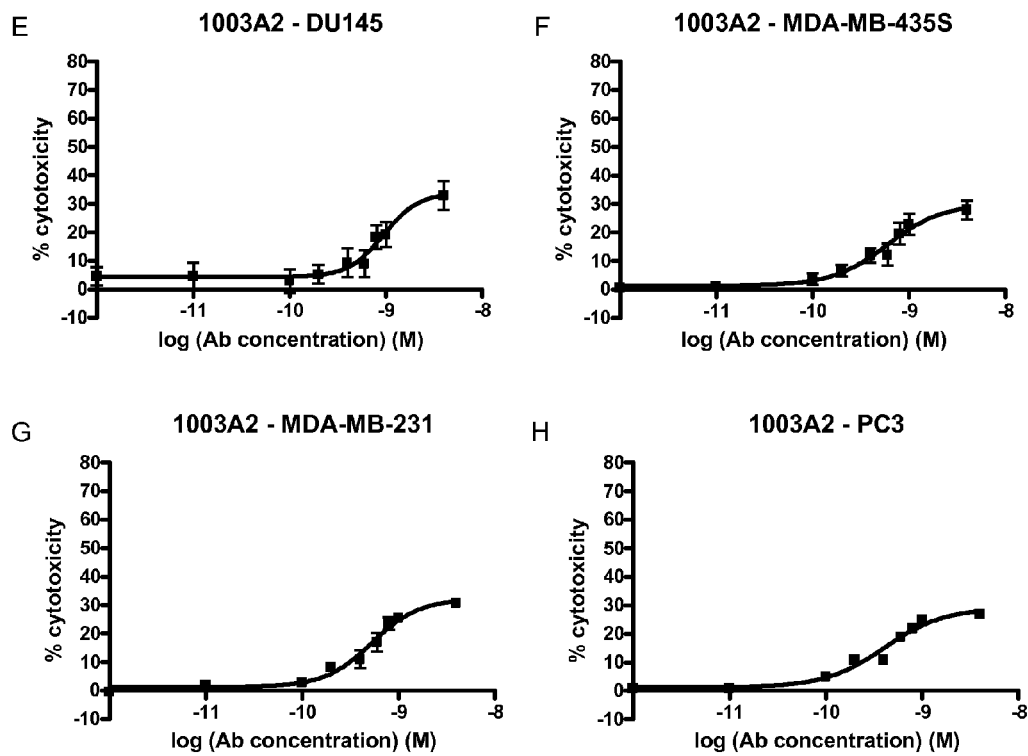
FIGURES 12A-12K (suite)

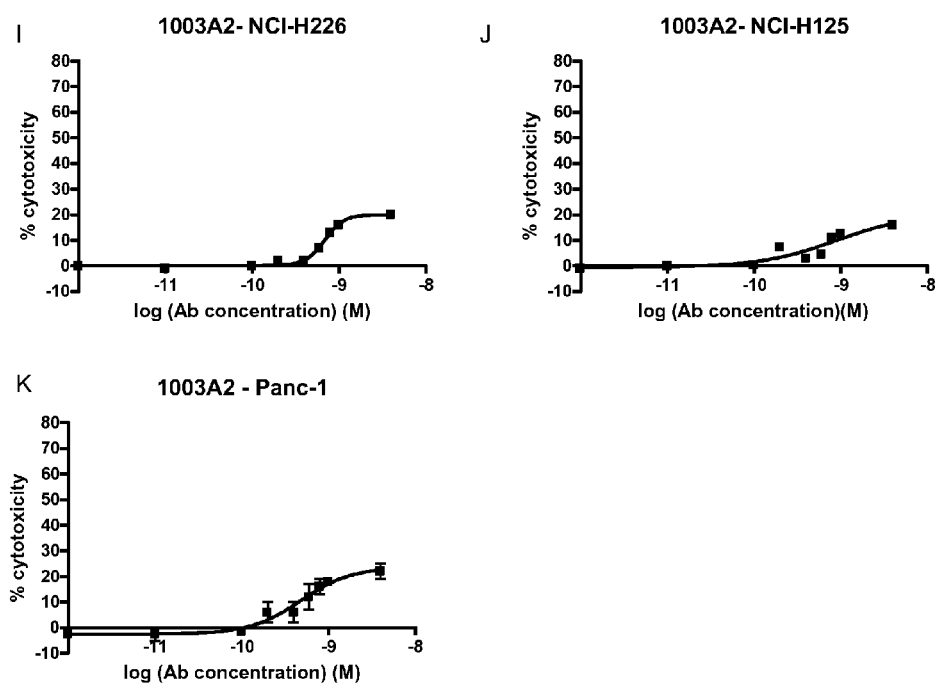
FIGURES 12A-12K (suite)

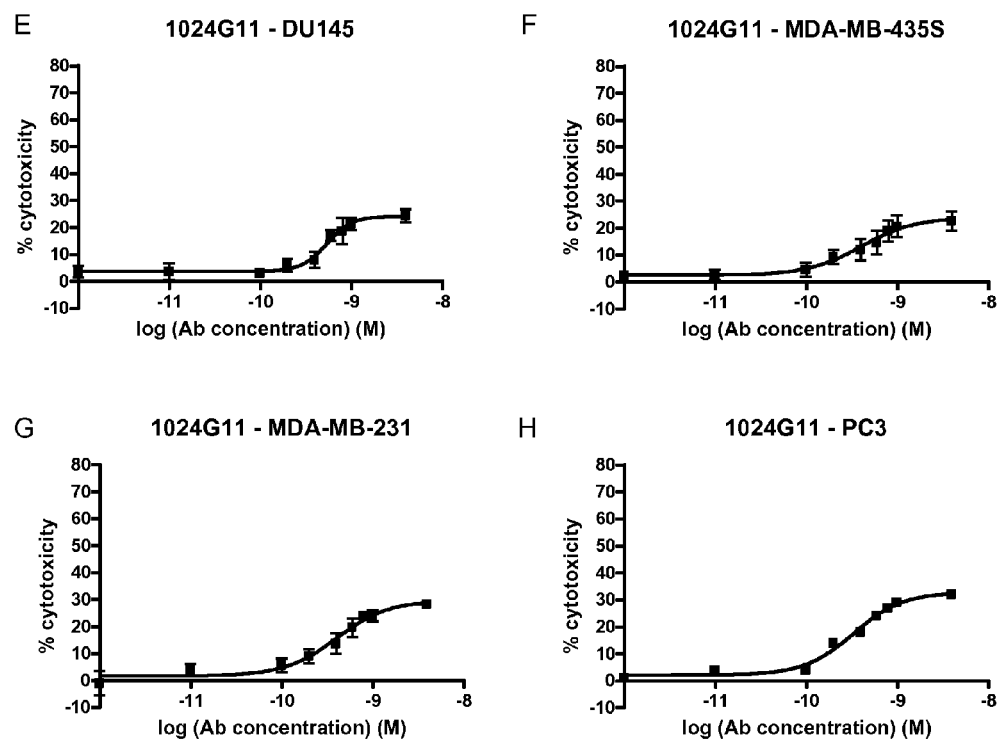
FIGURES 13A-13K (suite)

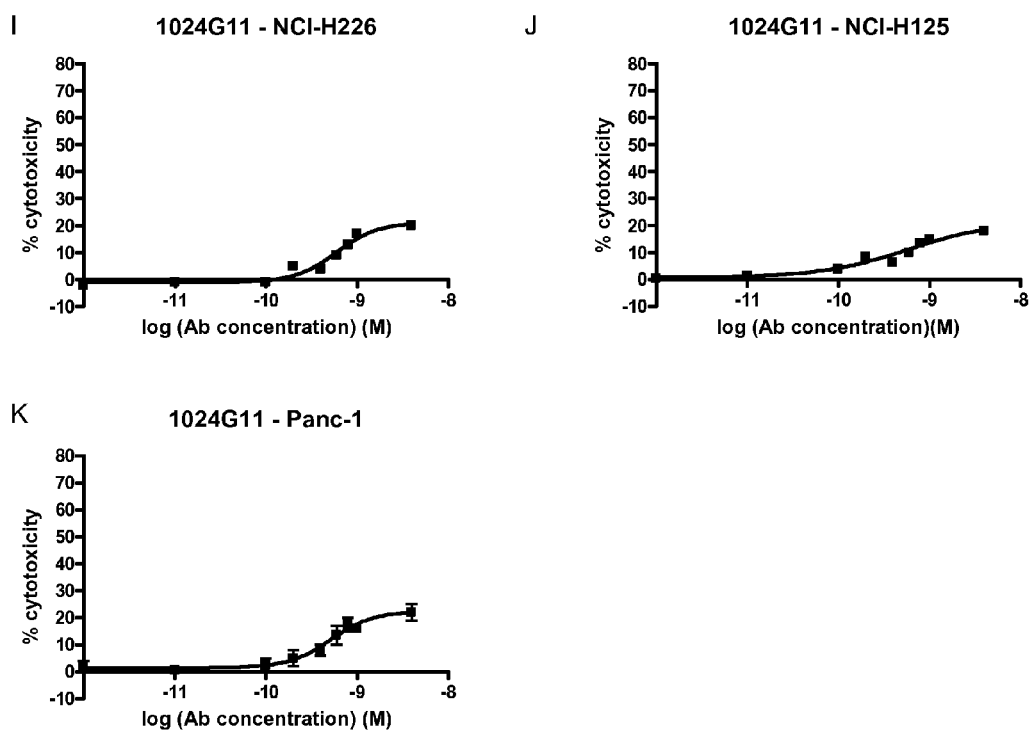
FIGURES 13A-13K (suite)

SEQUENCE LISTING

<160> NUMBER OF SEQ ID NOS: 91

<210> SEQ ID NO 1
<211> LENGTH: 6
<212> TYPE: PRT
<213> ORGANISM: artificial
<220> FEATURE:
<223> OTHER INFORMATION: Light Chain CDR-L1 from 110D7 antibody (IMGT
      numbering)

<400> SEQUENCE: 1

Gln Asp Val Thr Thr Ala
1               5

<210> SEQ ID NO 2
<211> LENGTH: 3
<212> TYPE: PRT
<213> ORGANISM: artificial
<220> FEATURE:
<223> OTHER INFORMATION: Light Chain CDR-L2 from 110D7 antibody (IMGT
      numbering)

<400> SEQUENCE: 2

Trp Ala Ser
1

<210> SEQ ID NO 3
<211> LENGTH: 9
<212> TYPE: PRT
<213> ORGANISM: artificial
<220> FEATURE:
<223> OTHER INFORMATION: Light Chain CDR-L3 from 110D7 antibody (IMGT
      numbering)

<400> SEQUENCE: 3

Gln Gln His Tyr Arg Ile Pro Phe Thr
1               5

<210> SEQ ID NO 4
<211> LENGTH: 8
<212> TYPE: PRT
<213> ORGANISM: artificial
<220> FEATURE:
<223> OTHER INFORMATION: Heavy Chain CDR-H1 from 110D7 antibody (IMGT
      numbering)

<400> SEQUENCE: 4

Gly Phe Thr Phe Ser Asp Tyr Tyr
1               5

<210> SEQ ID NO 5
<211> LENGTH: 8
<212> TYPE: PRT
<213> ORGANISM: artificial
<220> FEATURE:
<223> OTHER INFORMATION: Heavy Chain CDR-H2 from 110D7 antibody (IMGT
      numbering)

<400> SEQUENCE: 5

Ile Ser Asn Gly Gly Gly Ser Thr
1               5

<210> SEQ ID NO 6
<211> LENGTH: 10
<212> TYPE: PRT
<213> ORGANISM: artificial

```
<220> FEATURE:
<223> OTHER INFORMATION: Heavy Chain CDR-H3 from 110D7 antibody (IMGT
      numbering)

<400> SEQUENCE: 6

Ala Arg Leu Ser Phe Tyr Ala Met Asp Tyr
1               5                   10

<210> SEQ ID NO 7
<211> LENGTH: 107
<212> TYPE: PRT
<213> ORGANISM: artificial
<220> FEATURE:
<223> OTHER INFORMATION: Light chain variable domain

<400> SEQUENCE: 7

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Thr Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Arg Ile Pro Phe
                85                  90                  95

Thr Phe Gly Ser Gly Thr Lys Leu Glu Ile Lys
            100                 105

<210> SEQ ID NO 8
<211> LENGTH: 117
<212> TYPE: PRT
<213> ORGANISM: artificial
<220> FEATURE:
<223> OTHER INFORMATION: Heavy chain variable domain

<400> SEQUENCE: 8

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Gly Gly Gly Ser Thr Tyr Tyr Pro Asp Thr Val
    50                  55                  60

Lys Gly Arg Phe Thr Met Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Leu Ser Phe Tyr Ala Met Asp Tyr Trp Gly Gln Gly Thr Ser
            100                 105                 110

Val Thr Val Ser Ser
        115

<210> SEQ ID NO 9
<211> LENGTH: 11
<212> TYPE: PRT
<213> ORGANISM: artificial
```

```
<220> FEATURE:
<223> OTHER INFORMATION: Light Chain CDR-L1 from 110D7 antibody (Kabat
      numbering)

<400> SEQUENCE: 9

Lys Ala Ser Gln Asp Val Thr Thr Ala Val Ala
1               5                   10

<210> SEQ ID NO 10
<211> LENGTH: 7
<212> TYPE: PRT
<213> ORGANISM: artificial
<220> FEATURE:
<223> OTHER INFORMATION: Light Chain CDR-L2 from 110D7 antibody (Kabat
      numbering)

<400> SEQUENCE: 10

Trp Ala Ser Thr Arg His Thr
1               5

<210> SEQ ID NO 11
<211> LENGTH: 9
<212> TYPE: PRT
<213> ORGANISM: artificial
<220> FEATURE:
<223> OTHER INFORMATION: Light Chain CDR-L3 from 110D7 antibody (Kabat
      numbering)

<400> SEQUENCE: 11

Gln Gln His Tyr Arg Ile Pro Phe Thr
1               5

<210> SEQ ID NO 12
<211> LENGTH: 6
<212> TYPE: PRT
<213> ORGANISM: artificial
<220> FEATURE:
<223> OTHER INFORMATION: Heavy Chain CDR-H1 from 110D7 antibody (Kabat
      numbering)

<400> SEQUENCE: 12

Ser Asp Tyr Tyr Met Tyr
1               5

<210> SEQ ID NO 13
<211> LENGTH: 17
<212> TYPE: PRT
<213> ORGANISM: artificial
<220> FEATURE:
<223> OTHER INFORMATION: Heavy Chain CDR-H2 from 110D7 antibody (Kabat
      numbering)

<400> SEQUENCE: 13

Tyr Ile Ser Asn Gly Gly Gly Ser Thr Tyr Tyr Pro Asp Thr Val Lys
1               5                   10                  15

Gly

<210> SEQ ID NO 14
<211> LENGTH: 8
<212> TYPE: PRT
<213> ORGANISM: artificial
<220> FEATURE:
<223> OTHER INFORMATION: Heavy Chain CDR-H3 from 110D7 antibody (Kabat
      numbering)
```

-continued

<400> SEQUENCE: 14

Leu Ser Phe Tyr Ala Met Asp Tyr
1               5

<210> SEQ ID NO 15
<211> LENGTH: 18
<212> TYPE: DNA
<213> ORGANISM: artificial
<220> FEATURE:
<223> OTHER INFORMATION: Light Chain CDR-L1 from 110D7 antibody (IMGT
      numbering)

<400> SEQUENCE: 15
caggatgtga ctactgct                                                 18

<210> SEQ ID NO 16
<211> LENGTH: 9
<212> TYPE: DNA
<213> ORGANISM: artificial
<220> FEATURE:
<223> OTHER INFORMATION: Light Chain CDR-L2 from 110D7 antibody (IMGT
      numbering)

<400> SEQUENCE: 16 tgggcatcc                                                            9

<210> SEQ ID NO 17
<211> LENGTH: 27
<212> TYPE: DNA
<213> ORGANISM: artificial
<220> FEATURE:
<223> OTHER INFORMATION: Light Chain CDR-L3 from 110D7 antibody (IMGT
      numbering)

<400> SEQUENCE: 17
cagcaacatt ataggattcc attcacg                                       27

<210> SEQ ID NO 18
<211> LENGTH: 24
<212> TYPE: DNA
<213> ORGANISM: artificial
<220> FEATURE:
<223> OTHER INFORMATION: Heavy Chain CDR-H1 from 110D7 antibody (IMGT
      numbering)

<400> SEQUENCE: 18
ggattcactt tcagtgacta ttac                                          24

<210> SEQ ID NO 19
<211> LENGTH: 24
<212> TYPE: DNA
<213> ORGANISM: artificial
<220> FEATURE:
<223> OTHER INFORMATION: Heavy Chain CDR-H2 from 110D7 antibody (IMGT
      numbering)

<400> SEQUENCE: 19
attagtaatg gtggtggtag cacc                                          24

<210> SEQ ID NO 20
<211> LENGTH: 30
<212> TYPE: DNA
<213> ORGANISM: artificial
<220> FEATURE:
<223> OTHER INFORMATION: Heavy Chain CDR-H3 from 110D7 antibody (IMGT
      numbering)

<400> SEQUENCE: 20
gcaagactaa gtttctatgc tatggactac                    30

<210> SEQ ID NO 21
<211> LENGTH: 321
<212> TYPE: DNA
<213> ORGANISM: artificial
<220> FEATURE:
<223> OTHER INFORMATION: Light chain variable domain

<400> SEQUENCE: 21
gacattgtga tgacccagtc tcacaaattc atgtccacat cagtaggaga cagggtcagc    60
atcacctgca aggccagtca ggatgtgact actgctgtag cctggtatca acaaaaacca   120
ggacaatctc ctaaactact gatttactgg gcatccaccc ggcacactgg agtccctgat   180
cgcttcacag gcagtggatc tgggacagat tatactctca ccatcagcag tgtgcaggct   240
gaagacctgg cactttatta ctgtcagcaa cattatagga ttccattcac gttcggctcg   300
gggacaaagt tggaaataaa a                                             321

<210> SEQ ID NO 22
<211> LENGTH: 351
<212> TYPE: DNA
<213> ORGANISM: artificial
<220> FEATURE:
<223> OTHER INFORMATION: Heavy chain variable domain

<400> SEQUENCE: 22
gaagtgaagc tggtggagtc tgggggaggc ttagtgcagc ctggagggtc cctgaaactc    60
tcctgtgcaa cctctggatt cactttcagt gactattaca tgtattgggt tcgccagact   120
ccagagaaga ggctggagtg ggtcgcatac attagtaatg gtggtggtag cacctattat   180
ccagacactg taaagggccg attcaccatg tccagagaca atgccaagaa caccctgtac   240
ctgcaaatga gccgtctgaa gtctgaggac acagccatgt attactgtgc aagactaagt   300
ttctatgcta tggactactg gggtcaagga acctcagtca ccgtctcctc a            351

<210> SEQ ID NO 23
<211> LENGTH: 33
<212> TYPE: DNA
<213> ORGANISM: artificial
<220> FEATURE:
<223> OTHER INFORMATION: Light Chain CDR-L1 from 110D7 antibody (Kabat
      numbering)

<400> SEQUENCE: 23
aaggccagtc aggatgtgac tactgctgta gcc                30

<210> SEQ ID NO 24
<211> LENGTH: 21
<212> TYPE: DNA
<213> ORGANISM: artificial
<220> FEATURE:
<223> OTHER INFORMATION: Light Chain CDR-L2 from 110D7 antibody (Kabat
      numbering)

<400> SEQUENCE: 24
tgggcatcca cccggcacac t                             21

<210> SEQ ID NO 25
<211> LENGTH: 27
<212> TYPE: DNA
<213> ORGANISM: artificial

<220> FEATURE:
<223> OTHER INFORMATION: Light Chain CDR-L3 from 110D7 antibody (Kabat
      numbering)

<400> SEQUENCE: 25
cagcaacatt ataggattcc attcacg                                              27

<210> SEQ ID NO 26
<211> LENGTH: 18
<212> TYPE: DNA
<213> ORGANISM: artificial
<220> FEATURE:
<223> OTHER INFORMATION: Heavy Chain CDR-H1 from 110D7 antibody (Kabat
      numbering)

<400> SEQUENCE: 26
agtgactatt acatgtat                                                        18

<210> SEQ ID NO 27
<211> LENGTH: 51
<212> TYPE: DNA
<213> ORGANISM: artificial
<220> FEATURE:
<223> OTHER INFORMATION: Heavy Chain CDR-H2 from 110D7 antibody (Kabat
      numbering)

<400> SEQUENCE: 27
tacattagta atggtggtgg tagcacctat tatccagaca ctgtaaaggg c                    51

<210> SEQ ID NO 28
<211> LENGTH: 24
<212> TYPE: DNA
<213> ORGANISM: artificial
<220> FEATURE:
<223> OTHER INFORMATION: Heavy Chain CDR-H3 from 110D7 antibody (Kabat
      numbering)

<400> SEQUENCE: 28
ctaagtttct atgctatgga ctac                                                 24

<210> SEQ ID NO 29
<211> LENGTH: 894
<212> TYPE: PRT
<213> ORGANISM: homo sapiens
<220> FEATURE:
<221> NAME/KEY: misc_feature
<223> OTHER INFORMATION: Protein Axl (with peptide signal)

<400> SEQUENCE: 29

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
            115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asn Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro Trp Trp Tyr Val Leu Leu Gly Ala Val Val Ala Ala Ala Cys Val
450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu

```
                    530                 535                 540
Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
                580                 585                 590

Asp His Pro Asn Val Met Arg Leu Ile Gly Val Cys Phe Gln Gly Ser
            595                 600                 605

Glu Arg Glu Ser Phe Pro Ala Pro Val Val Ile Leu Pro Phe Met Lys
        610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
                660                 665                 670

Leu Ala Ala Arg Asn Cys Met Leu Asn Glu Asn Met Ser Val Cys Val
            675                 680                 685

Ala Asp Phe Gly Leu Ser Lys Lys Ile Tyr Asn Gly Asp Tyr Tyr Arg
        690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
                740                 745                 750

Val Glu Asn Ser Glu Ile Tyr Asp Tyr Leu Arg Gln Gly Asn Arg Leu
            755                 760                 765

Lys Gln Pro Ala Asp Cys Leu Asp Gly Leu Tyr Ala Leu Met Ser Arg
        770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
                820                 825                 830

Pro Pro Gly Ala Ala Gly Gly Ala Asp Pro Pro Thr Gln Pro Asp Pro
            835                 840                 845

Lys Asp Ser Cys Ser Cys Leu Thr Ala Ala Glu Val His Pro Ala Gly
        850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890
```

<210> SEQ ID NO 30
<211> LENGTH: 869
<212> TYPE: PRT
<213> ORGANISM: homo sapiens
<220> FEATURE:
<221> NAME/KEY: misc_feature
<223> OTHER INFORMATION: Protein Axl (without peptide signal)

<400> SEQUENCE: 30

```
Ala Pro Arg Gly Thr Gln Ala Glu Glu Ser Pro Phe Val Gly Asn Pro
1               5                   10                  15

Gly Asn Ile Thr Gly Ala Arg Gly Leu Thr Gly Thr Leu Arg Cys Gln
            20                  25                  30

Leu Gln Val Gln Gly Glu Pro Pro Glu Val His Trp Leu Arg Asp Gly
        35                  40                  45

Gln Ile Leu Glu Leu Ala Asp Ser Thr Gln Thr Gln Val Pro Leu Gly
    50                  55                  60

Glu Asp Glu Gln Asp Asp Trp Ile Val Val Ser Gln Leu Arg Ile Thr
65                  70                  75                  80

Ser Leu Gln Leu Ser Asp Thr Gly Gln Tyr Gln Cys Leu Val Phe Leu
                85                  90                  95

Gly His Gln Thr Phe Val Ser Gln Pro Gly Tyr Val Gly Leu Glu Gly
            100                 105                 110

Leu Pro Tyr Phe Leu Glu Glu Pro Glu Asp Arg Thr Val Ala Ala Asn
            115                 120                 125

Thr Pro Phe Asn Leu Ser Cys Gln Ala Gln Gly Pro Pro Glu Pro Val
    130                 135                 140

Asp Leu Leu Trp Leu Gln Asp Ala Val Pro Leu Ala Thr Ala Pro Gly
145                 150                 155                 160

His Gly Pro Gln Arg Ser Leu His Val Pro Gly Leu Asn Lys Thr Ser
                165                 170                 175

Ser Phe Ser Cys Glu Ala His Asn Ala Lys Gly Val Thr Thr Ser Arg
            180                 185                 190

Thr Ala Thr Ile Thr Val Leu Pro Gln Gln Pro Arg Asn Leu His Leu
            195                 200                 205

Val Ser Arg Gln Pro Thr Glu Leu Glu Val Ala Trp Thr Pro Gly Leu
210                 215                 220

Ser Gly Ile Tyr Pro Leu Thr His Cys Thr Leu Gln Ala Val Leu Ser
225                 230                 235                 240

Asn Asp Gly Met Gly Ile Gln Ala Gly Glu Pro Asp Pro Pro Glu Glu
                245                 250                 255

Pro Leu Thr Ser Gln Ala Ser Val Pro Pro His Gln Leu Arg Leu Gly
            260                 265                 270

Ser Leu His Pro His Thr Pro Tyr His Ile Arg Val Ala Cys Thr Ser
            275                 280                 285

Ser Gln Gly Pro Ser Ser Trp Thr His Trp Leu Pro Val Glu Thr Pro
    290                 295                 300

Glu Gly Val Pro Leu Gly Pro Pro Glu Asn Ile Ser Ala Thr Arg Asn
305                 310                 315                 320

Gly Ser Gln Ala Phe Val His Trp Gln Glu Pro Arg Ala Pro Leu Gln
                325                 330                 335

Gly Thr Leu Leu Gly Tyr Arg Leu Ala Tyr Gln Gly Gln Asp Thr Pro
            340                 345                 350

Glu Val Leu Met Asp Ile Gly Leu Arg Gln Glu Val Thr Leu Glu Leu
            355                 360                 365

Gln Gly Asp Gly Ser Val Ser Asn Leu Thr Val Cys Val Ala Ala Tyr
    370                 375                 380

Thr Ala Ala Gly Asp Gly Pro Trp Ser Leu Val Pro Leu Glu Ala
385                 390                 395                 400

Trp Arg Pro Gly Gln Ala Gln Pro Val His Gln Leu Val Lys Glu Pro
                405                 410                 415

Ser Thr Pro Ala Phe Ser Trp Pro Trp Trp Tyr Val Leu Leu Gly Ala
```

-continued

```
              420                 425                 430
Val Val Ala Ala Cys Val Leu Ile Leu Ala Leu Phe Leu Val His
            435                 440                 445
Arg Arg Lys Lys Glu Thr Arg Tyr Gly Glu Val Phe Glu Pro Thr Val
        450                 455                 460
Glu Arg Gly Glu Leu Val Val Arg Tyr Arg Val Arg Lys Ser Tyr Ser
465                 470                 475                 480
Arg Arg Thr Thr Glu Ala Thr Leu Asn Ser Leu Gly Ile Ser Glu Glu
                    485                 490                 495
Leu Lys Glu Lys Leu Arg Asp Val Met Val Asp Arg His Lys Val Ala
            500                 505                 510
Leu Gly Lys Thr Leu Gly Glu Gly Glu Phe Gly Ala Val Met Glu Gly
        515                 520                 525
Gln Leu Asn Gln Asp Asp Ser Ile Leu Lys Val Ala Val Lys Thr Met
    530                 535                 540
Lys Ile Ala Ile Cys Thr Arg Ser Glu Leu Glu Asp Phe Leu Ser Glu
545                 550                 555                 560
Ala Val Cys Met Lys Glu Phe Asp His Pro Asn Val Met Arg Leu Ile
                565                 570                 575
Gly Val Cys Phe Gln Gly Ser Glu Arg Glu Ser Phe Pro Ala Pro Val
            580                 585                 590
Val Ile Leu Pro Phe Met Lys His Gly Asp Leu His Ser Phe Leu Leu
        595                 600                 605
Tyr Ser Arg Leu Gly Asp Gln Pro Val Tyr Leu Pro Thr Gln Met Leu
    610                 615                 620
Val Lys Phe Met Ala Asp Ile Ala Ser Gly Met Glu Tyr Leu Ser Thr
625                 630                 635                 640
Lys Arg Phe Ile His Arg Asp Leu Ala Ala Arg Asn Cys Met Leu Asn
                645                 650                 655
Glu Asn Met Ser Val Cys Val Ala Asp Phe Gly Leu Ser Lys Lys Ile
            660                 665                 670
Tyr Asn Gly Asp Tyr Tyr Arg Gln Gly Arg Ile Ala Lys Met Pro Val
        675                 680                 685
Lys Trp Ile Ala Ile Glu Ser Leu Ala Asp Arg Val Tyr Thr Ser Lys
    690                 695                 700
Ser Asp Val Trp Ser Phe Gly Val Thr Met Trp Glu Ile Ala Thr Arg
705                 710                 715                 720
Gly Gln Thr Pro Tyr Pro Gly Val Glu Asn Ser Glu Ile Tyr Asp Tyr
                725                 730                 735
Leu Arg Gln Gly Asn Arg Leu Lys Gln Pro Ala Asp Cys Leu Asp Gly
            740                 745                 750
Leu Tyr Ala Leu Met Ser Arg Cys Trp Glu Leu Asn Pro Gln Asp Arg
        755                 760                 765
Pro Ser Phe Thr Glu Leu Arg Glu Asp Leu Glu Asn Thr Leu Lys Ala
    770                 775                 780
Leu Pro Pro Ala Gln Glu Pro Asp Glu Ile Leu Tyr Val Asn Met Asp
785                 790                 795                 800
Glu Gly Gly Gly Tyr Pro Glu Pro Gly Ala Ala Gly Gly Ala Asp
                805                 810                 815
Pro Pro Thr Gln Pro Asp Pro Lys Asp Ser Cys Ser Cys Leu Thr Ala
            820                 825                 830
Ala Glu Val His Pro Ala Gly Arg Tyr Val Leu Cys Pro Ser Thr Thr
        835                 840                 845
```

-continued

```
Pro Ser Pro Ala Gln Pro Ala Asp Arg Gly Ser Pro Ala Ala Pro Gly
    850                 855                 860

Gln Glu Asp Gly Ala
865

<210> SEQ ID NO 31
<211> LENGTH: 451
<212> TYPE: PRT
<213> ORGANISM: homo sapiens
<220> FEATURE:
<221> NAME/KEY: misc_feature
<223> OTHER INFORMATION: Extracellular domain of the protein Axl (with
      the peptide signal)

<400> SEQUENCE: 31

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asn Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320
```

-continued

```
Thr His Trp Leu Pro Val Glu Thr Pro Glu Gly Val Pro Leu Gly Pro
            325                 330                 335

Pro Glu Asn Ile Ser Ala Thr Arg Asn Gly Ser Gln Ala Phe Val His
        340                 345                 350

Trp Gln Glu Pro Arg Ala Pro Leu Gln Gly Thr Leu Leu Gly Tyr Arg
    355                 360                 365

Leu Ala Tyr Gln Gly Gln Asp Thr Pro Glu Val Leu Met Asp Ile Gly
370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro Trp Trp
    450

<210> SEQ ID NO 32
<211> LENGTH: 426
<212> TYPE: PRT
<213> ORGANISM: homo sapiens
<220> FEATURE:
<221> NAME/KEY: misc_feature
<223> OTHER INFORMATION: Extracellular domain of the protein Axl
      (without the peptide signal)

<400> SEQUENCE: 32

Ala Pro Arg Gly Thr Gln Ala Glu Glu Ser Pro Phe Val Gly Asn Pro
1               5                   10                  15

Gly Asn Ile Thr Gly Ala Arg Gly Leu Thr Gly Thr Leu Arg Cys Gln
            20                  25                  30

Leu Gln Val Gln Gly Glu Pro Pro Glu Val His Trp Leu Arg Asp Gly
        35                  40                  45

Gln Ile Leu Glu Leu Ala Asp Ser Thr Gln Thr Gln Val Pro Leu Gly
    50                  55                  60

Glu Asp Glu Gln Asp Asp Trp Ile Val Val Ser Gln Leu Arg Ile Thr
65                  70                  75                  80

Ser Leu Gln Leu Ser Asp Thr Gly Gln Tyr Gln Cys Leu Val Phe Leu
                85                  90                  95

Gly His Gln Thr Phe Val Ser Gln Pro Gly Tyr Val Gly Leu Glu Gly
            100                 105                 110

Leu Pro Tyr Phe Leu Glu Glu Pro Glu Asp Arg Thr Val Ala Ala Asn
        115                 120                 125

Thr Pro Phe Asn Leu Ser Cys Gln Ala Gln Gly Pro Pro Glu Pro Val
    130                 135                 140

Asp Leu Leu Trp Leu Gln Asp Ala Val Pro Leu Ala Thr Ala Pro Gly
145                 150                 155                 160

His Gly Pro Gln Arg Ser Leu His Val Pro Gly Leu Asn Lys Thr Ser
                165                 170                 175

Ser Phe Ser Cys Glu Ala His Asn Ala Lys Gly Val Thr Thr Ser Arg
            180                 185                 190

Thr Ala Thr Ile Thr Val Leu Pro Gln Gln Pro Arg Asn Leu His Leu
        195                 200                 205

Val Ser Arg Gln Pro Thr Glu Leu Glu Val Ala Trp Thr Pro Gly Leu
```

```
            210                 215                 220
Ser Gly Ile Tyr Pro Leu Thr His Cys Thr Leu Gln Ala Val Leu Ser
225                 230                 235                 240

Asn Asp Gly Met Gly Ile Gln Ala Gly Glu Pro Asp Pro Glu Glu
                245                 250                 255

Pro Leu Thr Ser Gln Ala Ser Val Pro Pro His Gln Leu Arg Leu Gly
                260                 265                 270

Ser Leu His Pro His Thr Pro Tyr His Ile Arg Val Ala Cys Thr Ser
                275                 280                 285

Ser Gln Gly Pro Ser Ser Trp Thr His Trp Leu Pro Val Glu Thr Pro
                290                 295                 300

Glu Gly Val Pro Leu Gly Pro Pro Glu Asn Ile Ser Ala Thr Arg Asn
305                 310                 315                 320

Gly Ser Gln Ala Phe Val His Trp Gln Glu Pro Arg Ala Pro Leu Gln
                325                 330                 335

Gly Thr Leu Leu Gly Tyr Arg Leu Ala Tyr Gln Gly Gln Asp Thr Pro
                340                 345                 350

Glu Val Leu Met Asp Ile Gly Leu Arg Gln Glu Val Thr Leu Glu Leu
                355                 360                 365

Gln Gly Asp Gly Ser Val Ser Asn Leu Thr Val Cys Val Ala Ala Tyr
370                 375                 380

Thr Ala Ala Gly Asp Gly Pro Trp Ser Leu Pro Val Pro Leu Glu Ala
385                 390                 395                 400

Trp Arg Pro Gly Gln Ala Gln Pro Val His Gln Leu Val Lys Glu Pro
                405                 410                 415

Ser Thr Pro Ala Phe Ser Trp Pro Trp Trp
                420                 425

<210> SEQ ID NO 33
<211> LENGTH: 4
<212> TYPE: PRT
<213> ORGANISM: artificial
<220> FEATURE:
<223> OTHER INFORMATION: Tetrapeptide

<400> SEQUENCE: 33

Gly Phe Leu Gly
1

<210> SEQ ID NO 34
<211> LENGTH: 4
<212> TYPE: PRT
<213> ORGANISM: artificial
<220> FEATURE:
<223> OTHER INFORMATION: Tetrapeptide

<400> SEQUENCE: 34

Ala Leu Ala Leu
1

<210> SEQ ID NO 35
<211> LENGTH: 5
<212> TYPE: PRT
<213> ORGANISM: artificial
<220> FEATURE:
<223> OTHER INFORMATION: Pentapeptide

<400> SEQUENCE: 35

Pro Val Gly Val Val
1               5
```

<210> SEQ ID NO 36
<211> LENGTH: 6
<212> TYPE: PRT
<213> ORGANISM: artificial
<220> FEATURE:
<223> OTHER INFORMATION: Light chain CDR-L1 from 1003A2 antibody (IMGT numbering)

<400> SEQUENCE: 36

Gln Asp Val Ile Thr Ala
1               5

<210> SEQ ID NO 37
<211> LENGTH: 3
<212> TYPE: PRT
<213> ORGANISM: artificial
<220> FEATURE:
<223> OTHER INFORMATION: Light chain CDR-L2 from 1003A2 antibody (IMGT numbering)

<400> SEQUENCE: 37

Trp Ala Ser
1

<210> SEQ ID NO 38
<211> LENGTH: 9
<212> TYPE: PRT
<213> ORGANISM: artificial
<220> FEATURE:
<223> OTHER INFORMATION: Light chain CDR-L3 from 1003A2 antibody (IMGT numbering)

<400> SEQUENCE: 38

Gln Gln His Phe Ser Thr Pro Leu Thr
1               5

<210> SEQ ID NO 39
<211> LENGTH: 8
<212> TYPE: PRT
<213> ORGANISM: artificial
<220> FEATURE:
<223> OTHER INFORMATION: Heavy chain CDR-H1 from 1003A2 antibody (IMGT numbering)

<400> SEQUENCE: 39

Gly Phe Thr Phe Asn Ser Tyr Ser
1               5

<210> SEQ ID NO 40
<211> LENGTH: 8
<212> TYPE: PRT
<213> ORGANISM: artificial
<220> FEATURE:
<223> OTHER INFORMATION: Heavy chain CDR-H2 from 1003A2 antibody (IMGT numbering)

<400> SEQUENCE: 40

Ile Ser Asn Gly Gly Gly Arg Thr
1               5

<210> SEQ ID NO 41
<211> LENGTH: 13
<212> TYPE: PRT
<213> ORGANISM: artificial
<220> FEATURE:
<223> OTHER INFORMATION: Heavy chain CDR-H3 from 1003A2 antibody (IMGT numbering)

-continued

<400> SEQUENCE: 41

Ala Arg Gly Thr Thr Glu Ser Tyr Tyr Ala Leu Asp Tyr
1               5                   10

<210> SEQ ID NO 42
<211> LENGTH: 107
<212> TYPE: PRT
<213> ORGANISM: artificial
<220> FEATURE:
<223> OTHER INFORMATION: Light chain variable domain

<400> SEQUENCE: 42

Asp Ile Val Met Thr Gln Ser His Lys Phe Met Ser Thr Ser Leu Gly
1               5                   10                  15

Asp Arg Ile Ser Ile Thr Cys Lys Ala Ser Gln Asp Val Ile Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Asn Leu Thr Ile Ser Ser Val Gln Ala
65                  70                  75                  80

Glu Asp Leu Ala Leu Tyr Tyr Cys Gln Gln His Phe Ser Thr Pro Leu
                85                  90                  95

Thr Phe Gly Ala Gly Thr Lys Leu Glu Leu Lys
            100                 105

<210> SEQ ID NO 43
<211> LENGTH: 120
<212> TYPE: PRT
<213> ORGANISM: artificial
<220> FEATURE:
<223> OTHER INFORMATION: Heavy chain variable domain

<400> SEQUENCE: 43

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30

Ser Met Ser Trp Val Arg Gln Thr Pro Glu Lys Arg Leu Glu Trp Val
        35                  40                  45

Ala Tyr Ile Ser Asn Gly Gly Gly Arg Thr Tyr Tyr Pro Asp Thr Ile
50                  55                  60

Lys Gly Arg Phe Thr Leu Ser Arg Asp Asn Asp Arg Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gly Thr Thr Glu Ser Tyr Tyr Ala Leu Asp Tyr Trp Gly Gln
            100                 105                 110

Gly Thr Ser Val Thr Val Ser Ser
        115                 120

<210> SEQ ID NO 44
<211> LENGTH: 11
<212> TYPE: PRT
<213> ORGANISM: artificial
<220> FEATURE:
<223> OTHER INFORMATION: Light chain CDR-L1 from 1003A2 antibody (Kabat
      numbering)

<400> SEQUENCE: 44

Lys Ala Ser Gln Asp Val Ile Thr Ala Val Ala
1               5                   10

<210> SEQ ID NO 45
<211> LENGTH: 7
<212> TYPE: PRT
<213> ORGANISM: artificial
<220> FEATURE:
<223> OTHER INFORMATION: Light chain CDR-L2 from 1003A2 antibody (Kabat
      numbering)

<400> SEQUENCE: 45

Trp Ala Ser Thr Arg His Thr
1               5

<210> SEQ ID NO 46
<211> LENGTH: 9
<212> TYPE: PRT
<213> ORGANISM: artificial
<220> FEATURE:
<223> OTHER INFORMATION: Light chain CDR-L3 from 1003A2 antibody (Kabat
      numbering)

<400> SEQUENCE: 46

Gln Gln His Phe Ser Thr Pro Leu Thr
1               5

<210> SEQ ID NO 47
<211> LENGTH: 6
<212> TYPE: PRT
<213> ORGANISM: artificial
<220> FEATURE:
<223> OTHER INFORMATION: Heavy chain CDR-H1 from 1003A2 antibody (Kabat
      numbering)

<400> SEQUENCE: 47

Asn Ser Tyr Ser Met Ser
1               5

<210> SEQ ID NO 48
<211> LENGTH: 17
<212> TYPE: PRT
<213> ORGANISM: artificial
<220> FEATURE:
<223> OTHER INFORMATION: Heavy chain CDR-H2 from 1003A2 antibody (Kabat
      numbering)

<400> SEQUENCE: 48

Tyr Ile Ser Asn Gly Gly Gly Arg Thr Tyr Tyr Pro Asp Thr Ile Lys
1               5                   10                  15

Gly

<210> SEQ ID NO 49
<211> LENGTH: 11
<212> TYPE: PRT
<213> ORGANISM: artificial
<220> FEATURE:
<223> OTHER INFORMATION: Heavy chain CDR-H3 from 1003A2 antibody (Kabat
      numbering)

<400> SEQUENCE: 49

Gly Thr Thr Glu Ser Tyr Tyr Ala Leu Asp Tyr
1               5                   10

```
<210> SEQ ID NO 50
<211> LENGTH: 18
<212> TYPE: DNA
<213> ORGANISM: artificial
<220> FEATURE:
<223> OTHER INFORMATION: Light chain CDR-L1 from 1003A2 antibody (IMGT
      numbering)

<400> SEQUENCE: 50
caggatgtga ttactgct                                                     18

<210> SEQ ID NO 51
<211> LENGTH: 9
<212> TYPE: DNA
<213> ORGANISM: artificial
<220> FEATURE:
<223> OTHER INFORMATION: Light chain CDR-L2 from 1003A2 antibody (IMGT
      numbering)

<400> SEQUENCE: 51 tgggcatcc                                                                9

<210> SEQ ID NO 52
<211> LENGTH: 27
<212> TYPE: DNA
<213> ORGANISM: artificial
<220> FEATURE:
<223> OTHER INFORMATION: Light chain CDR-L3 from 1003A2 antibody (IMGT
      numbering)

<400> SEQUENCE: 52
cagcaacatt ttagtactcc gctcacg                                           27

<210> SEQ ID NO 53
<211> LENGTH: 24
<212> TYPE: DNA
<213> ORGANISM: artificial
<220> FEATURE:
<223> OTHER INFORMATION: Heavy chain CDR-H1 from 1003A2 antibody (IMGT
      numbering)

<400> SEQUENCE: 53
ggattcactt tcaacagtta tagt                                              24

<210> SEQ ID NO 54
<211> LENGTH: 24
<212> TYPE: DNA
<213> ORGANISM: artificial
<220> FEATURE:
<223> OTHER INFORMATION: Heavy chain CDR-H2 from 1003A2 antibody (IMGT
      numbering)

<400> SEQUENCE: 54
attagtaatg gtggcggtcg cacc                                              24

<210> SEQ ID NO 55
<211> LENGTH: 39
<212> TYPE: DNA
<213> ORGANISM: artificial
<220> FEATURE:
<223> OTHER INFORMATION: Heavy chain CDR-H3 from 1003A2 antibody (IMGT
      numbering)

<400> SEQUENCE: 55
gcaagaggga ctacggagag ttattacgct ttggactac                              39

<210> SEQ ID NO 56
```

-continued

<211> LENGTH: 321
<212> TYPE: DNA
<213> ORGANISM: artificial
<220> FEATURE:
<223> OTHER INFORMATION: Light chain variable domain

<400> SEQUENCE: 56

```
gacattgtga tgacccagtc tcacaaattc atgtccacat cactaggaga caggatcagc      60
atcacctgca aggccagtca ggatgtgatt actgctgtag cctggtatca acaaaaacca     120
ggacaatctc ctaaattact gatttactgg gcatccaccc ggcacactgg agtccctgat     180
cgcttcacag gcagtggatc tgggacagat tataatctca ccatcagcag tgtgcaggct     240
gaagacctgg cactttatta ttgtcagcaa catttttagta ctccgctcac gttcggtgct    300
gggaccaaac tggagctgaa a                                               321
```

<210> SEQ ID NO 57
<211> LENGTH: 360
<212> TYPE: DNA
<213> ORGANISM: artificial
<220> FEATURE:
<223> OTHER INFORMATION: Heavy chain variable domain

<400> SEQUENCE: 57

```
gaagtgaagt tggtggagtc tgggggaggt ttagtgcagc ctggagggtc cctgaaactc      60
tcctgtgcag cctctggatt cactttcaac agttatagta tgtcttgggt tcgccagact     120
ccagagaaga ggctggagtg ggtcgcatac attagtaatg gtggcggtcg cacctactat     180
ccagacacta taagggccg attcaccctc tccagagaca tgacaggaa cacccctgtac      240
ctgcaaatga gcagtctgaa gtctgaggac acggccatgt attactgtgc aagagggact     300
acggagagtt attacgcttt ggactactgg ggtcaaggaa cctcagtcac cgtctcctca    360
```

<210> SEQ ID NO 58
<211> LENGTH: 33
<212> TYPE: DNA
<213> ORGANISM: artificial
<220> FEATURE:
<223> OTHER INFORMATION: Light chain CDR-L1 from 1003A2 antibody (Kabat
      numbering)

<400> SEQUENCE: 58

```
aaggccagtc aggatgtgat tactgctgta gcc                                   33
```

<210> SEQ ID NO 59
<211> LENGTH: 21
<212> TYPE: DNA
<213> ORGANISM: artificial
<220> FEATURE:
<223> OTHER INFORMATION: Light chain CDR-L2 from 1003A2 antibody (Kabat
      numbering)

<400> SEQUENCE: 59

```
tgggcatcca cccggcacac t                                                21
```

<210> SEQ ID NO 60
<211> LENGTH: 27
<212> TYPE: DNA
<213> ORGANISM: artificial
<220> FEATURE:
<223> OTHER INFORMATION: Light chain CDR-L3 from 1003A2 antibody (Kabat
      numbering)

<400> SEQUENCE: 60

```
cagcaacatt ttagtactcc gctcacg                                         27
```

<210> SEQ ID NO 61
<211> LENGTH: 18
<212> TYPE: DNA
<213> ORGANISM: artificial
<220> FEATURE:
<223> OTHER INFORMATION: Light chain CDR-H1 from 1003A2 antibody (Kabat numbering)

<400> SEQUENCE: 61

```
aacagttata gtatgtct                                                   18
```

<210> SEQ ID NO 62
<211> LENGTH: 51
<212> TYPE: DNA
<213> ORGANISM: artificial
<220> FEATURE:
<223> OTHER INFORMATION: Heavy chain CDR-H2 from 1003A2 antibody (Kabat numbering)

<400> SEQUENCE: 62

```
tacattagta atggtggcgg tcgcacctac tatccagaca ctataaaggg c              51
```

<210> SEQ ID NO 63
<211> LENGTH: 33
<212> TYPE: DNA
<213> ORGANISM: artificial
<220> FEATURE:
<223> OTHER INFORMATION: Heavy chain CDR-H3 from 1003A2 antibody (Kabat numbering)

<400> SEQUENCE: 63

```
gggactacgg agagttatta cgctttggac tac                                  33
```

<210> SEQ ID NO 64
<211> LENGTH: 6
<212> TYPE: PRT
<213> ORGANISM: artificial
<220> FEATURE:
<223> OTHER INFORMATION: Light chain CDR-L1 from 1024G11 (IMGT numbering)

<400> SEQUENCE: 64

Gln Asp Val Ile Thr Ala
1               5

<210> SEQ ID NO 65
<211> LENGTH: 3
<212> TYPE: PRT
<213> ORGANISM: artificial
<220> FEATURE:
<223> OTHER INFORMATION: Light chain CDR-L2 from 1024G11 (IMGT numbering)

<400> SEQUENCE: 65

Trp Ala Ser
1

<210> SEQ ID NO 66
<211> LENGTH: 9
<212> TYPE: PRT
<213> ORGANISM: artificial
<220> FEATURE:
<223> OTHER INFORMATION: Light chain CDR-L3 from 1024G11 (IMGT numbering)

<400> SEQUENCE: 66

```
Gln Gln His Leu Ser Thr Pro Leu Thr
1               5

<210> SEQ ID NO 67
<211> LENGTH: 8
<212> TYPE: PRT
<213> ORGANISM: artificial
<220> FEATURE:
<223> OTHER INFORMATION: Heavy chain CDR-H1 from 1024G11 (IMGT
      numbering)

<400> SEQUENCE: 67

Gly Phe Thr Phe Ser Ser Tyr Ser
1               5

<210> SEQ ID NO 68
<211> LENGTH: 8
<212> TYPE: PRT
<213> ORGANISM: artificial
<220> FEATURE:
<223> OTHER INFORMATION: Heavy chain CDR-H2 from 1024G11 (IMGT
      numbering)

<400> SEQUENCE: 68

Ile Ser Asn Gly Gly Gly Arg Thr
1               5

<210> SEQ ID NO 69
<211> LENGTH: 13
<212> TYPE: PRT
<213> ORGANISM: artificial
<220> FEATURE:
<223> OTHER INFORMATION: Heavy chain CDR-H3 from 1024G11 (IMGT
      numbering)

<400> SEQUENCE: 69

Ala Arg Gly Thr Thr Glu Ser Tyr Tyr Ala Met Asp Tyr
1               5                   10

<210> SEQ ID NO 70
<211> LENGTH: 107
<212> TYPE: PRT
<213> ORGANISM: artificial
<220> FEATURE:
<223> OTHER INFORMATION: Light chain variable domain

<400> SEQUENCE: 70

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ile Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Phe Cys Gln Gln His Leu Ser Thr Pro Leu
                85                  90                  95

Thr Phe Gly Ala Gly Thr Lys Leu Glu Leu Lys
            100                 105

<210> SEQ ID NO 71
```

```
<211> LENGTH: 120
<212> TYPE: PRT
<213> ORGANISM: artificial
<220> FEATURE:
<223> OTHER INFORMATION: Heavy chain variable domain

<400> SEQUENCE: 71

Glu Val Lys Leu Val Glu Ser Gly Gly Gly Leu Val Gln Pro Gly Gly
1               5                   10                  15

Ser Leu Asn Leu Ser Cys Ala Ala Ser Gly Phe Thr Phe Ser Ser Tyr
            20                  25                  30

Ser Met Ser Trp Val Arg Gln Thr Pro Glu Lys Arg Leu Glu Trp Val
        35                  40                  45

Ala Phe Ile Ser Asn Gly Gly Arg Thr Tyr Tyr Pro Asp Thr Val
    50                  55                  60

Lys Gly Arg Phe Thr Phe Ser Arg Asp Asn Ala Arg Asn Thr Leu Tyr
65                  70                  75                  80

Leu Gln Met Ser Ser Leu Asn Ser Glu Asp Thr Ala Met Tyr Phe Cys
                85                  90                  95

Ala Arg Gly Thr Thr Glu Ser Tyr Tyr Ala Met Asp Tyr Trp Gly Gln
            100                 105                 110

Gly Thr Ser Val Thr Val Ser Ser
        115                 120

<210> SEQ ID NO 72
<211> LENGTH: 11
<212> TYPE: PRT
<213> ORGANISM: artificial
<220> FEATURE:
<223> OTHER INFORMATION: Light chain CDR-L1 from 1024G11 (Kabat
      numbering)

<400> SEQUENCE: 72

Lys Ala Ser Gln Asp Val Ile Thr Ala Val Ala
1               5                   10

<210> SEQ ID NO 73
<211> LENGTH: 7
<212> TYPE: PRT
<213> ORGANISM: artificial
<220> FEATURE:
<223> OTHER INFORMATION: Light chain CDR-L2 from 1024G11 (Kabat
      numbering)

<400> SEQUENCE: 73

Trp Ala Ser Thr Arg His Thr
1               5

<210> SEQ ID NO 74
<211> LENGTH: 9
<212> TYPE: PRT
<213> ORGANISM: artificial
<220> FEATURE:
<223> OTHER INFORMATION: Light chain CDR-L3 from 1024G11 (Kabat
      numbering)

<400> SEQUENCE: 74

Gln Gln His Leu Ser Thr Pro Leu Thr
1               5

<210> SEQ ID NO 75
<211> LENGTH: 6
<212> TYPE: PRT
<213> ORGANISM: artificial
```

```
<220> FEATURE:
<223> OTHER INFORMATION: Heavy chain CDR-H1 from 1024G11 (Kabat
      numbering)

<400> SEQUENCE: 75

Ser Ser Tyr Ser Met Ser
1               5

<210> SEQ ID NO 76
<211> LENGTH: 17
<212> TYPE: PRT
<213> ORGANISM: artificial
<220> FEATURE:
<223> OTHER INFORMATION: Heavy chain CDR-H2 from 1024G11 (Kabat
      numbering)

<400> SEQUENCE: 76

Phe Ile Ser Asn Gly Gly Gly Arg Thr Tyr Tyr Pro Asp Thr Val Lys
1               5                   10                  15
Gly

<210> SEQ ID NO 77
<211> LENGTH: 11
<212> TYPE: PRT
<213> ORGANISM: artificial
<220> FEATURE:
<223> OTHER INFORMATION: Heavy chain CDR-H3 from 1024G11 (Kabat
      numbering)

<400> SEQUENCE: 77

Gly Thr Thr Glu Ser Tyr Tyr Ala Met Asp Tyr
1               5                   10

<210> SEQ ID NO 78
<211> LENGTH: 18
<212> TYPE: DNA
<213> ORGANISM: artificial
<220> FEATURE:
<223> OTHER INFORMATION: Light chain CDR-L1 from 1024G11 (IMGT
      numbering)

<400> SEQUENCE: 78
caggatgtga ttactgct                                              18

<210> SEQ ID NO 79
<211> LENGTH: 9
<212> TYPE: DNA
<213> ORGANISM: artificial
<220> FEATURE:
<223> OTHER INFORMATION: Light chain CDR-L2 from 1024G11 (IMGT
      numbering)

<400> SEQUENCE: 79 tgggcttcc                                                         9

<210> SEQ ID NO 80
<211> LENGTH: 27
<212> TYPE: DNA
<213> ORGANISM: artificial
<220> FEATURE:
<223> OTHER INFORMATION: Light chain CDR-L3 from 1024G11 (IMGT
      numbering)

<400> SEQUENCE: 80
cagcaacatt tgagcactcc gctcacg                                    27
```

```
<210> SEQ ID NO 81
<211> LENGTH: 24
<212> TYPE: DNA
<213> ORGANISM: artificial
<220> FEATURE:
<223> OTHER INFORMATION: Heavy chain CDR-H1 from 1024G11 (IMGT
      numbering)

<400> SEQUENCE: 81
ggattcactt tcagcagtta tagt                                          24

<210> SEQ ID NO 82
<211> LENGTH: 24
<212> TYPE: DNA
<213> ORGANISM: artificial
<220> FEATURE:
<223> OTHER INFORMATION: Heavy chain CDR-H2 from 1024G11 (IMGT
      numbering)

<400> SEQUENCE: 82
ataagtaatg ggggtggtcg cacc                                          24

<210> SEQ ID NO 83
<211> LENGTH: 39
<212> TYPE: DNA
<213> ORGANISM: artificial
<220> FEATURE:
<223> OTHER INFORMATION: Heavy chain CDR-H3 from 1024G11 (IMGT
      numbering)

<400> SEQUENCE: 83
gcaagaggga ctacggagag ttactatgct atggactac                          39

<210> SEQ ID NO 84
<211> LENGTH: 321
<212> TYPE: DNA
<213> ORGANISM: artificial
<220> FEATURE:
<223> OTHER INFORMATION: Light chain variable domain

<400> SEQUENCE: 84
gacattgtga tgacccagtc tcacaaattc atgtccacat cagtaggaga cagggtcagc    60
atcacctgca aggccagtca ggatgtgatt actgctgtag cctggtatca acaaaaacca   120
gggcaatctc ctaaactact gatttactgg gcttccaccc ggcacactgg agtccctgat   180
cgcttcacag gcagtggatc tgggacagat tatactctca ccatcagcag tgtgcaggct   240
gaagacctgg cactttattt ttgtcagcaa catttgagca ctccgctcac gttcggtgct   300
gggaccaaac tggagctgaa a                                            321

<210> SEQ ID NO 85
<211> LENGTH: 360
<212> TYPE: DNA
<213> ORGANISM: artificial
<220> FEATURE:
<223> OTHER INFORMATION: Heavy chain variable domain

<400> SEQUENCE: 85
gaagtgaagc tggtggagtc tgggggaggt ttagtgcagc ctggagggtc cctgaacctc    60
tcctgtgcag cctctggatt cactttcagc agttatagta tgtcttgggt tcgccagact   120
ccagagaaga ggctgagtg gtcgcattc ataagtaatg ggggtggtcg cacctactat   180
ccagacactg taaagggccg attcaccttc tccagagaca atgccaggaa cacctgtac   240
```
ctgcaaatga gcagtctgaa ttctgaggac acggccatgt atttctgtgc aagagggact    300
acggagagtt actatgctat ggactactgg ggtcaaggaa cctcagtcac cgtctcctca    360

<210> SEQ ID NO 86
<211> LENGTH: 33
<212> TYPE: DNA
<213> ORGANISM: artificial
<220> FEATURE:
<223> OTHER INFORMATION: Light chain CDR-L1 from 1024G11 (Kabat
      numbering)

<400> SEQUENCE: 86
aaggccagtc aggatgtgat tactgctgta gcc    33

<210> SEQ ID NO 87
<211> LENGTH: 21
<212> TYPE: DNA
<213> ORGANISM: artificial
<220> FEATURE:
<223> OTHER INFORMATION: Light chain CDR-L2 from 1024G11 (Kabat
      numbering)

<400> SEQUENCE: 87
tgggcttcca cccggcacac t    21

<210> SEQ ID NO 88
<211> LENGTH: 27
<212> TYPE: DNA
<213> ORGANISM: artificial
<220> FEATURE:
<223> OTHER INFORMATION: Light chain CDR-L3 from 1024G11 (Kabat
      numbering)

<400> SEQUENCE: 88
cagcaacatt tgagcactcc gctcacg    27

<210> SEQ ID NO 89
<211> LENGTH: 18
<212> TYPE: DNA
<213> ORGANISM: artificial
<220> FEATURE:
<223> OTHER INFORMATION: Heavy chain CDR-H1 from 1024G11 (Kabat
      numbering)

<400> SEQUENCE: 89
agcagttata gtatgtct    18

<210> SEQ ID NO 90
<211> LENGTH: 51
<212> TYPE: DNA
<213> ORGANISM: artificial
<220> FEATURE:
<223> OTHER INFORMATION: Heavy chain CDR-H2 from 1024G11 (Kabat
      numbering)

<400> SEQUENCE: 90
ttcataagta atgggggtgg tcgcacctac tatccagaca ctgtaaaggg c    51

<210> SEQ ID NO 91
<211> LENGTH: 33
<212> TYPE: DNA
<213> ORGANISM: artificial
<220> FEATURE:
<223> OTHER INFORMATION: Heavy chain CDR-H3 from 1024G11 (Kabat
      numbering)

-continued

```
<400> SEQUENCE: 91
gggactacgg agagttacta tgctatggac tac                    33
```

ANTIGEN BINDING PROTEINS

The present invention relates to novel antigen binding proteins, in particular monoclonal antibodies, capable of binding to the protein Axl as well as the amino and nucleic acid sequences coding for said proteins. From one aspect, the invention relates to novel antigen binding proteins, or antigen binding fragments, capable of binding to Axl and, by inducing internalization of Axl, being internalized into the cell. The invention also comprises the use of said antigen binding proteins as addressing products in conjugation with other anti-cancer compounds, such as toxins, radio-elements or drugs, and the use of same for the treatment of certain cancers.

"Axl" (also referred to as "Ufo", "Ark" or "Tyro7") was cloned from patients with chronic myeloid leukemia as an oncogene triggering the transformation when overexpressed by mouse NIH3T3. It belongs to a family of receptor tyrosine kinases (RTKs) called the TAM (Tyro3, Axl, Mer) family, which includes Tyro3 (Rse, Sky, Dtk, Etk, Brt, Tif), Axl, and Mer (Eyk, Nyk, Tyro-12) [Lemke G. et al. Nat. Rev. Immunol. (2008). 8, 327-336].

The human protein Axl is a 894 amino acids protein which sequence is represented in the sequence listing as SEQ ID NO. 29. Amino acids 1-25 corresponding to the signal peptide, the human protein Axl, without the said peptide signal, is represented in the sequence listing as SEQ ID NO. 30.

Gas6, originally isolated as growth arrest-specific gene, is the common ligand for the members of the TAM family [Varnum B. C. et al. Nature (1995). 373, 623-626]. Gas6 exhibits the highest affinity for Axl, followed by Tyro3 and finally by Mer [Nagata, K. et al. J. Biol. Chem. (1996). 271, 30022-30027]. Gas6 consists in a γ-carboxyglutamate (Gla)-rich domain that mediates binding to phospholipid membranes, four epidermal growth factor-like domains, and two laminin G-like (LG) domains [Manfioletti G., Brancolini, C., Avanzi, G. & Schneider, C. Mol. Cell Biol. (1993). 13, 4976-4985]. As many other RTKs, ligand binding results in receptor dimerization and autophosphorylation of tyrosine residues (tyrosine residues 779, 821 and 866 for the Axl receptor), which serve as docking sites for a variety of intracellular signaling molecules [Linger R. M., Keating, A. K., Earp, H. S. & Graham, D. K. Adv. Cancer Res. (2008). 100, 35-83]. Moreover, the Axl receptor can be activated through a ligant-independent process. This activation can occur when the Axl receptor is overexpressed.

Gas6/Axl signaling has been shown to regulate various cellular processes including cell proliferation, adhesion, migration and survival in a large variety of cells in vitro [Hafizi S. & Dahlback, B. FEBS J. (2006). 273, 5231-5244]. In addition, the TAM receptors are involved in the control of innate immunity; they inhibit the inflammatory responses to pathogens in dendritic cells (DCs) and macrophages. They also drive phagocytosis of apoptotic cells by these immune cells and they are required for the maturation and killing activity of natural killer (NK) cells [Lemke G. et al. Nat. Rev. Immunol. (2008). 8, 327-336].

Weakly expressed on normal cells, it is predominantly observed in fibroblasts, myeloid progenitor cells, macrophages, neural tissues, cardiac and skeletal muscle where it supports mainly cell survival. The Gas6/Axl system plays an important role in vascular biology by regulating vascular smooth muscle cell homeostasis [Korshunov, V. A., Mohan, A. M., Georger, M. A. & Berk, B. C. Circ. Res. (2006). 98, 1446-1452; Korshunov, V. A., Daul, M., Massett, M. P. & Berk, B. C. Hypertension (2007). 50, 1057-1062].

In tumor cells, Axl plays an important role in regulating cellular invasion and migration. Over-expression of Axl is associated not only with poor prognosis but also with increased invasiveness of various human cancers as reported for breast, colon, esophageal carcinoma, hepatocellular, gastric, glioma, lung, melanoma, osteosarcoma, ovarian, prostate, rhabdomyo sarcoma, renal, thyroid and uterine endometrial cancer [Linger R. M., Keating, A. K., Earp, H. S. & Graham, D. K. Adv. Cancer Res. (2008). 100, 35-83 and Verma A. Mol. Cancer Ther. (2011). 10, 1763-1773, for reviews]. In breast cancer, Axl appears to be a strong effector of the Epithelial-to-mesenchymal transition (EMT); EMT program contributes actively to migration and dissemination of cancer cells in the organism [Thiery J. P. Curr. Opin. Cell Biol. (2003). 15, 740-746].

Axl has also been shown to regulate angiogenesis. Indeed knockdown of Axl in endothelial cells impaired tube formation and migration [Holland S. J. et al. Cancer Res. (2005). 65, 9294-9303] as well as disturbed specific angiogenic signaling pathways [Li Y. et al. Oncogene (2009). 28, 3442-3455].

More recently several studies on a range of cellular models described the involvement of an Axl overexpression in drug resistance phenomena. The following table 1 summarized these studies.

TABLE 1

| Reference | Cancer type | Therapeutic agent | Cellular model |
|---|---|---|---|
| Macleod et al., 2005 | Ovarian cancer | Cisplatin | PE01/PE01CDDP |
| Mahadevan et al., 2007 | GIST | Imatinib inhibitor of c-kit/PDGFR | GIST882 > GIST-R |
| Lay et al., 2007 | NSCLC | Doxorubicin | CL-1 clones CL1-5F4 clones |
| Hong et al., 2008 | AML | Doxorubicin/ Cisplatin | U937 |
| Liu et al., 2009 | Breast Cancer | Lapatinib (HER1 and HER2 inhibitor) | HER2 (+) BT474 (J4) |
| Keating et al., 2010 | Astrocytoma | Temozolomide Carboplatin Vincristin | G12 A172 |
| Ye et al., 2010 | NSCLC | Erlotinib | HCC827 |

Complete references cited in table 1 above are as follow:
Macleod K. et al. Cancer Res. (2005). 65, 6789-6800
Mahadevan D. et al. Oncogene (2007). 26, 3909-3919
Lay J. D. et al. Cancer Res. (2007). 67, 3878-3887
Hong C. C. et al. Cancer Lett. (2008). 268, 314-324
Liu L. et al. Cancer Res. (2009). 69, 6871-6878
Keating A. K. et al. Mol. Cancer Ther. (2010). 9, 1298-1307
Ye X. et al. Oncogene (2010). 29, 5254-5264

In such a context the Axl RTK is considered as an interesting target in oncology. Several groups already developed anti-tumoral strategies targeting the gash/Axl axis, either using naked monoclonal antibodies or targeted small molecules [Verma A. Mol. Cancer Ther. (2011). 10, 1763-1773].

In a first embodiment, the invention relates to an antigen binding protein, or an antigen binding fragment thereof, which i) binds to the human protein Axl, and ii) is internalized following its binding to said human protein Axl.

More generally, the invention relates to the use of the protein Axl for the selection of an antigen binding protein, or an antigen binding fragment thereof, capable of being internalized following its binding to the said target Axl. More particularly, the said target is the extracellular domain of Axl.

In this particular aspect, the present invention is thus directed to an in vitro method for the screening of a compound, or a binding fragment thereof, capable of delivering or internalizing a molecule of interest into mammalian cells, said molecule of interest being covalently linked to said compound, wherein said method comprises the following steps of:

a) selecting a compound which is capable of binding the Axl protein, or the extracellular domain (ECD) thereof, or an epitope thereof;

b) optionally, covalently linking said molecule of interest, or a control molecule, to said compound selected in step a) to form a complex;

c) contacting said compound selected in step a), or said complex obtained in step b), with a mammal cell, preferably viable cell, expressing at its surface the Axl protein, or a functional fragment thereof;

d) determining whether said compound, or said molecule of interest or said complex, has been intracellularly delivered or internalized into said mammalian cell; and e) selecting said compound as a compound capable of delivering or internalizing a molecule of interest into a viable mammalian cell.

In a preferred embodiment, said compound capable of delivering or internalizing a molecule of interest into a viable mammalian cell is a protein (also designated herein polypeptide or peptide) or a protein-like compound comprising a peptidic structure, particularly an amino-acid sequence of at least 5, 10, 15 or more amino acids residues, said amino-acid residue(s) can be glycosylated.

When said compound capable of delivering or internalizing a molecule of interest into a viable mammalian cell is a protein or a protein-like compound, said compound is also called herein an "antigen binding protein", said antigen binding protein, or binding fragment thereof, can:

i) binds to the protein Axl, preferably the human Axl protein, and
ii) is internalized into a mammalian cell following its binding to said protein Axl when said Axl protein is expressed at the surface of said mammalian cell.

In a preferred embodiment, said mammalian viable cell is a human cell, preferably a cell naturally expressing the Axl protein receptor.

In a particular embodiment, the mammalian viable cells in step c) are mammalian cells which express recombinant Axl protein(s) at their surface.

In an also preferred embodiment, said molecule of interest is a cytotoxic molecule (also designated herein as cytoxic or cytostatic agent).

In an also preferred embodiment, said molecule of interest is covalently linked to said compound capable of binding the Axl protein using a linker, more preferably a peptidic linker, more preferably a cleavable peptidic linker, more preferably a linker which can be cleaved by natural intracellular compounds contained in the mammalian cell, particularly in the cytosol of said mammalian cell.

In an also preferred embodiment, said compound capable of binding the Axl protein is an antibody, or binding fragment thereof, which is directed against the Axl protein, or against an epitope thereof located into the Axl EDC domain.

The selection step of e) can be realized by any method known by the person skilled in the art for the evaluation of the intracellular delivering or internalization. Assay or test capable of demonstrating or evaluating the presence, absence, or the activity of said compound capable of specifically binding the Axl protein, or of said complex formed by said compound and said molecule of interest, or of said molecule of interest which is covalently linked to said compound, are well known by the skilled person (see some examples of such test or assay disclosed hereinafter, without limiting these tests to these following test examples).

More particularly, these tests or assays can be realized by FACS, Immuno fluorescence, flow cytometry, western-blot, cytotoxicity/cytostatic evaluations, etc. . . . .

In this aspect, the present invention is also directed to an in vitro method for the preparation of a cytotoxic or cytostatic complex capable of delivering a cytoxic compound into a mammalian cell, preferably a viable cell, said method comprising the step of:

covalently linked a cytotoxic agent to a compound which is:

i) capable of binding the Axl protein, preferably the human Axl protein, and
ii) is internalized into a mammalian cell following its binding to said protein Axl when said Axl protein is expressed at the surface of said mammalian cell.

Preferably said compound is a protein-like protein, more preferably an antibody which is directed against the Axl protein, or against an epitope thereof located into the Axl EDC domain, or a functional binding fragment of said antibody.

In preferred embodiment, said cytotoxic agent is covalently linked to the said anti-Axl antibody or functional fragment thereof, using a linker, more preferably a peptidic linker, more preferably a cleavable peptidic linker, more preferably a linker which can be cleaved, as non limitative example by natural intracellular compounds.

Like the other members of the TAM family, the Axl extracellular domain (ECD) has an organization closed to those of cell adhesion molecules. Axl ECD is characterized by a combination of two immunoglobulin-like domains followed by two adjacent fibronectin type III-like domains [O'Bryan J. P. et al. Mol. Cell Biol. (1991). 11, 5016-5031]. The two N-terminal immunoglobulin-like domains are sufficient for Gas6 ligand binding [Sasaki T. et al. EMBO J. (2006). 25, 80-87].

The ECD of the human protein Axl is a 451 amino acids fragment, corresponding to amino acids 1-451 of the sequence SEQ ID NO. 29, which sequence is represented in the sequence listing as SEQ ID NO. 31. Amino acids 1-25 corresponding to the signal peptide, the ECD of the human protein Axl without the signal peptide corresponds to the amino acids 26-451 of the sequence SEQ ID NO.29, represented by the sequence SEQ ID NO. 32.

To date different modes of internalization have been identified. They orientate the becoming the internalized proteins or proteic complex in the cell. After endocytosis, most membranes proteins or lipids returns to the cell surface (recycling), but some membrane components are delivered to late endosomes or the Golgi [Maxfield F. R. & McGraw, T. E. Nat. Rev. Mol. Cell Biol. (2004). 5, 121-132].

In a preferred embodiment, the invention relates to an antigen binding protein, or an antigen binding fragment thereof, which i) binds to the human protein Axl, and ii) is internalized following its binding to said human protein Axl.

In a most preferred embodiment, the invention relates to an antigen binding protein, or an antigen binding fragment thereof, which i) binds to the human protein Axl, preferably having the sequence SEQ ID NO. 29 or 30 or natural variant sequence thereof, and ii) is internalized following its binding to said human protein Axl.

A "binding protein" or "antigen binding protein" is a peptidic chain having a specific or general affinity with another protein or molecule (generally referred as antigen). Proteins are brought into contact and form a complex when binding is possible. The antigen binding protein of the invention can preferably be, without limitation, an antibody, a fragment or derivative of an antibody, a protein or a peptide.

By "antigen binding fragment" of an antigen binding protein according to the invention, it is intended to indicate any peptide, polypeptide, or protein retaining the ability to specifically bind to the target (also generally referred as antigen) of the antigen binding protein and comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of the antigen binding protein.

In a preferred embodiment wherein the antigen binding protein is an antibody, such "antigen binding fragments" are selected in the group consisting of Fv, scFv (sc for single chain), Fab, F(ab')$_2$, Fab', scFv-Fc fragments or diabodies, or any fragment of which the half-life time would have been increased by chemical modification, such as the addition of poly(alkylene)glycol such as poly(ethylene)glycol ("PEGylation") (pegylated fragments called Fv-PEG, scFv-PEG, Fab-PEG, F(ab')$_2$-PEG or Fab'-PEG) ("PEG" for Poly(Ethylene)Glycol), or by incorporation in a liposome, said fragments having at least one of the characteristic CDRs of the antibody according to the invention. Preferably, said "antigen binding fragments" will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of the affinity of the antibody from which it is descended, with respect to the target. Such a functional fragment will contain at the minimum 5 amino acids, preferably 10, 15, 25, 50 and 100 consecutive amino acids of the sequence of the antibody from which it is descended.

The term "epitope" is a region of an antigen that is bound by an antigen binding protein, including antibodies. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

In the present application, the epitope is localized into the extracellular domain of the human protein Axl.

According to a preferred embodiment of the invention, the antigen binding protein, or an antigen binding fragment thereof, specifically binds to an epitope localized into the human protein Axl extracellular domain, preferably having the sequence SEQ ID NO. 31 or 32 or natural variant sequence thereof.

By "binding", "binds", or the like, it is intended that the antigen binding protein, or antigen-binding fragment thereof, forms a complex with an antigen that is relatively stable under physiologic conditions. Methods for determining whether two molecules bind are well known in the art and include, for example, equilibrium dialysis, surface plasmon resonance, and the like.

In this sense, "$EC_{50}$" refers to 50% effective concentration. More precisely the term half maximal effective concentration ($EC_{50}$) corresponds to the concentration of a drug, antibody or toxicant which induces a response halfway between the baseline and maximum after some specified exposure time. It is commonly used as a measure of drug's potency. The $EC_{50}$ of a graded dose response curve therefore represents the concentration of a compound where 50% of its maximal effect is observed. The $EC_{50}$ of a quantal dose response curve represents the concentration of a compound where 50% of the population exhibits a response, after specified exposure duration. Concentration measures typically follow a sigmoidal curve, increasing rapidly over a relatively small change in concentration. This can be determined mathematically by derivation of the best-fit line.

As a preferred embodiment, the $EC_{50}$ determined in the present invention characterized the potency of antibody binding on the Axl ECD exposed on human tumor cells. The $EC_{50}$ parameter is determined using FACS analysis. The $EC_{50}$ parameter reflects the antibody concentration for which 50% of the maximal binding on the human Axl expressed on human tumor cells is obtained. Each $EC_{50}$ value was calculated as the midpoint of the dose response curve using a four-parameter regression curve fitting program (Prism Software). This parameter has been selected as to be representative of physiological/pathological conditions.

In an embodiment of the invention, the antigen binding protein, or an antigen binding fragment thereof, binds to its epitope with an $EC_{50}$ of at least $10^{-9}$ M, preferentially between $10^{-9}$ and $10^{-12}$ M.

Another embodiment of the invention is a process or method for the selection of an antigen binding protein, or an antigen binding fragment thereof, capable of being intracellularly internalizing into a mammalian cell, preferably into a human cell, preferably a viable cell, comprising the steps of:
  i) selecting antigen binding protein which binds to Axl, preferably to its ECD domain or to an epitope thereof; and
  ii) selecting said antigen binding protein from previous step i) which is internalized into a mammalian cell following their binding to an Axl protein expressed at the surface of said mammalian cell.

In a particular embodiment, said mammalian cell naturally expresses the Axl protein receptor at their surface or are mammalian cells which express recombinant Axl protein at their surface, preferably human cells.

Such method or process can comprise the steps of i) selecting antigen binding protein which binds to Axl with an $EC_{50}$ of at least $10^{-9}$ M and ii) selecting antigen binding protein from previous step which are internalized following their binding to Axl. The selection step of ii) can be realized by any method known by the person skilled in the art for the evaluation of the internalization. More particularly, tests can be realized by FACS, Immunofluorescence, flow cytometry, western-blot, cytotoxicity evaluations, etc. . . . .

Another characteristic of the antigen binding protein according to the invention is that it does not have any significant activity on the proliferation of tumor cells. More particularly, as illustrated in the following examples, the antigen binding protein according to the invention does not have any significant in vitro activity on the proliferation SN12C model.

In oncology, there are multiple mechanisms by which mAbs can exert therapeutic efficacy, but often their activity is not sufficient to produce a lasting benefit. Hence several strategies have been employed to enhance their activity particularly by combining them with drugs as chemotherapeutic agents. As an efficient alternative to combination protocols, immunotoxins become a novel therapeutic option for treating cancer [Beck A. et al. Discov. Med. (2010). 10, 329-339; Alley S. C. et al. J. Pharmacol. Exp. Ther. (2009). 330, 932-938]. Antibody-drug conjugates (ADCs) represent one approach where the ability to harness mAbs specificity and target the delivery of a cytotoxic agent to the tumor may significantly enhance both mAbs and drug activities. Ideally the mAb will specifically bind to an antigen with substantial expression on tumor cells but limited expression on normal cells.

The present invention focused on anti-Axl binding proteins, and more particularly on specific anti-Axl antibodies, presenting a high ability to be internalized following Axl binding. Such antigen binding proteins are interesting as one of the immuno-drug-conjugates components, so they addresse the linked cytotoxic into the targeted cancer cells. Once internalized the cytotoxic triggers cancer cell death.

Important keys to success with immunoconjugate therapy are thought to be the target antigen specificity and the internalization of the antigen-binding protein complexes into the cancer cells. Obviously non-internalizing antigens are less effective than internalizing antigens to delivers cytotoxic agents. Internalization processes are variable across antigens and depend on multiple parameters that can be influenced by binding proteins. Cell-surface RTKs constitute an interesting antigens family to investigate for such an approach.

In the biomolecule, the cytotoxic brings the cytotoxic activity and the used antigen binding protein brings its specificity against cancer cells, as well as a vector for entering within the cells to correctly address the cytotoxic.

Thus to improve the immunoconjugate molecule, the carrier-binding protein must exhibit high ability to internalize into the targeted cancer cells. The efficiency with which the binding proteins mediated internalisation differs significantly depending on the epitope targeted. Selection of potent internalizing anti-Axl binding proteins requires various experimental data studying not only Axl downregulation but also following anti-Axl binding proteins becoming into the cells.

In a preferred embodiment, the internalization of the antigen binding protein according to the invention can be evaluated preferably by immuno fluorescence (as exemplified hereinafter in the present application) or any method or process known by the person skilled in the art specific for the internalization mechanism.

In another preferred embodiment, as the complex Axl-antigen binding protein, according to the invention, is internalized after the binding of the binding protein of the invention to the ECD of said Axl, a reduction in the quantity of Axl at the surface of the cells is induced. This reduction can be quantified by any method known by the person skilled in the art (western-blot, FACS, immuno fluorescence, etc. . . . ).

In an embodiment of the invention, this reduction, thus reflecting the internalization, can be preferably measured by FACS and expressed as the difference or delta between the Mean Fluorescence Intensity (MFI) measured on untreated cells with the MFI measured with cells treated with the antigen binding protein according to the invention.

As non limitative example of the present invention, this delta is determined based on MFIs obtained with untreated cells and cells treated with the antigen binding protein of the invention as described in example 9 using i) human renal tumor SN12C cells after a 24 hour incubation period with the antigen binding protein of the invention and ii) a secondary antibody labelled with Alexa488. This parameter is defined as calculated with the following formula:

$$\Delta(MFI_{24h} \text{ untreated cells} - MFI_{24h} \text{ antigen binding protein treated cells})$$

This difference between MFIs reflects the Axl downregulation as MFIs are proportional of Axl expressed on the cell-surface.

In a more preferred and advantageous aspect, the antigen binding protein, or an antigen binding fragment thereof, of the invention consists of a monoclonal antibody, preferably an isolated Mab, triggering a $\Delta$ ($MFI_{24h}$ untreated cells-$MFI_{24h}$ treated cells) of at least 200, preferably of at least 300.

The antigen binding protein, or an antigen binding fragment thereof, according to the invention, induces a reduction of MFI of at least 200.

In more details, the above mentioned delta can be measured according to the following process, which must be considered as an illustrative and non limitative example:
 a) Treating and incubating tumoral cells of interest with the antigen binding protein of the invention;
 b) Treating the treated cells of step a) and, in parallel, untreated cells with the antigen binding protein of the invention,
 c) Measuring the MFI (representative of the quantity of Axl present at the surface) for the treated and the non treated cells with a secondary labeled antibody capable of binding to the antigen binding protein, and
 d) Calculating the delta as the subtraction of the MFI obtained with the treated cells from the MFI obtained with the non treated cells.

The terms "antibody", "antibodies" or "immunoglobulin" are used interchangeably in the broadest sense and include monoclonal antibodies, preferably isolated Mab, (e.g., full length or intact monoclonal antibodies), polyclonal antibodies, multivalent antibodies or multispecific antibodies (e.g., bispecific antibodies so long as they exhibit the desired biological activity).

More particularly, such molecule consists of a glycoprotein comprising at least two heavy (H) chains and two light (L) chains inter-connected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

Antibodies in the sense of the invention also include certain antibody fragments, thereof. The said antibody fragments exhibit the desired binding specificity and affinity, regardless of the source or immunoglobulin type (i.e., IgG, IgE, IgM, IgA, etc.), i.e., they are capable of binding specifically the Axl protein with an affinity comparable to the full-length antibodies of the invention.

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975).

The term "monoclonal antibody" or "Mab" as used herein refers to an antibody molecule that is directed against a specific antigen and which may be produced by a single clone of B cells or hybridoma. Monoclonal antibodies may also be recombinant, i.e. produced by protein engineering. In addition, in contrast with preparations of polyclonal antibodies which typically include various antibodies directed against various determinants, or epitopes, each monoclonal antibody is directed against a single epitope of the antigen. The invention relates to antibodies isolated or obtained by purification from natural sources or obtained by genetic recombination or chemical synthesis.

A preferred embodiment of the invention is an antigen binding protein, or an antigen binding fragment thereof, comprising or consisting of an antibody selected in the group consisting of:

a) an antibody comprising the three light chain CDRs comprising the sequences SEQ ID NOs. 1, 2 and 3, or any sequence exhibiting at least 80%, preferably 85%, 90%, 95% and 98% identity with SEQ ID NOs. 1, 2 and 3; and the three heavy chain CDRs comprising the sequences SEQ ID NOs. 4, 5 and 6, or any sequence exhibiting at least 80%, preferably 85%, 90%, 95% and 98% identity with SEQ ID NOs. 4, 5 and 6;

b) an antibody comprising the three light chain CDRs comprising the sequences SEQ ID NOs. 36, 37 and 38, or any sequence exhibiting at least 80%, preferably 85%, 90%, 95% and 98% identity with SEQ ID NOs. 36, 37 and 38; and the three heavy chain CDRs comprising the sequences SEQ ID NOs. 39, 40 and 41, or any sequence exhibiting at least 80%, preferably 85%, 90%, 95% and 98% identity with SEQ ID NOs. 39, 40 and 41;

c) an antibody comprising the three light chain CDRs comprising the sequences SEQ ID NOs. 64, 65 and 66, or any sequence exhibiting at least 80%, preferably 85%, 90%, 95% and 98% identity with SEQ ID NOs. 64, 65 and 66; and the three heavy chain CDRs comprising the sequences SEQ ID NOs. 67, 68 and 69, or any sequence exhibiting at least 80%, preferably 85%, 90%, 95% and 98% identity with SEQ ID NOs. 67, 68 and 69.

In a more preferred embodiment of the invention, the antigen binding protein, or an antigen binding fragment thereof, consists of an antibody selected in the group consisting of:

a) an antibody comprising the three light chain CDRs, as defined according to the IMGT numbering system, comprising the sequences SEQ ID NOs. 1, 2 and 3; and the three heavy chain CDRs, as defined according to the IMGT numbering system, comprising the sequences SEQ ID NOs. 4, 5 and 6;

b) an antibody comprising the three light chain CDRs, as defined according to the IMGT numbering system, comprising the sequences SEQ ID NOs. 36, 37 and 38; and the three heavy chain CDRs, as defined according to the IMGT numbering system, comprising the sequences SEQ ID NOs. 39, 40 and 41;

c) an antibody comprising the three light chain CDRs, as defined according to the IMGT numbering system, comprising the sequences SEQ ID NOs. 64, 65 and 66; and the three heavy chain CDRs, as defined according to the IMGT numbering system, comprising the sequences SEQ ID NOs. 67, 68 and 69.

In a preferred aspect, by CDR regions or CDR(s), it is intended to indicate the hypervariable regions of the heavy and light chains of the immunoglobulins as defined by IMGT. Without any contradictory mention, the CDRs will be defined in the present specification according to the IMGT numbering system.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

It must be understood that, without contradictory specification in the present specification, complementarity-determining regions or CDRs, mean the hypervariable regions of the heavy and light chains of immunoglobulins as defined according to the IMGT numbering system.

Nevertheless, CDRs can also be defined according to the Kabat numbering system (Kabat et al., Sequences of proteins of immunological interest, 5$^{th}$ Ed., U.S. Department of Health and Human Services, NIH, 1991, and later editions). There are three heavy-chain CDRs and three light-chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes.

According to the Kabat numbering system, the present invention relates to an antigen binding protein, or an antigen binding fragment thereof, consisting of an antibody selected in the group consisting of:

a) an antibody comprising the three light chain CDRs, as defined according to Kabat numbering system, comprising the sequences SEQ ID NOs. 9, 10 and 11, or any sequence exhibiting at least 80%, preferably 85%, 90%, 95% and 98% identity with SEQ ID NOs. 9, 10 and 11; and the three heavy chain CDRs, as defined according to Kabat numbering system, comprising the sequences SEQ ID NOs. 12, 13 and 14, or any sequence exhibiting at least 80%, preferably 85%, 90%, 95% and 98% identity with SEQ ID NOs. 12, 13 and 14;

b) an antibody comprising the three light chain CDRs, as defined according to Kabat numbering system, comprising the sequences SEQ ID NOs. 44, 45 and 46, or any sequence exhibiting at least 80%, preferably 85%, 90%, 95% and 98% identity with SEQ ID NOs. 44, 45 and 46; and the three heavy chain CDRs, as defined according to Kabat numbering system, comprising the sequences SEQ ID NOs. 47, 48 and 49, or any sequence exhibiting at least 80%, preferably 85%, 90%, 95% and 98% identity with SEQ ID NOs. 47, 48 and 49;

c) an antibody comprising the three light chain CDRs, as defined according to Kabat numbering system, comprising the sequences SEQ ID NOs. 72, 73 and 74, or any sequence exhibiting at least 80%, preferably 85%, 90%, 95% and 98% identity with SEQ ID NOs. 72, 73 and 74; and the three heavy chain CDRs, as defined according to Kabat numbering system, comprising the sequences SEQ ID NOs. 75, 76 and 77, or any sequence exhibiting at least 80%, preferably 85%, 90%, 95% and 98% identity with SEQ ID NOs. 75, 76 and 77.

In the sense of the present invention, the "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid nucleotide or residue is identical between the two sequences, preferably between the two complete sequences, dividing the number of identical positions by the total number of positions in the alignment window and multiplying the result by 100 to obtain the percentage identity between the two sequences.

For example, the BLAST program, "BLAST 2 sequences" (Tatusova et al., "Blast 2 sequences—a new tool for comparing protein and nucleotide sequences", FEMS Microbiol., 1999, Lett. 174:247-250) available on the site www.ncbi.nlm.nih.gov/gorf/b12.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antigen binding proteins likely to be generated.

As a non-limiting example, table 2 below summarizes the possible substitutions likely to be carried out without resulting in a significant modification of the biological activity of the corresponding modified antigen binding protein; inverse substitutions are naturally possible under the same conditions.

TABLE 2

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

An embodiment of the invention relates to an antigen binding protein, or an antigen binding fragment thereof, comprising the three light chain CDRs comprising the sequences SEQ ID NOs. 1, 2 and 3, or any sequence exhibiting at least 80%, preferably 85%, 90%, 95% and 98% identity with SEQ ID NOs.1, 2 and 3; and a heavy chain variable domain of sequence SEQ ID NO. 8, or any sequence exhibiting at least 80%, preferably 85%, 90%, 95% and 98% identity with SEQ ID NO. 8.

According to a preferred embodiment of the invention, the antigen binding protein, or an antigen binding fragment thereof comprises the three light chain CDRs comprising the sequences SEQ ID NOs. 1, 2 and 3; and a heavy chain variable domain of sequence SEQ ID NO. 8, or any sequence exhibiting at least 80% identity with SEQ ID NO.8.

According to another preferred embodiment of the invention, the antigen binding protein, or an antigen binding fragment thereof comprises a heavy chain variable domain of sequence SEQ ID NO. 8, or any sequence exhibiting at least 80% identity with SEQ ID NO.8.

By "any sequence exhibiting at least 80% identity with SEQ ID NO.8", its is intended to designate the sequence exhibiting the three heavy chain CDRs SEQ ID NOs. 4, 5 and 6 and, in addition, exhibiting at least 80% identity with the full sequence SEQ ID NO.8 outside the sequences corresponding to the CDRs, i.e. SEQ ID NOs. 4, 5 and 6.

Another embodiment of the invention relates to an antigen binding protein, or an antigen binding fragment thereof, comprising a light chain variable domain of sequence SEQ ID NO. 7, or any sequence exhibiting at least 80%, preferably 85%, 90%, 95% and 98% identity with SEQ ID NO. 7; and the three heavy chain CDRs comprising the sequences SEQ ID NOs. 4, 5 and 6, or any sequence exhibiting at least 80%, preferably 85%, 90%, 95% and 98% identity with SEQ ID NOs. 4, 5 and 6.

According to a preferred embodiment of the invention, the antigen binding protein, or an antigen binding fragment thereof, comprises a light chain variable domain of sequence SEQ ID NO. 7, or any sequence exhibiting at least 80% identity with SEQ ID NO.7; and the three heavy chain CDRs comprising the sequences SEQ ID NOs. 4, 5 and 6.

According to another preferred embodiment of the invention, the antigen binding protein, or an antigen binding fragment thereof, comprises a light chain variable domain of sequence SEQ ID NO. 7, or any sequence exhibiting at least 80% identity with SEQ ID NO.7.

By "any sequence exhibiting at least 80% identity with SEQ ID NO.7", its is also intended to designate the sequence exhibiting the three light chain CDRs SEQ ID NOs. 1, 2 and 3 and, in addition, exhibiting at least 80% identity with the full sequence SEQ ID NO.7 outside the sequences corresponding to the CDRs, i.e. SEQ ID NOs. 1, 2 and 3.

Another embodiment of the invention relates to an antigen binding protein, or an antigen binding fragment thereof, comprising a light chain variable domain of sequence SEQ ID NO. 7, or any sequence exhibiting at least 80%, preferably 85%, 90%, 95% and 98% identity with SEQ ID NO. 7; and a heavy chain variable domain of sequence SEQ ID NO. 8, or any sequence exhibiting at least 80%, preferably 85%, 90%, 95% and 98% identity with SEQ ID NO.8.

According to a preferred embodiment of the invention, the antigen binding protein, or an antigen binding fragment thereof, comprises a light chain variable domain of sequence SEQ ID NO. 7, or any sequence exhibiting at least 80% identity with SEQ ID NO.7 and a heavy chain variable domain of sequence SEQ ID NO. 8, or any sequence exhibiting at least 80% identity with SEQ ID NO.8.

An embodiment of the invention relates to an antigen binding protein, or an antigen binding fragment thereof, comprising the three light chain CDRs comprising the sequences SEQ ID NOs. 36, 37 and 38, or any sequence exhibiting at least 80%, preferably 85%, 90%, 95% and 98% identity with SEQ ID NOs.36, 37 and 38; and a heavy chain variable domain of sequence SEQ ID NO. 43, or any sequence exhibiting at least 80%, preferably 85%, 90%, 95% and 98% identity with SEQ ID NO. 43.

According to a preferred embodiment of the invention, the antigen binding protein, or an antigen binding fragment thereof comprises the three light chain CDRs comprising the sequences SEQ ID NOs. 36, 37 and 38; and a heavy chain variable domain of sequence SEQ ID NO. 43, or any sequence exhibiting at least 80% identity with SEQ ID NO.43.

According to another preferred embodiment of the invention, the antigen binding protein, or an antigen binding fragment thereof comprises a heavy chain variable domain of sequence SEQ ID NO. 43, or any sequence exhibiting at least 80% identity with SEQ ID NO.43.

By "any sequence exhibiting at least 80% identity with SEQ ID NO.43", it is intended to designate the sequence exhibiting the three heavy chain CDRs SEQ ID NOs. 39, 40 and 41 and, in addition, exhibiting at least 80% identity with the full sequence SEQ ID NO.43 outside the sequences corresponding to the CDRs, i.e. SEQ ID NOs. 39, 40 and 41.

Another embodiment of the invention relates to an antigen binding protein, or an antigen binding fragment thereof, comprising a light chain variable domain of sequence SEQ ID NO. 42, or any sequence exhibiting at least 80%, preferably 85%, 90%, 95% and 98% identity with SEQ ID NO. 42; and the three heavy chain CDRs comprising the sequences SEQ ID NOs. 39, 40 and 41, or any sequence exhibiting at least 80%, preferably 85%, 90%, 95% and 98% identity with SEQ ID NOs. 39, 40 and 41.

According to a preferred embodiment of the invention, the antigen binding protein, or an antigen binding fragment thereof, comprises a light chain variable domain of sequence SEQ ID NO. 42, or any sequence exhibiting at least 80% identity with SEQ ID NO.42; and the three heavy chain CDRs comprising the sequences SEQ ID NOs. 39, 40 and 41.

According to another preferred embodiment of the invention, the antigen binding protein, or an antigen binding fragment thereof, comprises a light chain variable domain of sequence SEQ ID NO. 42, or any sequence exhibiting at least 80% identity with SEQ ID NO.42.

By "any sequence exhibiting at least 80% identity with SEQ ID NO.42", its is also intended to designate the sequence exhibiting the three light chain CDRs SEQ ID NOs. 36, 37 and 38 and, in addition, exhibiting at least 80% identity with the full sequence SEQ ID NO.42 outside the sequences corresponding to the CDRs, i.e. SEQ ID NOs. 36, 37 and 38.

Another embodiment of the invention relates to an antigen binding protein, or an antigen binding fragment thereof, comprising a light chain variable domain of sequence SEQ ID NO. 42, or any sequence exhibiting at least 80%, preferably 85%, 90%, 95% and 98% identity with SEQ ID NO. 42; and a heavy chain variable domain of sequence SEQ ID NO. 43, or any sequence exhibiting at least 80%, preferably 85%, 90%, 95% and 98% identity with SEQ ID NO.43.

According to a preferred embodiment of the invention, the antigen binding protein, or an antigen binding fragment thereof, comprises a light chain variable domain of sequence SEQ ID NO. 42, or any sequence exhibiting at least 80% identity with SEQ ID NO.42 and a heavy chain variable domain of sequence SEQ ID NO. 43, or any sequence exhibiting at least 80% identity with SEQ ID NO.43.

An embodiment of the invention relates to an antigen binding protein, or an antigen binding fragment thereof, comprising the three light chain CDRs comprising the sequences SEQ ID NOs. 64, 65 and 66, or any sequence exhibiting at least 80%, preferably 85%, 90%, 95% and 98% identity with SEQ ID NOs.64, 65 and 66; and a heavy chain variable domain of sequence SEQ ID NO. 71, or any sequence exhibiting at least 80%, preferably 85%, 90%, 95% and 98% identity with SEQ ID NO. 71.

According to a preferred embodiment of the invention, the antigen binding protein, or an antigen binding fragment thereof comprises the three light chain CDRs comprising the sequences SEQ ID NOs. 64, 65 and 66; and a heavy chain variable domain of sequence SEQ ID NO. 71, or any sequence exhibiting at least 80% identity with SEQ ID NO.71.

According to another preferred embodiment of the invention, the antigen binding protein, or an antigen binding fragment thereof comprises a heavy chain variable domain of sequence SEQ ID NO. 71, or any sequence exhibiting at least 80% identity with SEQ ID NO.71.

By "any sequence exhibiting at least 80% identity with SEQ ID NO.71", its is intended to designate the sequence exhibiting the three heavy chain CDRs SEQ ID NOs. 67, 68 and 69 and, in addition, exhibiting at least 80% identity with the full sequence SEQ ID NO.71 outside the sequences corresponding to the CDRs, i.e. SEQ ID NOs. 67, 68 and 69.

Another embodiment of the invention relates to an antigen binding protein, or an antigen binding fragment thereof, comprising a light chain variable domain of sequence SEQ ID NO. 70, or any sequence exhibiting at least 80%, preferably 85%, 90%, 95% and 98% identity with SEQ ID NO. 70; and the three heavy chain CDRs comprising the sequences SEQ ID NOs. 67, 68 and 69, or any sequence exhibiting at least 80%, preferably 85%, 90%, 95% and 98% identity with SEQ ID NOs. 67, 68 and 69.

According to a preferred embodiment of the invention, the antigen binding protein, or an antigen binding fragment thereof, comprises a light chain variable domain of sequence SEQ ID NO. 70, or any sequence exhibiting at least 80% identity with SEQ ID NO.70; and the three heavy chain CDRs comprising the sequences SEQ ID NOs. 67, 68 and 69.

According to another preferred embodiment of the invention, the antigen binding protein, or an antigen binding fragment thereof, comprises a light chain variable domain of sequence SEQ ID NO. 70, or any sequence exhibiting at least 80% identity with SEQ ID NO.70.

By "any sequence exhibiting at least 80% identity with SEQ ID NO.70", its is also intended to designate the sequence exhibiting the three light chain CDRs SEQ ID NOs. 64, 65 and 66 and, in addition, exhibiting at least 80% identity with the full sequence SEQ ID NO.70 outside the sequences corresponding to the CDRs, i.e. SEQ ID NOs. 64, 65 and 66.

Another embodiment of the invention relates to an antigen binding protein, or an antigen binding fragment thereof, comprising a light chain variable domain of sequence SEQ ID NO. 70, or any sequence exhibiting at least 80%, preferably 85%, 90%, 95% and 98% identity with SEQ ID NO. 70; and a heavy chain variable domain of sequence SEQ ID NO. 71, or any sequence exhibiting at least 80%, preferably 85%, 90%, 95% and 98% identity with SEQ ID NO.71.

According to a preferred embodiment of the invention, the antigen binding protein, or an antigen binding fragment thereof, comprises a light chain variable domain of sequence SEQ ID NO. 70, or any sequence exhibiting at least 80% identity with SEQ ID NO.70 and a heavy chain variable domain of sequence SEQ ID NO. 71, or any sequence exhibiting at least 80% identity with SEQ ID NO.71.

For more clarity, Tables 3a-3c below summarize the various amino acid sequences corresponding to the antigen binding proteins of the invention.

TABLE 3a

| CDR numbering | | Heavy chain | Light chain | SEQ ID NO. |
|---|---|---|---|---|
| 110D7 | IMGT | | CDR-L1 | 1 |
| | | | CDR-L2 | 2 |
| | | | CDR-L3 | 3 |
| | | CDR-H1 | | 4 |
| | | CDR-H2 | | 5 |
| | | CDR-H3 | | 6 |
| | Kabat | | CDR-L1 | 9 |
| | | | CDR-L2 | 10 |
| | | | CDR-L3 | 11 |
| | | CDR-H1 | | 12 |
| | | CDR-H2 | | 13 |
| | | CDR-H3 | | 14 |
| | | | variable domain | 7 |
| | | variable domain | | 8 |

TABLE 3b

| 1003A2 | IMGT | | CDR-L1 | 36 |
|---|---|---|---|---|
| | | | CDR-L2 | 37 |
| | | | CDR-L3 | 38 |
| | | CDR-H1 | | 39 |
| | | CDR-H2 | | 40 |
| | | CDR-H3 | | 41 |
| | Kabat | | CDR-L1 | 44 |
| | | | CDR-L2 | 45 |
| | | | CDR-L3 | 46 |
| | | CDR-H1 | | 47 |
| | | CDR-H2 | | 48 |
| | | CDR-H3 | | 49 |
| | | | variable domain | 42 |
| | | variable domain | | 43 |

TABLE 3c

| 1024G11 | IMGT | | CDR-L1 | 64 |
|---|---|---|---|---|
| | | | CDR-L2 | 65 |
| | | | CDR-L3 | 66 |
| | | CDR-H1 | | 67 |
| | | CDR-H2 | | 68 |
| | | CDR-H3 | | 69 |
| | Kabat | | CDR-L1 | 72 |
| | | | CDR-L2 | 73 |
| | | | CDR-L3 | 74 |
| | | CDR-H1 | | 75 |
| | | CDR-H2 | | 76 |
| | | CDR-H3 | | 77 |
| | | | variable domain | 70 |
| | | variable domain | | 71 |

A specific aspect of the present invention relates to a murine antibody, or its derived compounds or antigen binding fragments, characterized in that said antibody also comprises light-chain and heavy-chain constant regions derived from an antibody of a species heterologous with the mouse, notably man.

Another specific aspect of the present invention relates to a chimeric antibody, or its derived compounds or antigen binding fragments, characterized in that said antibody also comprises light-chain and heavy-chain constant regions derived from a species heterologous with the mouse, notably human.

Yet another specific aspect of the present invention relates to a humanized antibody, or its derived compounds or antigen binding fragments, characterized in that the constant regions of the light-chain and the heavy-chain derived from human antibody are, respectively, the lambda or kappa region and the gamma-1, gamma-2 or gamma-4 region.

Another aspect of the invention is an antigen binding protein consisting of a monoclonal antibody selected in the group consisting of:

a) the monoclonal antibody 110D7 derived from the hybridoma I-3959 deposited at the CNCM, Institut Pasteur, France, on the 2 Apr. 2008, or an antigen binding fragment thereof;

b) the monoclonal antibody 1003A2 derived from the hybridoma I-4499 deposited at the CNCM, Institut Pasteur, France, on the 28 Jul. 2011, or an antigen binding fragment thereof;

c) the monoclonal antibody 1024G11 derived from the hybridoma I-4501 deposited at the CNCM, Institut Pasteur, France, on the 28 Jul. 2011, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on 2 Apr. 2008, under number 1-3959; 28 Jul. 2011 under number 1-4499 or 28 Jul. 2011 under number 1-4501.

Said hybridoma were obtained by the fusion of Balb/C immunized mice splenocytes/lymphocytes and cells of the myeloma Sp 2/O-Ag 14 cell line.

According to another aspect, the invention relates to a murine hybridoma capable of secreting an antibody comprising the three light chain CDRs comprising the sequences SEQ ID NOs. 1, 2 and 3; and the three heavy chain CDRs comprising the sequences SEQ ID NOs. 4, 5 and 6, said hybridoma being filed at the CNCM, Pasteur Institute, Paris, France, on 2 Apr. 2008, under number 1-3959.

According to another aspect, the invention relates to a murine hybridoma capable of secreting an antibody comprising the three light chain CDRs comprising the sequences SEQ ID NOs. 36, 37 and 38; and the three heavy chain CDRs comprising the sequences SEQ ID NOs. 39, 40 and 41, said hybridoma being filed at the CNCM, Pasteur Institute, Paris, France, on 28 Jul. 2011, under number 1-4499.

According to another aspect, the invention relates to a murine hybridoma capable of secreting an antibody comprising the three light chain CDRs comprising the sequences SEQ ID NOs. 64, 65 and 66; and the three heavy chain CDRs comprising the sequences SEQ ID NOs. 67, 68 and 69, said hybridoma being filed at the CNCM, Pasteur Institute, Paris, France, on 28 Jul. 2011, under number 1-4501.

Said hybridoma were obtained by the fusion of Balb/C immunized mice splenocytes/lymphocytes and cells of the myeloma Sp 2/O-Ag 14 cell line.

An object of the invention is a murine hybridoma selected from:

a) the murine hybridoma I-3959 deposited at the CNCM, Institut Pasteur, France, on the 2 Apr. 2008;

b) the murine hybridoma I-4499 deposited at the CNCM, Institut Pasteur, France, on the 28 Jul. 2011;

c) the murine hybridoma I-4501 deposited at the CNCM, Institut Pasteur, France, on the 28 Jul. 2011.

The antigen binding protein of the invention also comprises chimeric or humanized antibodies.

A chimeric antibody is one containing a natural variable region (light chain and heavy chain) derived from an antibody of a given species in combination with constant regions of the light chain and the heavy chain of an antibody of a species heterologous to said given species.

The antibodies, or chimeric fragments of same, can be prepared by using the techniques of recombinant genetics. For example, the chimeric antibody could be produced by cloning recombinant DNA containing a promoter and a sequence coding for the variable region of a nonhuman monoclonal antibody of the invention, notably murine, and a sequence coding for the human antibody constant region. A chimeric antibody according to the invention coded by one such recombinant gene could be, for example, a mouse-human chimera, the specificity of this antibody being determined by the variable region derived from the murine DNA and its isotype determined by the constant region derived from human DNA. Refer to Verhoeyn et al. (BioEssays, 8:74, 1988) for methods for preparing chimeric antibodies.

In another aspect, the invention describes a binding protein which consists of a chimeric antibody.

In a particular preferred embodiment, the chimeric antibody, or an antigen binding fragment of same, of the invention is selected in the group consisting of:

a) an antibody comprising a light chain variable domain sequence comprising the amino acid sequence SEQ ID NO. 7, and in that it comprises a heavy chain variable domain sequence comprising the amino acid sequence SEQ ID NO. 8;

b) an antibody comprising a light chain variable domain sequence comprising the amino acid sequence SEQ ID NO. 42, and in that it comprises a heavy chain variable domain sequence comprising the amino acid sequence SEQ ID NO. 43;

c) an antibody comprising a light chain variable domain sequence comprising the amino acid sequence SEQ ID NO. 70, and in that it comprises a heavy chain variable domain sequence comprising the amino acid sequence SEQ ID NO. 71.

In another aspect, the invention describes a binding protein which consists of a humanized antibody.

"Humanized antibodies" means an antibody that contains CDR regions derived from an antibody of nonhuman origin, the other parts of the antibody molecule being derived from one (or several) human antibodies. In addition, some of the skeleton segment residues (called FR) can be modified to preserve binding affinity (Jones et al., Nature, 321:522-525, 1986; Verhoeyen et al., Science, 239:1534-1536, 1988; Riechmann et al., Nature, 332:323-327, 1988).

The humanized antibodies of the invention or fragments of same can be prepared by techniques known to a person skilled in the art (such as, for example, those described in the documents Singer et al., J. Immun., 150:2844-2857, 1992; Mountain et al., Biotechnol. Genet. Eng. Rev., 10:1-142, 1992; and Bebbington et al., Bio/Technology, 10:169-175, 1992). Such humanized antibodies are preferred for their use in methods involving in vitro diagnoses or preventive and/or therapeutic treatment in vivo. Other humanization techniques, also known to a person skilled in the art, such as, for example, the "CDR grafting" technique described by PDL in patents EP 0 451 261, EP 0 682 040, EP 0 939 127, EP 0 566 647 or U.S. Pat. Nos. 5,530,101, 6,180,370, 5,585,089 and 5,693,761. U.S. Pat. Nos. 5,639,641 or 6,054,297, 5,886,152 and 5,877,293 can also be cited.

In addition, the invention also relates to humanized antibodies arising from the murine antibodies described above.

In a preferred manner, constant regions of the light-chain and the heavy-chain derived from human antibody are, respectively, the lambda or kappa and the gamma-1, gamma-2 or gamma-4 region.

A novel aspect of the present invention relates to an isolated nucleic acid characterized in that it is selected among the following nucleic acids (including any degenerate genetic code):

a) a nucleic acid coding for an antigen binding protein, or for an antigen binding fragment of same, according to the invention;

b) a nucleic acid comprising:

a nucleic acid sequence selected from the group consisting of SEQ ID NOs. 15 to 28, 50 to 63 and 78 to 91, or a nucleic acid sequence comprising the 6 nucleic acid sequences SEQ ID NOs.: 15 to 20 or 50 to 55 or 78 to 83, or a nucleic acid sequence comprising the two nucleic acid sequences SEQ ID NOs.: 21 and 22 or 56 and 57 or 84 and 85;

c) a nucleic acid complementary to a nucleic acid as defined in a) or b); and d) a nucleic acid, preferably having at least 18 nucleotides, capable of hybridizing under highly stringent conditions with a nucleic acid sequence as defined in part a) or b), or with a sequence with at least 80%, preferably 85%, 90%, 95% and 98% identity after optimal alignment with a nucleic acid sequence as defined in part a) or b).

Tables 4a-4c below summarize the various nucleotide sequences concerning the binding protein of the invention.

TABLE 4a

| | CDR numbering | Heavy chain | Light chain | SEQ ID NO. |
|---|---|---|---|---|
| 110D7 | IMGT | | CDR-L1 | 15 |
| | | | CDR-L2 | 16 |
| | | | CDR-L3 | 17 |
| | | CDR-H1 | | 18 |
| | | CDR-H2 | | 19 |
| | | CDR-H3 | | 20 |
| | Kabat | | CDR-L1 | 23 |
| | | | CDR-L2 | 24 |
| | | | CDR-L3 | 25 |
| | | CDR-H1 | | 26 |
| | | CDR-H2 | | 27 |
| | | CDR-H3 | | 28 |
| | | | variable domain | 21 |
| | | variable domain | | 22 |

TABLE 4b

| 1003A2 | IMGT | | CDR-L1 | 50 |
|---|---|---|---|---|
| | | | CDR-L2 | 51 |
| | | | CDR-L3 | 52 |
| | | CDR-H1 | | 53 |
| | | CDR-H2 | | 54 |
| | | CDR-H3 | | 55 |
| | Kabat | | CDR-L1 | 58 |
| | | | CDR-L2 | 59 |
| | | | CDR-L3 | 60 |
| | | CDR-H1 | | 61 |
| | | CDR-H2 | | 62 |
| | | CDR-H3 | | 63 |
| | | | variable domain | 56 |
| | | variable domain | | 57 |

TABLE 4c

| 1024G11 | IMGT | | CDR-L1 | 78 |
|---|---|---|---|---|
| | | | CDR-L2 | 79 |
| | | | CDR-L3 | 80 |
| | | CDR-H1 | | 81 |
| | | CDR-H2 | | 82 |
| | | CDR-H3 | | 83 |
| | Kabat | | CDR-L1 | 86 |
| | | | CDR-L2 | 87 |
| | | | CDR-L3 | 88 |
| | | CDR-H1 | | 89 |
| | | CDR-H2 | | 90 |
| | | CDR-H3 | | 91 |
| | | | variable domain | 84 |
| | | variable domain | | 85 |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

The sequences of the present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

"Nucleic sequences exhibiting a percentage identity of at least 80%, preferably 85%, 90%, 95% and 98%, after optimal alignment with a preferred sequence" means nucleic sequences exhibiting, with respect to the reference nucleic sequence, certain modifications such as, in particular, a deletion, a truncation, an extension, a chimeric fusion and/or a substitution, notably punctual. Preferably, these are sequences which code for the same amino acid sequences as the reference sequence, this being related to the degeneration of the genetic code, or complementarity sequences that are likely to hybridize specifically with the reference sequences, preferably under highly stringent conditions, notably those defined below.

Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10×Denhardt's, 5% dextran sulfate and 1% salmon sperm DNA; (2) primary hybridization for 20 hours at a temperature depending on the length of the probe (i.e.: 42° C. for a probe >100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe >100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

The invention also relates to a vector comprising a nucleic acid as described in the invention.

The invention notably targets cloning and/or expression vectors that contain such a nucleotide sequence.

The vectors of the invention preferably contain elements which allow the expression and/or the secretion of nucleotide sequences in a given host cell. The vector thus must contain a promoter, translation initiation and termination signals, as well as suitable transcription regulation regions. It must be able to be maintained in a stable manner in the host cell and may optionally have specific signals which specify secretion of the translated protein. These various elements are selected and optimized by a person skilled in the art according to the host cell used. For this purpose, the nucleotide sequences can be inserted in self-replicating vectors within the chosen host or be integrative vectors of the chosen host.

Such vectors are prepared by methods typically used by a person skilled in the art and the resulting clones can be introduced into a suitable host by standard methods such as lipofection, electroporation, heat shock or chemical methods.

The vectors are, for example, vectors of plasmid or viral origin. They are used to transform host cells in order to clone or express the nucleotide sequences of the invention.

The invention also comprises isolated host cells transformed by or comprising a vector as described in the present invention.

The host cell can be selected among prokaryotic or eukaryotic systems such as bacterial cells, for example, but also yeast cells or animal cells, notably mammal cells (with the exception of human). Insect or plant cells can also be used.

The invention also relates to animals, other than human, that have a transformed cell according to the invention.

Another aspect of the invention relates to a method for the production of an antigen binding protein according to the invention, or an antigen binding fragment thereof, characterized in that said method comprises the following steps:

a) the culture in a medium with the suitable culture conditions for a host cell according to the invention; and b) the recovery of the antigen binding protein, or one of its antigen binding fragments, thus produced from the culture medium or from said cultured cells.

The transformed cells according to the invention are of use in methods for the preparation of recombinant antigen binding proteins according to the invention. Methods for the preparation of antigen binding proteins according to the invention in recombinant form, characterized in that said methods use a vector and/or a cell transformed by a vector according to the invention, are also comprised in the present invention. Preferably, a cell transformed by a vector according to the invention is cultured under conditions that allow the expression of the aforesaid antigen binding protein and recovery of said recombinant protein.

As already mentioned, the host cell can be selected among prokaryotic or eukaryotic systems. In particular, it is possible to identify the nucleotide sequences of the invention that facilitate secretion in such a prokaryotic or eukaryotic system. A vector according to the invention carrying such a sequence can thus be used advantageously for the production of recombinant proteins to be secreted. Indeed, the purification of these recombinant proteins of interest will be facilitated by the fact that they are present in the supernatant of the cellular culture rather than inside host cells.

The antigen binding protein of the invention can also be prepared by chemical synthesis. One such method of preparation is also an object of the invention. A person skilled in the art knows methods for chemical synthesis, such as solid-phase techniques (see notably Steward et al., 1984, Solid phase peptides synthesis, Pierce Chem. Company, Rockford, 111, 2nd ed., pp 71-95) or partial solid-phase techniques, by condensation of fragments or by conventional synthesis in solution. Polypeptides obtained by chemical synthesis and capable of containing corresponding unnatural amino acids are also comprised in the invention.

The antigen binding protein, or the antigen binding fragments of same, likely to be obtained by the method of the invention are also comprised in the present invention.

According to a particular aspect, the invention concerns an antigen binding protein, or an antigen binding fragment thereof, as above described for use as an addressing product for delivering a cytotoxic agent at a host target site, said host target site consisting of an epitope localized into the protein Axl extracellular domain, preferably the human protein Axl extracellular domain, more preferably the human protein Axl extracellular domain having the sequence SEQ ID NO. 31 or 32, or natural variant sequence thereof.

In a preferred embodiment, said host target site is a target site of a mammalian cell, more preferably of a human cell, more preferably cells which naturally or by way of genetical recombination, express the Axl protein.

The invention relates to an immunoconjugate comprising the antigen binding protein as described in the present specification conjugated to a cytotoxic agent.

In the sense of the present invention, the expression "immunoconjugate" or "immuno-conjugate" refers generally to a compound comprising at least an addressing product physically linked with a one or more therapeutic agent(s), thus creating a highly targeted compound.

In a preferred embodiment, such therapeutic agents consist of cytotoxic agents.

By "cytotoxic agent" or "cytotoxic", it is intended an agent which, when administered to a subject, treats or prevents the development of cell proliferation, preferably the development of cancer in the subject's body, by inhibiting or preventing a cellular function and/or causing cell death.

Many cytotoxic agents have been isolated or synthesized and make it possible to inhibit the cells proliferation, or to destroy or reduce, if not definitively, at least significantly the tumour cells. However, the toxic activity of these agents is not limited to tumour cells, and the non-tumour cells are also effected and can be destroyed. More particularly, side effects are observed on rapidly renewing cells, such as haematopoietic cells or cells of the epithelium, in particular of the mucous membranes. By way of illustration, the cells of the gastrointestinal tract are largely effected by the use of such cytotoxic agents.

One of the aims of the present invention is also to be able to provide a cytotoxic agent which makes it possible to limit the side effects on normal cells while at the same time conserving a high cytotoxicity on tumour cells.

More particularly, the cytotoxic agent may preferably consist of, without limitation, a drug (i.e "antibody-drug conjugate"), a toxin (i.e. "immunotoxin" or "antibody-toxin conjugate"), a radioisotope (i.e. "radioimmunoconjugate" or "antibody-radioisotope conjugate"), etc.

In a first preferred embodiment of the invention, the immunoconjugate consists of a binding protein linked to at least a drug or a medicament. Such an immunoconjugate is referred as an antibody-drug conjugate (or "ADC") when the binding protein is an antibody, or an antigen binding fragment thereof.

In a first embodiment, such drugs can be described regarding their mode of action. As non limitative example, it can be mentioned alkylating agents such as nitrogen mustard, alkyle-sulfonates, nitrosourea, oxazophorins, aziridines or imine-ethylenes, anti-metabolites, anti-tumor antibiotics, mitotic inhibitors, chromatin function inhibitors, anti-angiogenesis agents, anti-estrogens, anti-androgens, chelating agents, Iron absorption stimulant, Cyclooxygenase inhibitors, Phosphodiesterase inhibitors, DNA inhibitors, DNA synthetic inhibitors, Apopstotis stimulants, Thymidylate inhibitors, T cell inhibitors, Interferon agonists, Ribonucleoside triphosphate reductase inhibitors, Aromatase inhibitors, Estrogen receptor antagonists, Tyrosine kinase inhibitors, Cell cycle inhibitors, Taxane, Tubulin inhibitors, angiogenesis inhibitors, macrophage stimulants, Neurokinin receptor antagonists, Cannabinoid receptor agonists, Dopamine receptor agosists, granulocytes stimulating factor agonists, Erythropoietin receptor agonists, somatostatin receptor agonists, LHRH agonists, Calcium sensitizers, VEGF receptor antagonists, interleukin receptor antagonists, osteoclast inhibitors, radical formation stimulants, endothelin receptor antagonists, Vinca alkaloid, anti-hormone or immunomodulators or any other new drug that fullfills the activity criteria of a cytotoxic or a toxin.

Such drugs are, for example, cited in the VIDAL 2010, on the page devoted to the compounds attached to the cancerology and hematology column "Cytotoxics", these cytotoxic compounds cited with reference to this document are cited here as preferred cytotoxic agents.

More particularly, without limitation, the following drugs are preferred according to the invention: mechlorethamine, chlorambucol, melphalen, chlorydrate, pipobromen, prednimustin, disodic-phosphate, estramustine, cyclophosphamide, altretamine, trofosfamide, sulfofosfamide, ifosfamide, thiotepa, triethylenamine, altetramine, carmustine, streptozocin, fotemustin, lomustine, busulfan, treosulfan, improsulfan, dacarbazine, cis-platinum, oxaliplatin, lobaplatin, heptaplatin, miriplatin hydrate, carboplatin, methotrexate, pemetrexed, 5-fluoruracil, floxuridine, 5-fluorodeoxyuridine, capecitabine, cytarabine, fludarabine, cytosine arabinoside, 6-mercaptopurine (6-MP), nelarabine, 6-thioguanine (6-TG), chlorodesoxyadenosine, 5-azacytidine, gemcitabine, cladribine, deoxycoformycin, tegafur, pentostatin, doxorubicin, daunorubicin, idarubicin, valrubicin, mitoxantrone, dactinomycin, mithramycin, plicamycin, mitomycin C, bleomycin, procarbazine, paclitaxel, docetaxel, vinblastine, vincristine, vindesine, vinorelbine, topotecan, irinotecan, etoposide, valrubicin, amrubicin hydrochloride, pirarubicin, elliptinium acetate, zorubicin, epirubicin, idarubicin and teniposide, razoxin, marimastat, batimastat, prinomastat, tanomastat, ilomastat, CGS-27023A, halofuginon, COL-3, neovastat, thalidomide, CDC 501, DMXAA, L-651582, squalamine, endostatin, SU5416, SU6668, interferon-alpha, EMD121974, interleukin-12, IM862, angiostatin, tamoxifen, toremifene, raloxifene, droloxifene, iodoxyfene, anastrozole, letrozole, exemestane, flutamide, nilutamide, sprironolactone, cyproterone acetate, finasteride, cimitidine, bortezomid, Velcade, bicalutamide, cyproterone, flutamide, fulvestran, exemestane, dasatinib, erlotinib, gefitinib, imatinib, lapatinib, nilotinib, sorafenib, sunitinib, retinoid, rexinoid, methoxsalene, methylaminolevulinate, aldesleukine, OCT-43, denileukin diflitox, interleukin-2, tasonermine, lentinan, sizofilan, roquinimex, pidotimod, pegademase, thymopentine, poly I:C, procodazol, Tic BCG, *corynebacterium parvum*, NOV-002, ukrain, levamisole, 1311-chTNT, H-101, celmoleukin, interferon alfa2a, interferon alfa2b, interferon gamma 1a, interleukin-2, mobenakin, Rexin-G, teceleukin, aclarubicin, actinomycin, arglabin, asparaginase, carzinophilin, chromomycin, daunomycin, leucovorin, masoprocol, neocarzinostatin, peplomycin, sarkomycin, so lamargine, trabectedin, streptozocin, testosterone, kunecatechins, sinecatechins, alitretinoin, belotecan hydrocholoride, calusterone, dromostano lone, elliptinium acetate, ethinyl estradiol, etoposide, fluoxymesterone, formestane, fosfetrol, goserelin acetate, hexyl amino levulinate, histrelin, hydroxyprogesterone, ixabepilone, leuprolide, medroxyprogesterone acetate, megesterol acetate, methylprediso lone, methyltestosterone, miltefosine, mitobronitol, nadro lone phenylpropionate, norethindrone acetate, predniso lone, prednisone, temsirrolimus, testolactone, triamconolone, triptorelin, vapreotide acetate, zinostatin stimalamer, amsacrine, arsenic trioxide, bisantrene hydrochloride, chlorambucil, chlortrianisene, cis-diamminedichloroplatinium, cyclophosphamide, diethylstilbestrol, hexamethylmelamine, hydroxyurea, lenalidomide, lonidamine, mechlorethanamine, mitotane, nedaplatin, nimustine hydrochloride, pamidronate, pipobroman, porfimer sodium, ranimustine, razoxane, semustine, sobuzoxane, mesylate, triethylenemelamine, zoledronic acid, camostat mesylate, fadrozole HCl, nafoxidine, aminoglutethimide, carmofur, clofarabine, cytosine arabinoside, decitabine, doxifluridine, enocitabine, fludarabne phosphate, fluorouracil, ftorafur, uracil mustard, abarelix, bexarotene, raltiterxed, tamibarotene, temozolomide, vorinostat, megastrol, clodronate disodium, levamisole, ferumoxytol, iron isomaltoside, celecoxib, ibudilast, bendamustine, altretamine, mitolactol, temsirolimus, pralatrexate, TS-1, decitabine, bicalutamide, flutamide, letrozole, clodronate disodium, degarelix, toremifene citrate, histamine dihydrochloride, DW-166HC, nitracrine, decitabine, irinoteacn hydrochloride, amsacrine, romidepsin, tretinoin, cabazitaxel, vandetanib, lenalidomide, ibandronic acid, miltefosine, vitespen, mifamurtide, nadroparin, granisetron, ondansetron, tropisetron, alizapride, ramosetron, dolasetron mesilate, fosaprepitant dimeglumine, nabilone, aprepitant, dronabinol, TY-10721, lisuride hydrogen maleate, epiceram, defibrotide, dabigatran etexilate, filgrastim, pegfilgrastim, reditux, epoetin, molgramostim, oprelvekin, sipuleucel-T, M-Vax, acetyl L-carnitine, donepezil hydrochloride, 5-aminolevulinic acid, methyl aminolevulinate, cetrorelix acetate, icodextrin, leuprorelin, metbylphenidate, octreotide, amlexanox, plerixafor, menatetrenone, anethole dithiolethione, doxercalciferol, cinacalcet hydrochloride, alefacept, romiplostim, thymoglobulin, thymalfasin, ubenimex, imiquimod, everolimus, sirolimus, H-101, lasofoxifene, trilostane, incadronate, gangliosides, pegaptanib octasodium, vertoporfin, minodronic acid, zoledronic acid, gallium nitrate, alendronate sodium, etidronate disodium, disodium pamidronate, dutasteride, sodium stibogluconate, armodafinil, dexrazoxane, amifostine, WF-10, temoporfin, darbepoetin alfa, ancestim, sargramostim, palifermin, R-744, nepidermin, oprelvekin, denileukin diftitox, crisantaspase, buserelin, deslorelin, lanreotide, octreotide, pilocarpine, bosentan, calicheamicin, maytansinoids and ciclonicate.

For more detail, the person skilled in the art could refer to the manual edited by the "Association Franøaise des Enseignants de Chimie Thérapeutique" and entitled "traité de chimie thérapeutique, vol. 6, Médicaments antitumoraux et perspectives dans le traitement des cancers, edition TEC & DOC, 2003".

In a second preferred embodiment of the invention, the immunoconjugate consists of a binding protein linked to at least a radioisotope. Such an immunoconjugate is referred as an antibody-radioisotope conjugate (or "ARC") when the binding protein is an antibody, or an antigen binding fragment thereof.

For selective destruction of the tumor, the antibody may comprise a highly radioactive atom. A variety of radioactive isotopes are available for the production of ARC such as, without limitation $At^{211}$, $C^{13}$, $N^{15}$, $O^{17}$, $Fl^{19}$, $I^{123}$, $I^{131}$, $I^{125}$, $In^{111}$, $Y^{90}$, $Re^{186}$, $Re^{188}$, $Sm^{153}$, $tc^{99m}$, $Bi^{212}$, $P^{32}$, $Pb^{212}$, radioactive isotopes of Lu, gadolinium, manganese or iron.

Any methods or processes known by the person skilled in the art can be used to incorporate such radioisotope in the ARC (see, for example "Monoclonal Antibodies in Immunoscintigraphy", Chatal, CRC Press 1989). As non limitative example, $tc^{99}m$ or $I^{123}$, $Re^{186}$, $Re^{188}$ and $In^{111}$ can be attached via a cysteine residue. $Y^{90}$ can be attached via a lysine residue. $I^{123}$ can be attached using the IODOGEN method (Fraker et al (1978) Biochem. Biophys. Res. Commun. 80: 49-57).

Several examples can be mentioned to illustrate the knowledge of the person skilled in the art in the field of ARC such as Zevalin® which is an ARC composed of an anti-CD20 monoclonal antibody and $In^{111}$ or $Y^{90}$ radioisotope bound by a thiourea linker-chelator (Wiseman et at (2000) Eur. Jour. Nucl. Med. 27(7):766-77; Wiseman et al (2002) Blood 99(12):4336-42; Witzig et at (2002) J. Clin. Oncol. 20(10):2453-63; Witzig et al (2002) J. Clin. Oncol. 20(15): 3262-69); or Mylotarg® which is composed of an anti-CD33 antibody linked to calicheamicin, (U.S. Pat. Nos. 4,970,198; 5,079,233; 5,585,089; 5,606,040; 5,693,762; 5,739,116; 5,767,285; 5,773,001). More recently, it can also be mentioned the ADC referred as Adcetris (corresponding to the Brentuximab vedotin) which has been recently accepted by the FDA in the treatment of Hodgkin's lymphoma (Nature, vol. 476, pp 380-381, 25 Aug. 2011).

In a third preferred embodiment of the invention, the immunoconjugate consists of a binding protein linked to at least a toxin. Such an immunoconjugate is referred as an antibody-toxin conjugate (or "ATC") when the binding protein is an antibody, or an antigen binding fragment thereof.

Toxins are effective and specific poisons produced by living organisms. They usually consist of an amino acid chain which can vary in molecular weight between a couple of hundred (peptides) and one hundred thousand (proteins). They may also be low-molecular organic compounds. Toxins are produced by numerous organisms, e.g., bacteria, fungi, algae and plants. Many of them are extremely poisonous, with a toxicity that is several orders of magnitude greater than the nerve agents.

Toxins used in ATC can include, without limitation, all kind of toxins which may exert their cytotoxic effects by mechanisms including tubulin binding, DNA binding, or topoisomerase inhibition.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

Small molecule toxins, such as dolastatins, auristatins, a trichothecene, and CC1065, and the derivatives of these toxins that have toxin activity, are also contemplated herein. Dolastatins and auristatins have been shown to interfere with microtubule dynamics, GTP hydrolysis, and nuclear and cellular division and have anticancer and antifungal activity.

"Linker", "Linker Unit", or "link" means a chemical moiety comprising a covalent bond or a chain of atoms that covalently attaches a binding protein to at least one cytotoxic agent.

Linkers may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of cyctotoxic agents to the addressing system. Other cross-linker reagents may be BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

The linker may be a "non cleavable" or "cleavable".

In a preferred embodiment, it consists in a "cleavable linker" facilitating release of the cytotoxic agent in the cell. For example, an acid-labile linker, peptidase-sensitive linker, photolabile linker, dimethyl linker or disulfide-containing linker may be used. The linker is, in a preferred embodiment, cleavable under intracellular conditions, such that cleavage of the linker releases the cytotoxic agent from the binding protein in the intracellular environment.

For example, in some embodiments, the linker is cleavable by a cleaving agent that is present in the intracellular environment (e.g., within a lysosome or endosome or caveolea). The linker can be, for example, a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). In specific embodiments, the peptidyl linker cleavable by an intracellular protease is a Val-Cit linker or a Phe-Lys linker. One advantage of using intracellular proteolytic release of the cytotoxic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT.

As non limitative example of non-cleavable or "non reductible" linkers, it can be mentioned the immunoconjugate Trastuzumab-DM1 (TDM1) which combines trastuzumab with a linked chemotherapy agent, maytansine (Cancer Research 2008; 68: (22). Nov. 15, 2008).

In a preferred embodiment, the immunoconjugate of the invention may be prepared by any method known by the person skilled in the art such as, without limitation, i) reaction of a nucleophilic group of the antigen binding protein with a bivalent linker reagent followed by reaction with the cytotoxic agent or ii) reaction of a nucleophilic group of a cytotoxic agent with a bivalent linker reagent followed by reaction with the nucleophilic group of the antigen binding protein.

Nucleophilic groups on antigen binding protein include, without limitation, N-terminal amine groups, side chain amine groups, e.g. lysine, side chain thiol groups, and sugar hydroxyl or amino groups when the antigen binding protein is glycosylated. Amine, thiol, and hydroxyl groups are nucleophilic and capable of reacting to form covalent bonds with electrophilic groups on linker moieties and linker reagents including, without limitation, active esters such as NHS esters, HOBt esters, haloformates, and acid halides; alkyl and benzyl halides such as haloacetamides; aldehydes, ketones, carboxyl, and maleimide groups. The antigen binding protein may have reducible interchain disulfides, i.e. cysteine bridges. The antigen binding proteins may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into the antigen binding protein through any reaction known by the person skilled in the art. As non limitative example, reactive thiol groups may be introduced into the antigen binding protein by introducing one or more cysteine residues.

Immunoconjugates may also be produced by modification of the antigen binding protein to introduce electrophilic moieties, which can react with nucleophilic substituents on the linker reagent or cytotoxic agent. The sugars of glycosylated antigen binding protein may be oxidized to form aldehyde or ketone groups which may react with the amine group of linker reagents or cytotoxic agent. The resulting imine Schiff base groups may form a stable linkage, or may be reduced to form stable amine linkages. In one embodiment, reaction of the carbohydrate portion of a glycosylated antigen binding protein with either galactose oxidase or sodium meta-periodate may yield carbonyl (aldehyde and ketone) groups in the protein that can react with appropriate groups on the drug. In another embodiment, proteins containing N-terminal serine or threonine residues can react with sodium meta-periodate, resulting in production of an aldehyde in place of the first amino acid.

In certain preferred embodiments, the linker unit may have the following general formula:

$$-T_a-W_w-Y_y-$$

wherein:
-T- is a stretcher unit;
a is 0 or 1;
-W- is an amino acid unit;
w is independently an integer ranging from 1 to 12;
-Y- is a spacer unit;
y is 0, 1 or 2.

The stretcher unit (-T-), when present, links the antigen binding protein to an amino acid unit (—W—). Useful functional groups that can be present on the antigen binding protein, either naturally or via chemical manipulation, include sulfhydryl, amino, hydroxyl, the anomeric hydroxyl group of a carbohydrate, and carboxyl. Suitable functional groups are sulfhydryl and amino. Sulfhydryl groups can be generated by reduction of the intramolecular disulfide bonds of the antigen binding protein, if present. Alternatively, sulfhydryl groups can be generated by reaction of an amino group of a lysine moiety of the antigen binding protein with 2-iminothiolane or other sulfhydryl generating reagents. In specific embodiments, the antigen binding protein is a recombinant antibody and is engineered to carry one or more lysines. More preferably, the antigen binding protein can be engineered to carry one or more Cysteines (cf. ThioMabs).

In certain specific embodiments, the stretcher unit forms a bond with a sulfur atom of the antigen binding protein. The sulfur atom can be derived from a sulfhydryl (—SH) group of a reduced antigen binding protein.

In certain other specific embodiments, the stretcher unit is linked to the antigen binding protein via a disulfide bond between a sulfur atom of the antigen binding protein and a sulfur atom of the stretcher unit.

In other specific embodiments, the reactive group of the stretcher contains a reactive site that can be reactive to an amino group of the antigen binding protein. The amino group can be that of an arginine or a lysine. Suitable amine reactive sites include, but are not limited to, activated esters such as succinimide esters, 4-nitrophenyl esters, pentafluorophenyl esters, anhydrides, acid chlorides, sulfonyl chlorides, isocyanates and isothiocyanates.

In yet another aspect, the reactive function of the stretcher contains a reactive site that is reactive to a modified carbohydrate group that can be present on the antigen binding protein. In a specific embodiment, the antigen binding protein is glycosylated enzymatically to provide a carbohydrate moiety (to be noticed that, when the antigen binding protein is an antibody, said antibody is generally naturally glycosylated). The carbohydrate may be mildly oxidized with a reagent such as sodium periodate and the resulting carbonyl unit of the oxidized carbohydrate can be condensed with a stretcher that contains a functionality such as a hydrazide, an oxime, a reactive amine, a hydrazine, a thiosemicarbazide, a hydrazine carboxylate, or an arylhydrazide.

The amino acid unit (-W-) links the stretcher unit (-T-) to the Spacer unit (-Y-) if the spacer unit is present, and links the stretcher unit to the cytotoxic agent if the spacer unit is absent.

As above mentioned, -Ww- may be a dipeptide, tripeptide, tetrapeptide, pentapeptide, hexapeptide, heptapeptide, octapeptide, nonapeptide, decapeptide, undecapeptide or dodecapeptide unit In some embodiments, the amino acid unit may comprise amino acid residues such as, without limitation, alanine, valine, leucine, isoleucine, methionine, phenylalanine, tryptophan, proline, lysine protected with acetyl or formyl, arginine, arginine protected with tosyl or nitro groups, histidine, ornithine, ornithine protected with acetyl or formyl and citrulline. Exemplary amino acid linker components include preferably a dipeptide, a tripeptide, a tetrapeptide or a pentapeptide.

Exemplary dipeptides include: Val-Cit, Ala-Val, Lys-Lys, Cit-Cit, Val-Lys, Ala-Phe, Phe-Lys, Ala-Lys, Phe-Cit, Leu-Cit, Ile-Cit, Trp-Cit, Phe-Ala, Phe-$N^9$-tosyl-Arg, Phe-$N^9$-Nitro-Arg.

Exemplary tripeptides include: Val-Ala-Val, Ala-Asn-Val, Val-Leu-Lys, Ala-Ala-Asn, Phe-Phe-Lys, Gly-Gly-Gly, D-Phe-Phe-Lys, Gly-Phe-Lys.

Exemplary tetrapeptide include: Gly-Phe-Leu-Gly (SEQ ID NO. 33), Ala-Leu-Ala-Leu (SEQ ID NO. 34).

Exemplary pentapeptide include: Pro-Val-Gly-Val-Val (SEQ ID NO. 35).

Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzyme, for example, a tumor-associated protease, cathepsin B, C and D, or a plasmin protease.

The amino acid unit of the linker can be enzymatically cleaved by an enzyme including, but not limited to, a tumor-associated protease to liberate the cytotoxic agent.

The amino acid unit can be designed and optimized in its selectivity for enzymatic cleavage by a particular tumor-associated protease. The suitable units are those whose cleavage is catalyzed by the proteases, cathepsin B, C and D, and plasmin.

The spacer unit (-Y-), when present, links an amino acid unit to the cytotoxic agent. Spacer units are of two general types: self-immolative and non self-immolative. A non self-immolative spacer unit is one in which part or all of the spacer unit remains bound to the cytotoxic agent after enzymatic cleavage of an amino acid unit from the immunoconjugate. Examples of a non self-immolative spacer unit include, but are not limited to a (glycine-glycine) spacer unit and a glycine spacer unit. To liberate the cytotoxic agent, an independent hydrolysis reaction should take place within the target cell to cleave the glycine-drug unit bond.

In another embodiment, a non self-immolative the spacer unit (-Y-) is -Gly-.

In one embodiment, the immunoconjugate lacks a spacer unit (y=0). Alternatively, an imunoconjugate containing a self-immolative spacer unit can release the cytotoxic agent without the need for a separate hydrolysis step. In these embodiments, -Y- is a p-aminobenzyl alcohol (PAB) unit that is linked to -Ww- via the nitrogen atom of the PAB group, and connected directly to -D via a carbonate, carbamate or ether group.

Other examples of self-immolative spacers include, but are not limited to, aromatic compounds that are electronically equivalent to the PAB group such as 2-aminoimidazol-5-methanol derivatives and ortho or para-aminobenzylacetals. Spacers can be used that undergo facile cyclization upon amide bond hydrolysis, such as substituted and unsubstituted 4-aminobutyric acid amides, appropriately substituted bicyclo[2.2.1] and bicyclo[2.2.2] ring systems and 2-aminophenylpropionic acid amides.

In an alternate embodiment, the spacer unit is a branched bis(hydroxymethyl)styrene (BHMS) unit, which can be used to incorporate additional cytotoxic agents.

Finally, the invention relates to an immunoconjugate as above described for use in the treatment of cancer.

Cancers can be preferably selected through Axl-related cancers including tumoral cells expressing or over-expressing whole or part of the protein Axl at their surface.

More particularly, said cancers are breast, colon, esophageal carcinoma, hepatocellular, gastric, glioma, lung, melanoma, osteosarcoma, ovarian, prostate, rhabdomyosarcoma, renal, thyroid, uterine endometrial cancer and any drug resistance phenomena. Another object of the invention is a pharmaceutical composition comprising the immunoconjugate as described in the specification.

More particularly, the invention relates to a pharmaceutical composition comprising the immunoconjugate of the invention with at least an excipient and/or a pharmaceutical acceptable vehicle.

In the present description, the expression "pharmaceutically acceptable vehicle" or "excipient" is intended to indicate a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles and excipients are well known and will be adapted by the person skilled in the art as a function of the nature and of the mode of administration of the active compound(s) chosen.

Preferably, these immunoconjugates will be administered by the systemic route, in particular by the intravenous route, by the intramuscular, intradermal, intraperitoneal or subcutaneous route, or by the oral route. In a more preferred manner, the composition comprising the immunoconjugates according to the invention will be administered several times, in a sequential manner.

Their modes of administration, dosages and optimum pharmaceutical forms can be determined according to the criteria generally taken into account in the establishment of a treatment adapted to a patient such as, for example, the age or the body weight of the patient, the seriousness of his/her general condition, the tolerance to the treatment and the secondary effects noted.

Other characteristics and advantages of the invention appear in the continuation of the description with the examples and the figures whose legends are represented below.

FIGURE LEGENDS

Figure 1B:
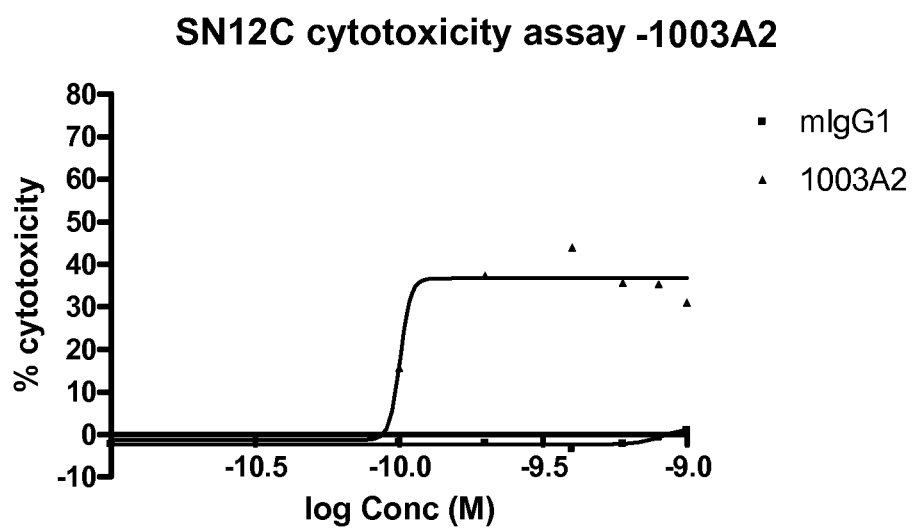
Figure 1C:
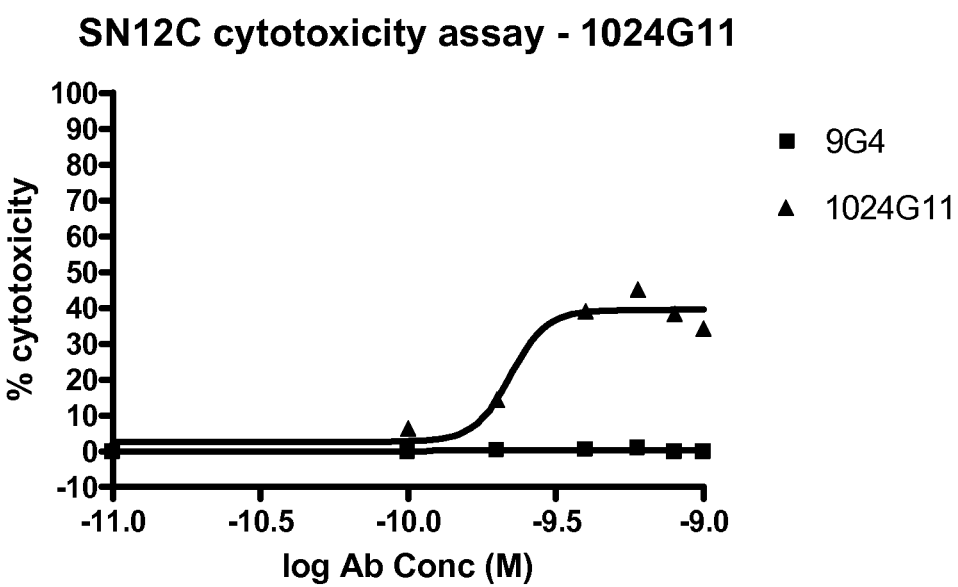

FIGS. 1A-C: in vitro cytotoxicity assay using Mab-zap conjugated secondary antibody on SN12C cells for 110D7 (A), 1003A2 (B) and 1024G11 (C).

FIGS. 2A-2I: Specificity of anti-Axl binding of:
  110D7 on the immobilized rhAxl-Fc protein (2A), rhDtk-Fc (2B) or rhMer-Fc (2C) proteins by ELISA,
  1003A2 on the immobilized rhAxl-Fc protein (2D), rhDtk-Fc (2E) or rhMer-Fc (2F) proteins by ELISA,
  1024G11 on the immobilized rhAxl-Fc protein (2G), rhDtk-Fc (2H) or rhMer-Fc (2I) proteins by ELISA.

Figure 3A:
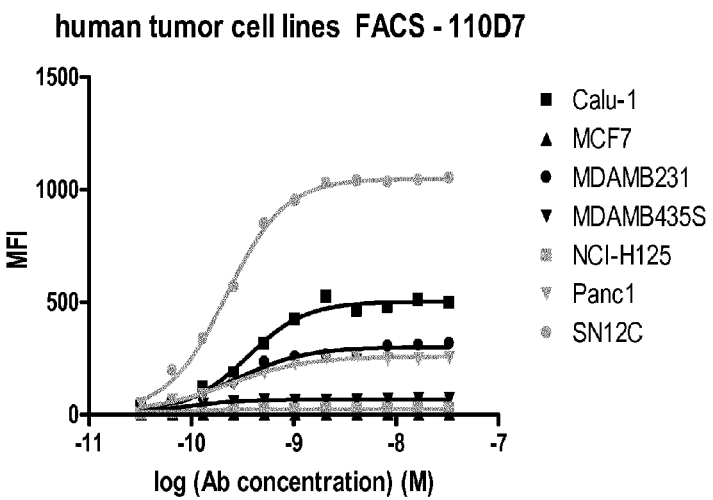
Figure 3B:
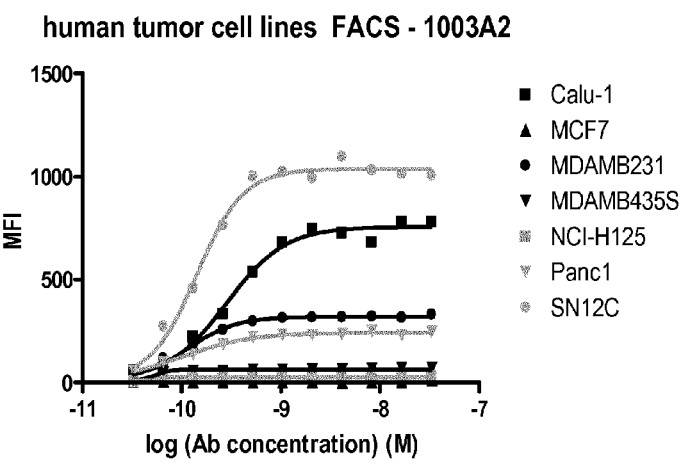
Figure 3C:
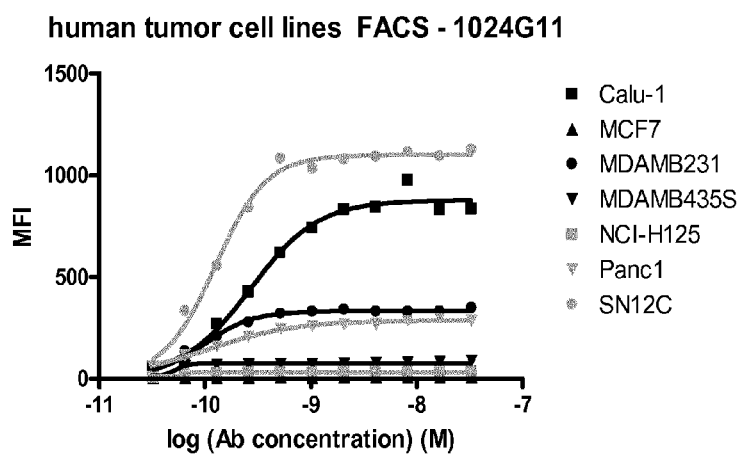

FIGS. 3A-C: 110D7 (A), 1003A2 (B) and 1024G11 (C) dose response data obtained by flow cytometry in presence of various human tumor cell lines (Calu-1, MCF7, MDA-MB-231, MDA-MB435S, NCI-H125, Panc1 and SN12C).

Figure 4A:
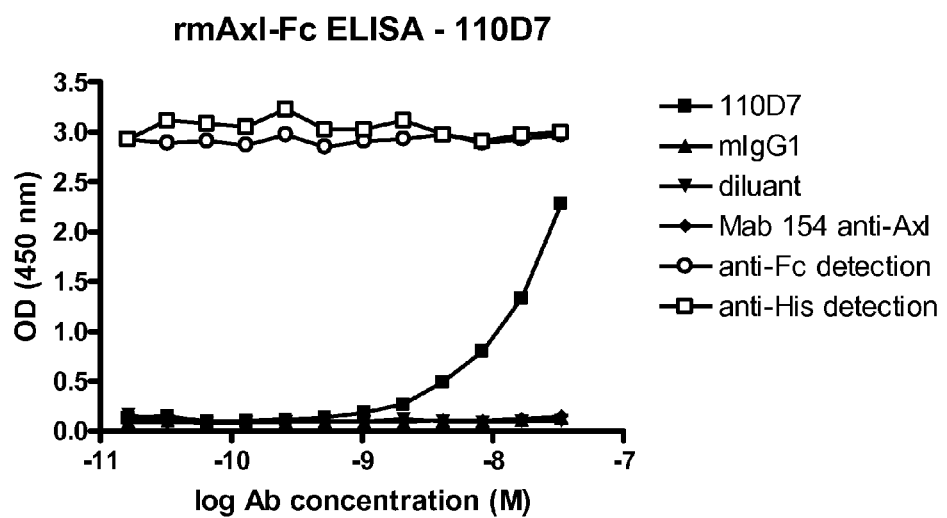
Figure 4B:
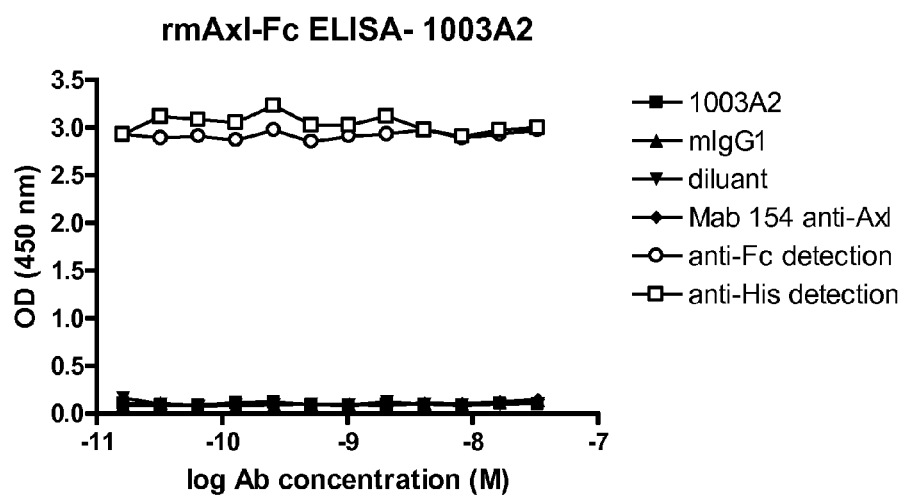
Figure 4C:
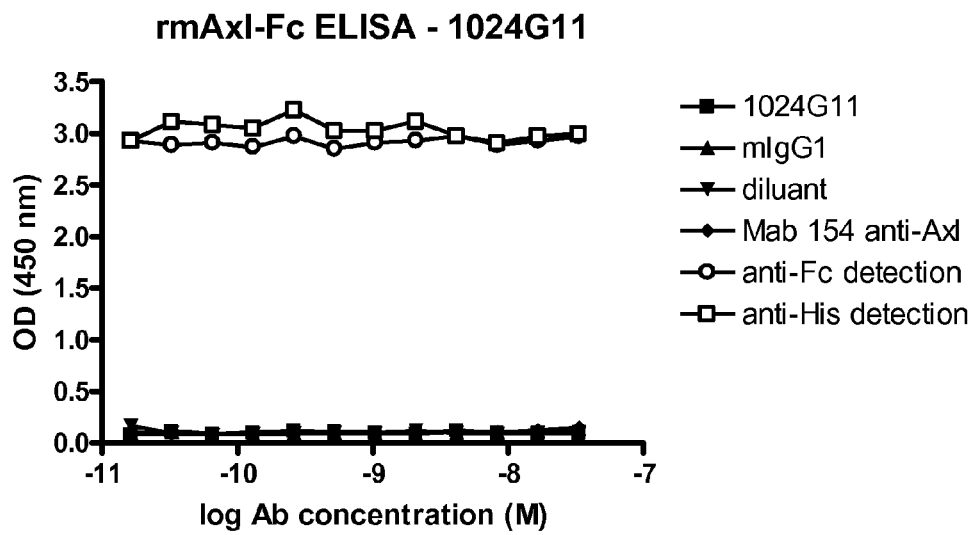

FIGS. 4A-C: ELISA on the immobilized rmAxl-Fc protein ("rm" for murine recombinant) for 110D7 (A), 1003A2 (B) and 1024G11 (C).

Figure 5A:
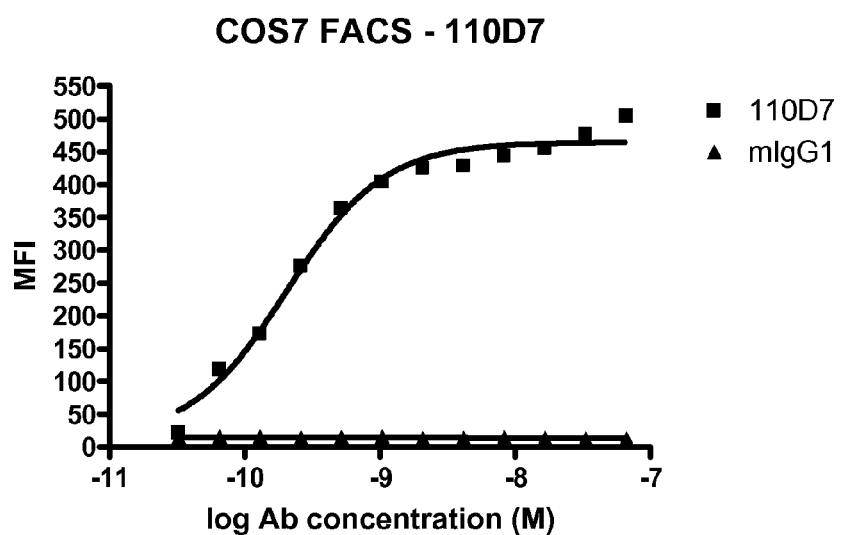
Figure 5B:
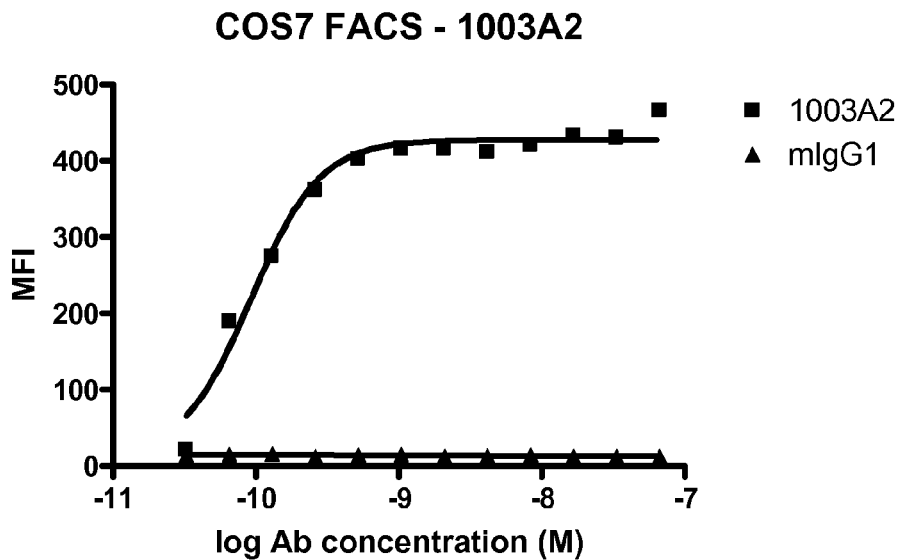
Figure 5C:
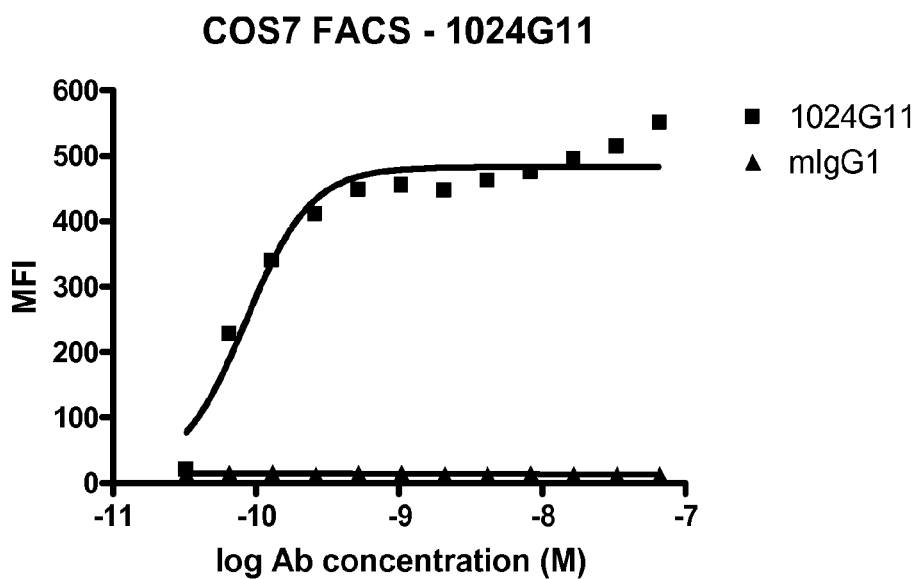

FIGS. 5A-C: 110D7 (A), 1003A2 (B) and 1024G11 (C) binding on COST cells as determined by indirect labelling protocol using flow cytometry method.

Figure 6A:
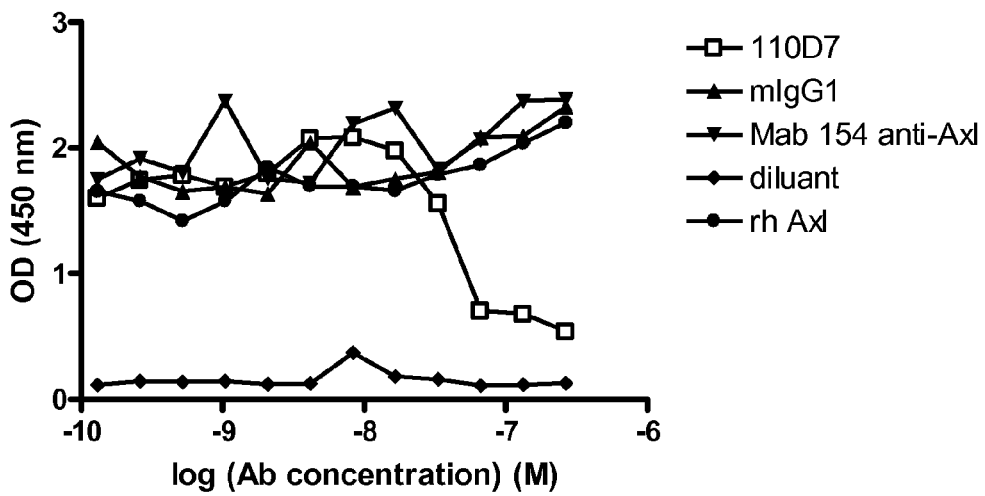
Figure 6B:
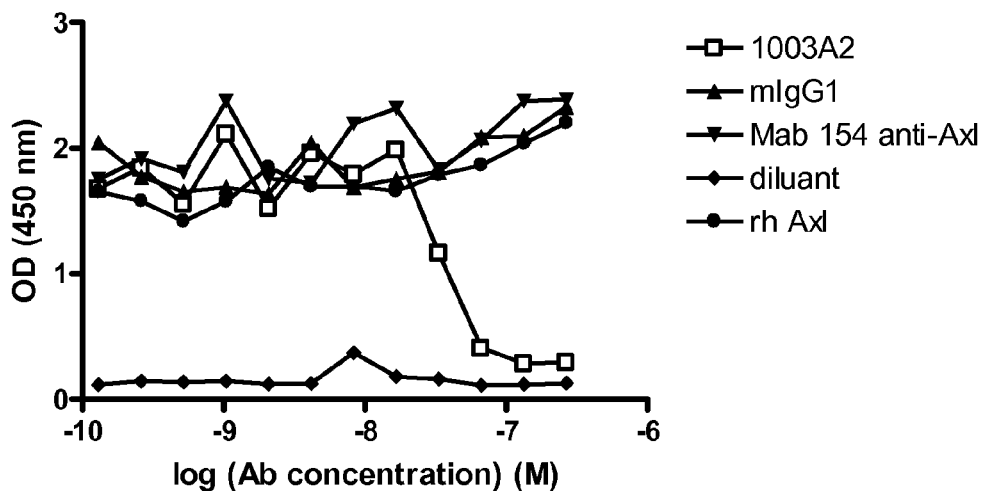
Figure 6C:
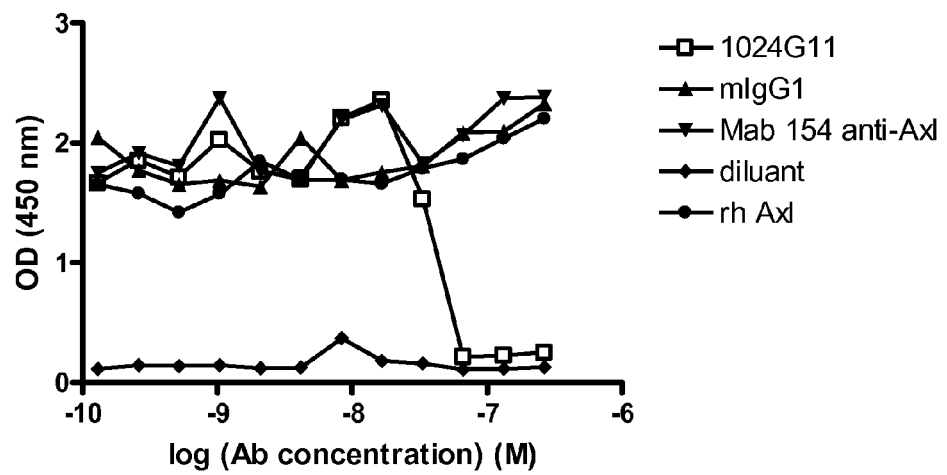

FIGS. 6A-C: Competition ELISA of Gas6 binding using anti-Axl antibodies 110D7 (A), 1003A2 (B) and 1024G11 (C).

Figure 7A:
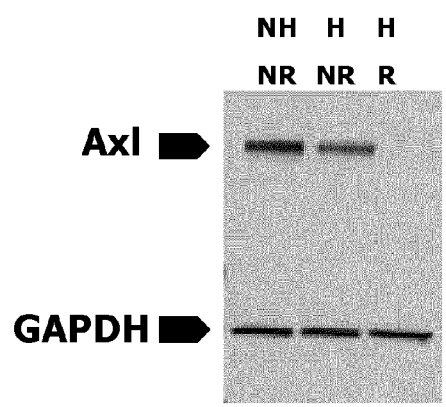
Figure 7B:
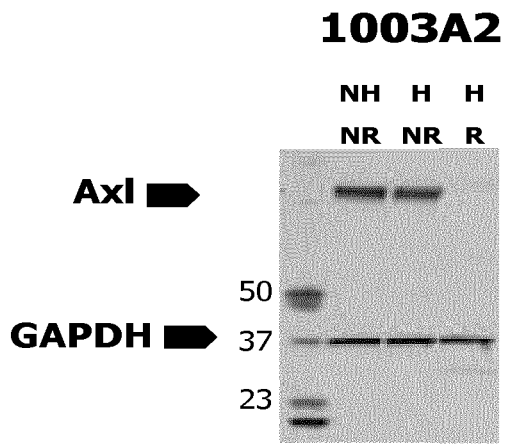
Figure 7C:
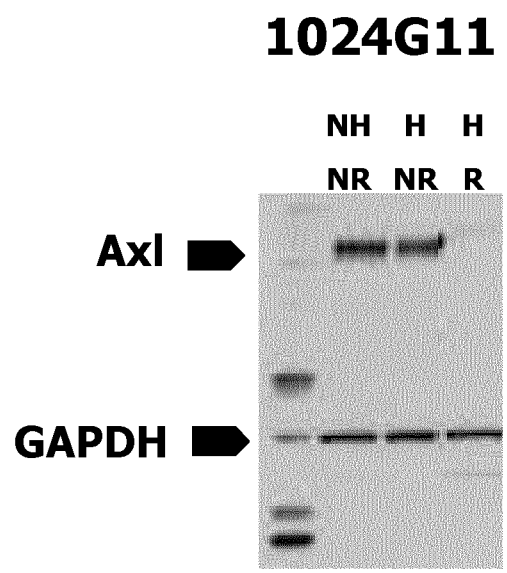

FIGS. 7A-C: Epitope binding analysis by western Blot using SN12C cell lysate for 110D7 (A), 1003A2 (B) and 1024G11 (C). NH (no heat); NR (no reduction); H (heat); R (reduction). GAPDH detection attests to the correct sample loading on the gel.

FIGS. 8A-F: Study of Axl downregulation after 110D7, 1003A2 and 1024G11 binding on SN12C cells by Western Blot with FIGS. 8A (110D7) 8C (1003A2) and 8E (1024G11)—Western blot image representative of the 3 independent experiments performed (The western blot analysis was performed after a 4 h and 24 h incubation of the anti-Axl antibody on SN12C cells); and FIGS. 8B (110D7), 8D (1003A2) and 8F (1024G11)—Optical density quantification of the presented film using "QuantityOne" software.

FIGS. 9A-I: Immunofluorescence microscopy of SN12C cells after incubation with the 110D7, 1003A2 and 1024G11 anti-Axl antibody FIGS. 9A (110D7), 9D (1003A2) and 9G (1024G11)—Photographs of the mIgG1 isotype control conditions both for the membrane and the intracellular staining FIGS. 9B (110D7), 9E (1003A2) and 9H (1024G11)—Membrane staining FIGS. 9C (110D7), 9F (1003A2) and 9I (1024G11)—Intracellular staining of both Axl receptor using the 110D7, respectively 1003A2 and 1024G11, antibodies and of the early endosome marker EEA1. Image overlays are presented bellow and co-localizations visualized are indicated by the arrows.

Figure 10A:
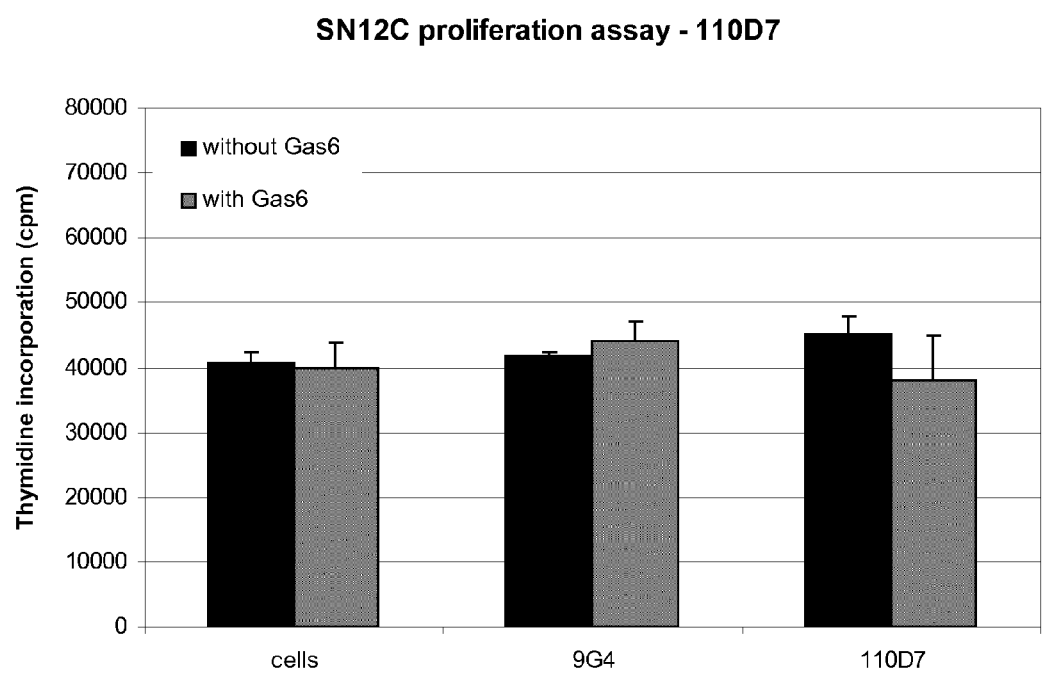
Figure 10B:
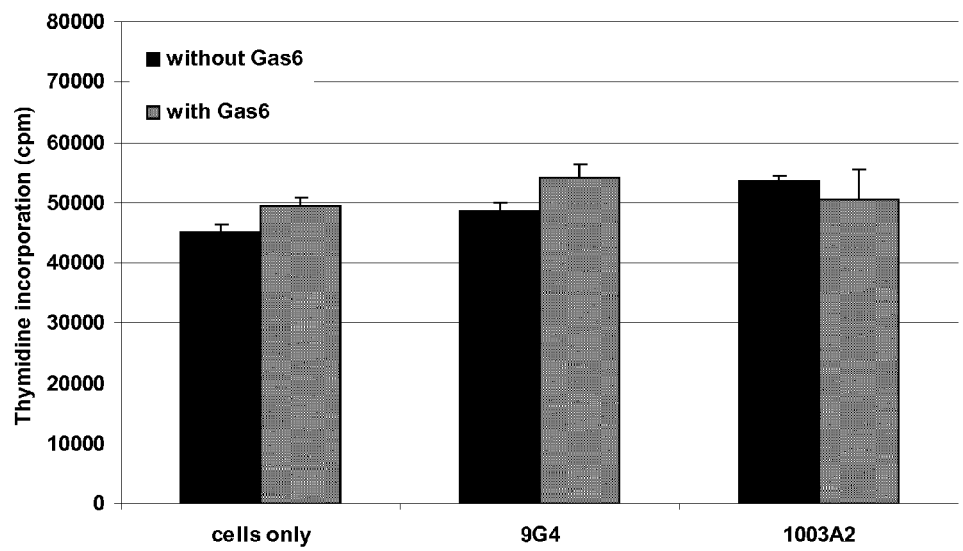
Figure 10C:
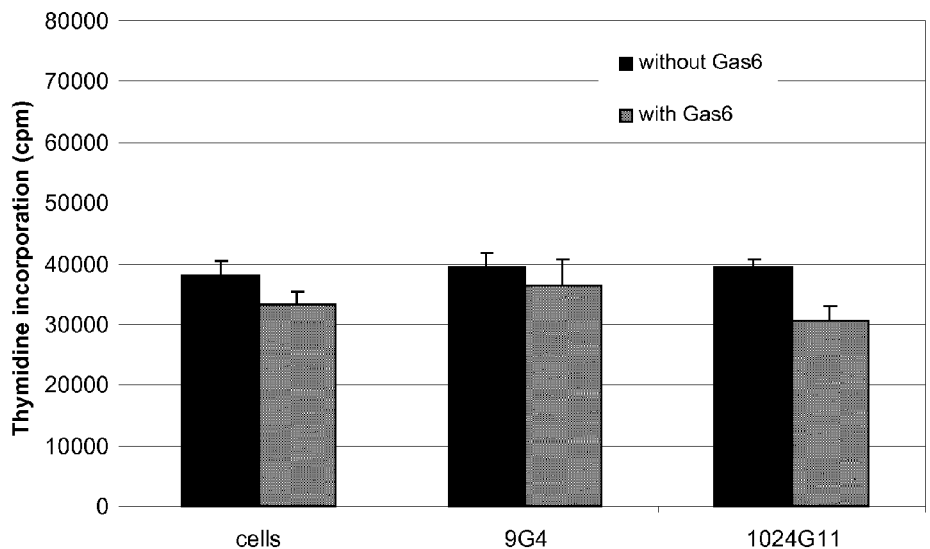
Figures 11A, 11B, 11C, 11D, 11E, 11F, 11G, 11H, 11I, 11J, 11K:
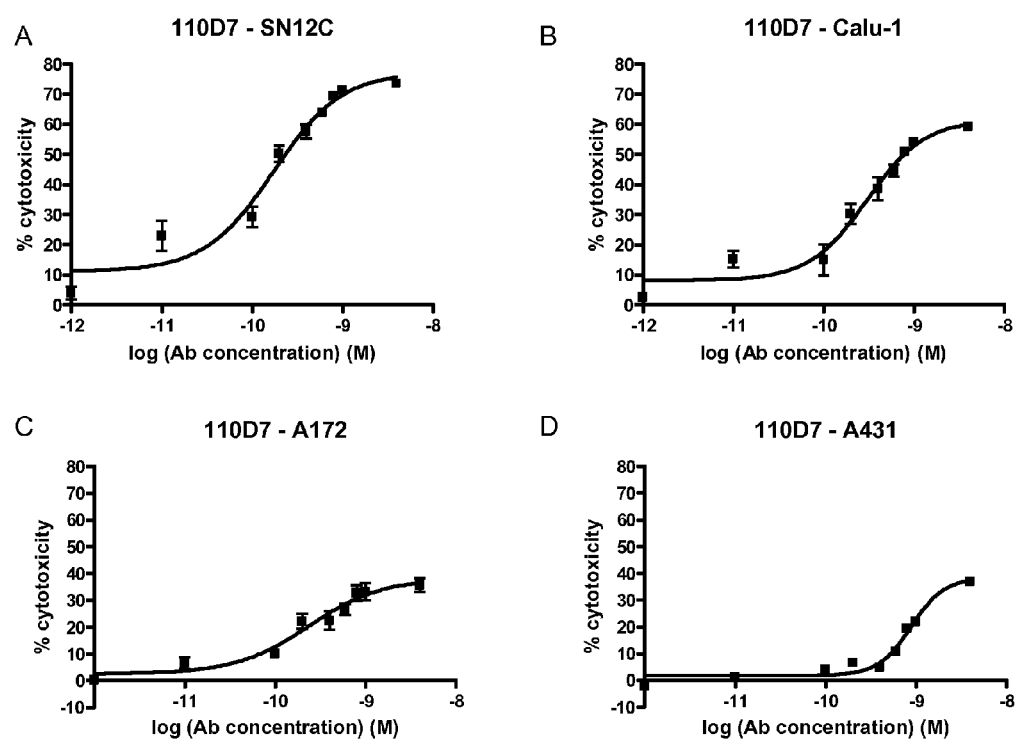
Figures 12A, 12B, 12C, 12D, 12E, 12F, 12G, 12H, 12I, 12J, 12K:
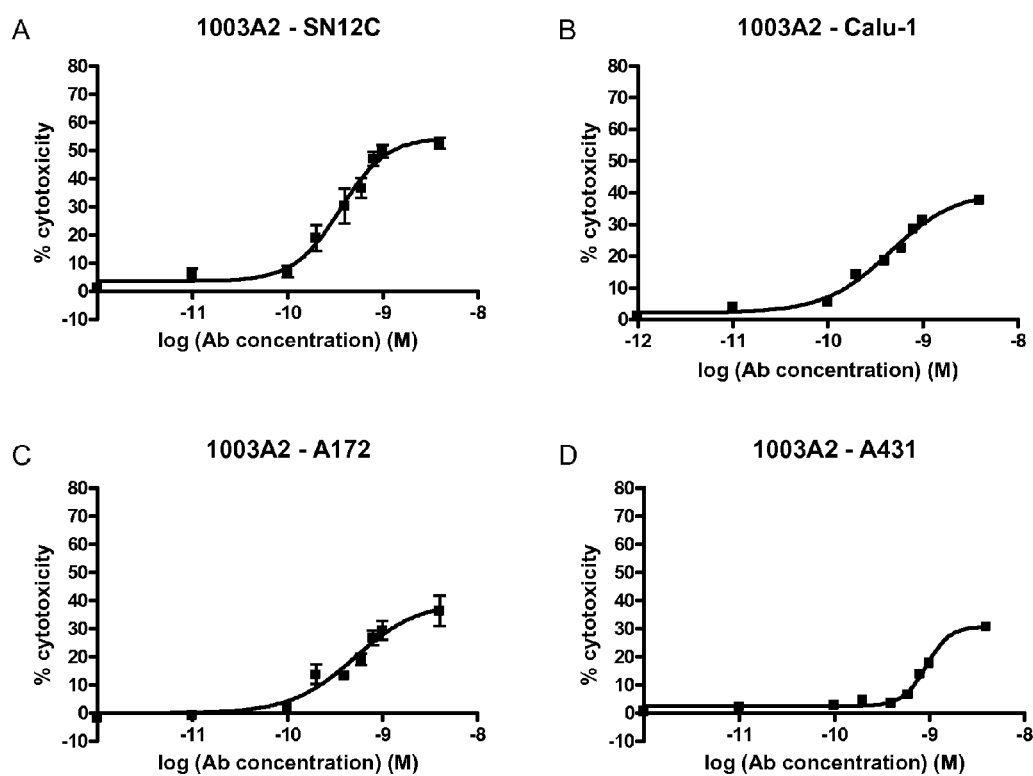
Figures 13A, 13B, 13C, 13D, 13E, 13F, 13G, 13H, 13I, 13J, 13K:
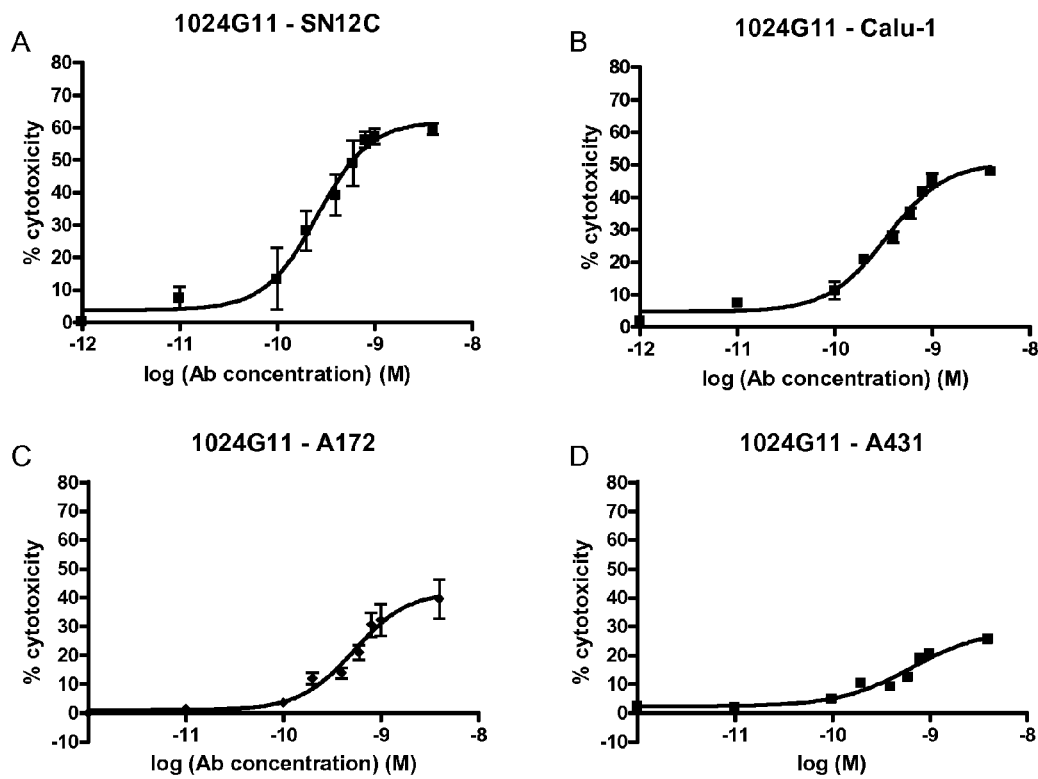

FIGS. 10A-C: Effect of the 110D7 (A), 1003A2 (B) and 1024G11 (C) antibodies on in vitro SN12C cells proliferation compared to the effect of a mIgG1 isotype control antibody.

FIGS. 11A-11K present cytotoxicity percentage in function of the 110D7 immunoconjugate concentration obtained in distinct in vitro cell cytotoxicity assays with (A) SN12C, (B) Calu-1, (C) A172, (D) A431, (E) DU145, (F) MDA-MB-4355, (G) MDA-MB-231, (H) PC3, (I) NCI-H226, (J) NCI-H125 or (K) Panc1 tumor cells treated with a range of 117D7-saporin immunoconjugate concentrations.

FIGS. 12A-12K present cytotoxicity percentage in function of the 1003A2 immunoconjugate concentration obtained in distinct in vitro cell cytotoxicity assays with (A) SN12C, (B) Calu-1, (C) A172, (D) A431, (E) DU145, (F) MDA-MB-435S, (G) MDA-MB-231, (H) PC3, (I) NCI-H226, (J) NCI-H125 or (K) Panc1 tumor cells treated with a range of 1003A2-saporin immunoconjugate concentrations.

FIGS. 13A-13K present cytotoxicity percentage in function of the 1024G11 immunoconjugate concentration obtained in distinct in vitro cell cytotoxicity assays with (A) SN12C, (B) Calu-1, (C) A172, (D) A431, (E) DU145, (F) MDA-MB-435S, (G) MDA-MB-231, (H) PC3, (I) NCI-H226, (J) NCI-H125 or (K) Panc1 tumor cells treated with a range of 1024G11-saporin immunoconjugate concentrations

EXAMPLES

In the following examples, isotype control antibody used consists of a murine IgG1 referred as 9G4. It means that, in the following examples, the expressions mIgG1, control and 9G4 are similar.

Example 1

Axl Receptor Internalization

As an immunoconjugate approach is more efficient when the targeted antigen is an internalizing protein, Axl receptor internalization using Mab-Zap cytotoxicity assay on human tumor cell lines was studied. More precisely, the Mab-Zap reagent is a chemical conjugate of affinity purified goat anti-mouse IgG and the ribosome-inactivating protein, saporin. If internalization of the immune complex occurs, saporin breaks away from the targeting agent and inactivates the ribosomes, which causes protein inhibition and, ultimately, cell death. Cell viability determination after 72 hours incubation with the antibodies on Axl-positive cells allows concluding on the Axl receptor internalization.

For this example highly Axl-positive cells, as determined using Qifikit reagent (Dako), were used. Data are presented in the following table 5.

TABLE 5

| Antigen binding capacity of the MAB154 anti-Axl commercial antibody determined for the human renal cancer SN12C cells | |
|---|---|
| RTK | AXL |
| Cell line\Antibody | MAB154 |
| SN12C | >100 000 |

In the following example, the SN12C cells were used as non limitative example. Any other cell line expressing appropriate level of Axl receptor on its cell surface could be used.

Concentration ranges of the 110D7, respectively 1003A2 and 1024G11 anti-Axl antibodies or the mIgG1 isotype control 9G4 antibody were pre-incubated with 100 ng of Mab-Zap (Advanced targeting systems) secondary antibody in cell culture medium for 30 min at RT. These mixtures were loaded on sub-confluent SN12C cells plated in white 96-well plate microplate. Plates were incubated for 72 h at 37° C. in presence of 5% $CO_2$. Cell viability was determined using a Cell Titer Glo cell proliferation method according to the manufacturer's instructions (Promega). Several controls are performed: conditions i) without any secondary immunoconjugate and ii) without primary antibody are prepared. In parallel, assays are performed with a mIgG1 isotype control.

Obtained results are represented in the FIGS. 1A (110D7), 1B (1003A2), 1C (1024G11).

The 110D7 antibody shows a maximal cytotoxic effect on the SN12C cells of ~49%. The 1003A2 antibody shows a maximal cytotoxic effect on the SN12C cells of ~37%. The 1024G11 antibody shows a maximal cytotoxic effect on the SN12C cells of ~40%.

No cytotoxicity effect was observed in presence of the 9G4 antibody, considered as mIgG1 isotype control in the experiment.

No cytotoxicity was observed in wells containing only primary antibodies (data not shown). Thus the Axl receptor appears to be a convenient antigen to target for an immunoconjugate approach as the immune complex comprising Axl-110D7-MabZap, Axl-1003A2-MabZap or Axl-1024G11-MabZap triggers an effective cytotoxicity of the targeted cells.

Example 2

Generation of Antibodies Against rhAxl ECD Protein 2.1 Generation of the 110D7 Axl Antibody To generate murine monoclonal antibodies (Mabs) against human extracellular domain (ECD) of the Axl receptor, 5 BALB/c mice were immunized 3-times s.c. with 5-15 µg of the rh Axl-Fc protein (R and D Systems, Cat N°154-AL). The first immunization was performed in presence of Complete Freund Adjuvant (Sigma, St Louis, Md., USA). Incomplete Freund adjuvant (Sigma) was added for following immunizations.

Three days prior to the fusion, immunized mice were boosted with 15 µg of the rhAxl-Fc protein (CIPF) intraperitonealy (i.p.) with IFA.

Splenocytes and lymphocytes were prepared by perfusion of the spleen and by mincing of the proximal lymph nodes, respectively, harvested from 1 out of the 5 immunized mice (selected after sera titration) and fused to SP2/0-Ag14 myeloma cells (ATCC, Rockville, Md., USA). The fusion protocol is described by Kohler and Milstein (Nature, 256: 495-497, 1975). Fused cells are then subjected to HAT selection. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988).

Approximately 10 days after the fusion, colonies of hybrid cells were screened. For the primary screen, supernatants of hybridomas were evaluated for the secretion of Mabs raised against the rhAxl-Fc protein using an ELISA. In parallel, a FACS analysis was performed to select Mabs able to bind to the cellular form of Axl present on the cell surface of the human DU145 prostate tumor cells (ATCC).

As soon as possible, selected hybridomas were cloned by limit dilution and subsequently screened for their reactivity against the human Axl ECD protein. Cloned Mabs were then isotyped using an Isotyping kit (cat #5300.05, Southern Biotech, Birmingham, Ala., USA). One clone obtained from each hybridoma was selected and expanded.

The hybridoma supernatants were assayed by ELISA to determine their binding capacity to the ECD domain of the human Axl receptor or to the rh Axl-Fc protein. When IgG content in supernatants was determined, titration was realized starting at 5 µg/ml. Then a ½ serial dilution was performed in the following 11 rows. Otherwise, supernatants were applied pure. Briefly, 96-well ELISA plates (Costar 3690, Corning, N.Y., USA) were coated 50 µl/well of the rh Axl-Fc protein (R and D Systems, cat N° 154-AL) at 2 µg/ml in PBS overnight at 4° C. The plates were then blocked with PBS containing 0.5% gelatin (#22151, Serva Electrophoresis GmbH, Heidelberg, Germany) for 2 h at 37° C. Once the saturation buffer discarded by flicking plates, 50 µl of pure hybridoma cell supernatants or 50 µl of a 5 µg/ml solution were added to the ELISA plates and incubated for 1 h at 37° C. After three washes, 50 µl horseradish peroxidase-conjugated polyclonal goat anti-mouse IgG (#115-035-164, Jackson Immuno-Research Laboratories, Inc., West Grove, Pa., USA) was added at a ⅕₀₀₀ dilution in PBS containing 0.1% gelatin and 0.05% Tween 20 (w:w) for 1 h at 37° C. Then, ELISA plates were washed 3-times and the TMB (#UP664782, Uptima, Interchim, France) substrate was added. After a 10 min incubation time at room temperature, the reaction was stopped using 1 M sulfuric acid and the optical density at 450 nm was measured.

For the selection by flow cytometry, 100 000 human prostate cancer DU145 cells that express Axl receptor on their surface (ATCC) were plated in each well of a 96 well-plate in PBS containing 1% BSA and 0.01% sodium azide (FACS buffer) at 4° C. After a 2 min centrifugation at 2000 rpm, the buffer was removed and hybridoma supernatants or purified Mabs (1 µg/ml) to be tested were added. After 20 min of incubation at 4° C., cells were washed twice and an Alexa 488-conjugated goat anti-mouse antibody ⅕₀₀° diluted in FACS buffer (#A11017, Molecular Probes Inc., Eugene, USA) was added and incubated for 20 min at 4° C. After a final wash with FACS buffer, cells were analyzed by FACS (Facscalibur, Becton-Dickinson) after addition of propidium iodide to each tube at a final concentration of 40 µg/ml. Wells containing cells alone and cells incubated with the secondary Alexa 488-conjugated antibody were included as negative controls. Isotype controls were used in each experiment (Sigma, ref M90351MG). At least 5000 cells were assessed to calculate the mean value of fluorescence intensity (MFI).

More precisely, the fusion was performed with $310 \cdot 10^6$ of harvested splenocytes and $310 \cdot 10^6$ myeloma cells (1:1 ratio). Two hundred cells of the resulting cell suspension were then plated at $2 \cdot 10^6$ cell/ml in 30 96-well plates.

A first screen (around Day 14 after fusion) both by ELISA on the rh Axl-Fc protein and by FACS analysis using the DU145 tumor cell line allowed to select 5 hybridomas presenting optical densities (ODs) above 0.5 on a rh Axl-Fc coating and MFI above 40 on DU145 human prostate tumor cell line.

These 5 hybridomas were expanded and cloned by limit dilution. One 96-well plate was prepared for each code. Nine days after plating, supernatants from cloning plates were first screened by ELISA for their binding specificity for the extracellular domain of the rh Axl-Fc protein. Then another ELISA assay was run to eliminate anti-Fc Mabs using the immobilized rat recombinant Notch-Fc protein. In addition, hybridomas were tested for the reactivity on DU145 human prostate can cell line by flow cytometry. Three clones of each code were expanded and isotyped. Once produced the anti-Axl antibodies were further studied for their ability to be internalized following Axl binding on the cell-surface.

2.2 Generation of the 1003A2 and 1024G11 Axl Antibodies

To generate murine monoclonal antibodies (Mabs) against human extracellular domain (ECD) of the Axl receptor, 5 BALB/c mice were immunized 4-times s.c. (subcutaneous) with 20 µg of the human monomeric Axl protein (in house product). The first immunization was performed in presence of Complete Freund Adjuvant (Sigma, St Louis, Md., USA). Incomplete Freund adjuvant (Sigma) was added for following immunizations.

Three days prior to the fusion, immunized mice were boosted with 20 µg of the monomeric Axl protein (in house product) intraperitonealy (i.p.) with IFA.

To generate hybridoma cell, splenocytes and lymphocytes were prepared by perfusion of the spleen and by mincing of the proximal lymph nodes, respectively, harvested from 1 out of the 5 immunized mice (selected after sera titration) and fused to SP2/0-Ag14 myeloma cells (ATCC, Rockville, Md., USA). The fusion protocol is described by Kohler and Milstein (Nature, 256:495-497, 1975). Fused cells are then subjected to HAT selection. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988).

Approximately 10 days after the fusion, colonies of hybrid cells were screened. For the primary screen, supernatants of hybridomas were evaluated for the secretion of Mabs raised against the human monomeric Axl protein (CIPF) using an ELISA. In parallel, a FACS analysis was performed to select Mabs able to bind to the cellular form of Axl present on the cell surface of the human DU145 prostate tumor cells (ATCC).

As soon as possible, selected hybridomas were cloned by limit dilution and subsequently screened for their reactivity against the monomeric Axl receptor. Cloned Mabs were then isotyped using an Isotyping kit (cat #5300.05, Southern Biotech, Birmingham, Ala., USA). One clone obtained from each hybridoma was selected and expanded.

The hybridoma supernatants were assayed by ELISA to determine their binding capacity to the ECD domain of the human Axl receptor. When IgG content in supernatants was determined, titration was realized starting at 5 µg/ml. Then a ½ serial dilution was performed in the following 11 rows. Otherwise, supernatants were applied pure. Briefly, 96-well ELISA plates (Costar 3690, Corning, N.Y., USA) were coated with either 50 µl/well of a ECD Axl solution (CIPF) at 2 µg/ml in PBS or 50 µl/well of the rh Axl-Fc protein (R and D Systems, cat N° 154-AL) at 2 µg/ml in PBS overnight at 4° C. The plates were then blocked with PBS containing 0.5% gelatin (#22151, Serva Electrophoresis GmbH, Heidelberg, Germany) for 2 h at 37° C. Once the saturation buffer discarded by flicking plates, 50 µl of pure hybridoma cell supernatants or 50 µl of a 5 µg/ml solution were added to the ELISA plates and incubated for 1 h at 37° C. After three washes, 50 µl horseradish peroxidase-conjugated polyclonal goat anti-mouse IgG (#115-035-164, Jackson Immuno-Research Laboratories, Inc., West Grove, Pa., USA) was added at a 1/5000 dilution in PBS containing 0.1% gelatin and 0.05% Tween 20 (w:w) for 1 h at 37° C. Then, ELISA plates were washed 3-times and the TMB (#UP664782, Uptima, Interchim, France) substrate was added. After a 10 min incubation time at room temperature, the reaction was stopped using 1 M sulfuric acid and the optical density at 450 nm was measured.

For the selection by flow cytometry, 100 000 human prostate cancer DU145 cells that express Axl receptor on their surface (ATCC) were plated in each well of a 96 well-plate in PBS containing 1% BSA and 0.01% sodium azide (FACS buffer) at 4° C. After a 2 min centrifugation at 2000 rpm, the buffer was removed and hybridoma supernatants or purified Mabs (1 µg/ml) to be tested were added. After 20 min of incubation at 4° C., cells were washed twice and an Alexa 488-conjugated goat anti-mouse antibody 1/500° diluted in FACS buffer (#A11017, Molecular Probes Inc., Eugene, USA) was added and incubated for 20 min at 4° C. After a final wash with FACS buffer, cells were analyzed by FACS (Facscalibur, Becton-Dickinson) after addition of propidium iodide to each tube at a final concentration of 40 µg/ml. Wells containing cells alone and cells incubated with the secondary Alexa 488-conjugated antibody were included as negative controls. Isotype controls were used in each experiment (Sigma, ref M90351MG). At least 5000 cells were assessed to calculate the mean value of fluorescence intensity (MFI).

The fusion was performed with $280 \cdot 10^6$ harvested splenocytes and lymphocytes and $280 \cdot 10^6$ myeloma cells (1:1 ratio). The resulting fused cell suspension ($2 \cdot 10^6$ cell/ml) was then plated in 30 96-well plates.

A first screen (around Day 14 after fusion) both by ELISA on the immobilized Axl ECD protein allowed selecting 69 hybridomas presenting optical densities (ODs) above 1 on the ECD Axl coating. A complementary FACS analysis using the DU145 tumor cell line limits the number of selected hybridomas. At this step 17 hybridomas presenting MFI above 100 on DU145 human prostate tumor cell line were kept and cloned by limit dilution. Cloning plates were screened using monomeric Axl ELISA; selected hybridomas were then expanded and further characterized for their binding specificity and their ability to be internalized.

Example 3

Axl Binding Specificity

In this example, the binding of the 110D7, 1003A2, 1024G11 antibodies is respectively studied on the rhAxl-Fc protein. Secondly, its binding in the two other members of the TAM family, rhDtk-Fc and rhMer-Fc, is studied.

Figure 2A:
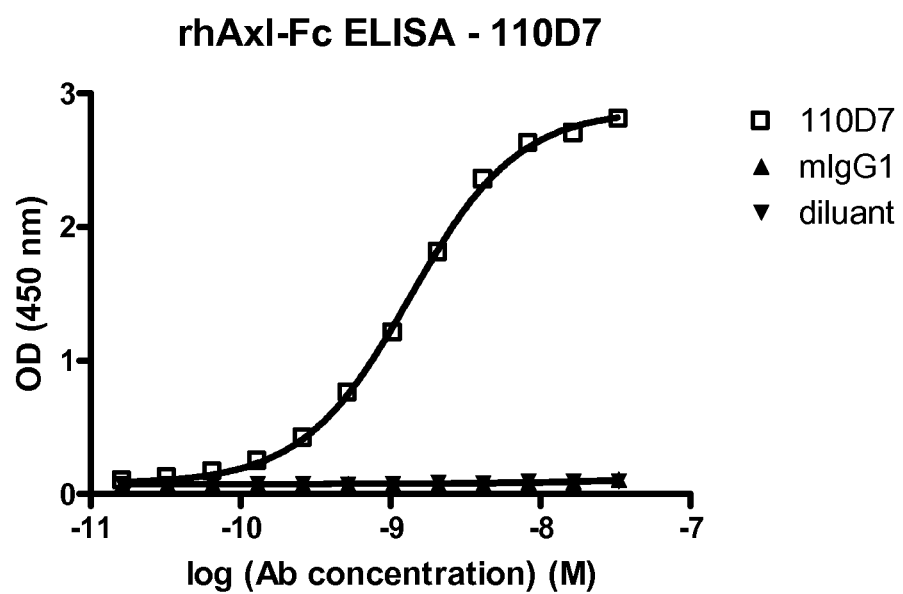
Figure 2B:
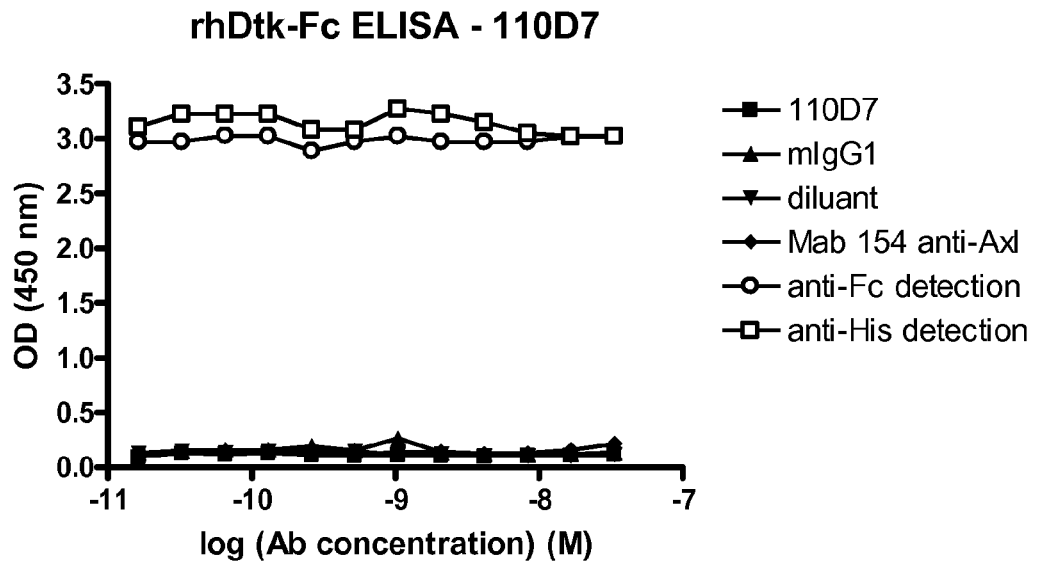
Figure 2C:
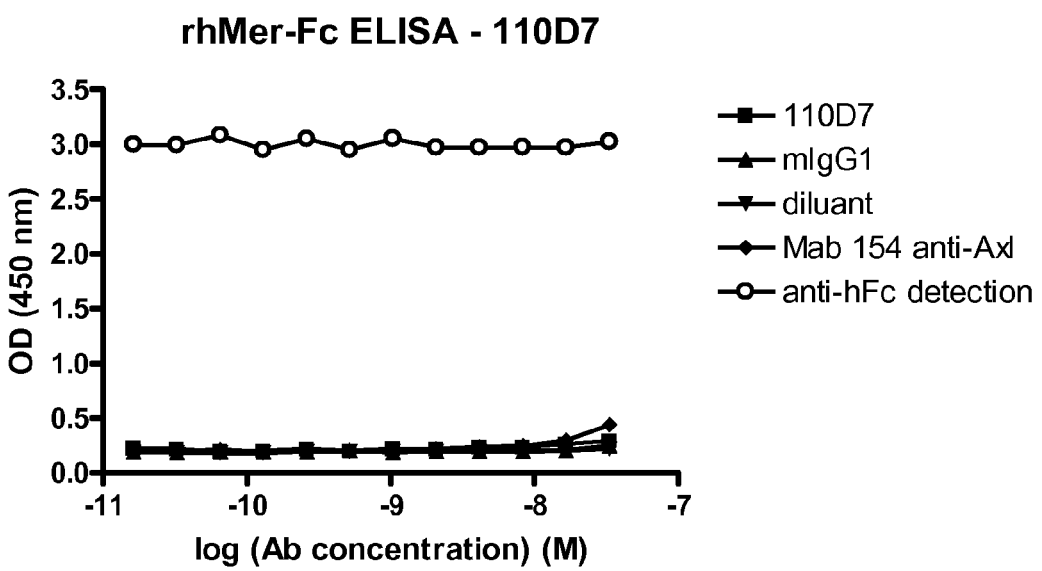
Figure 2D:
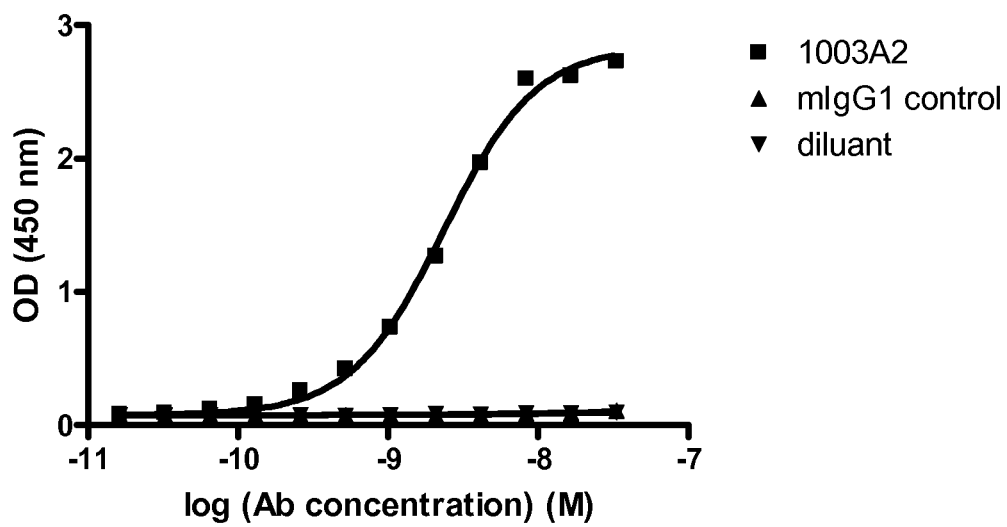
Figure 2E:
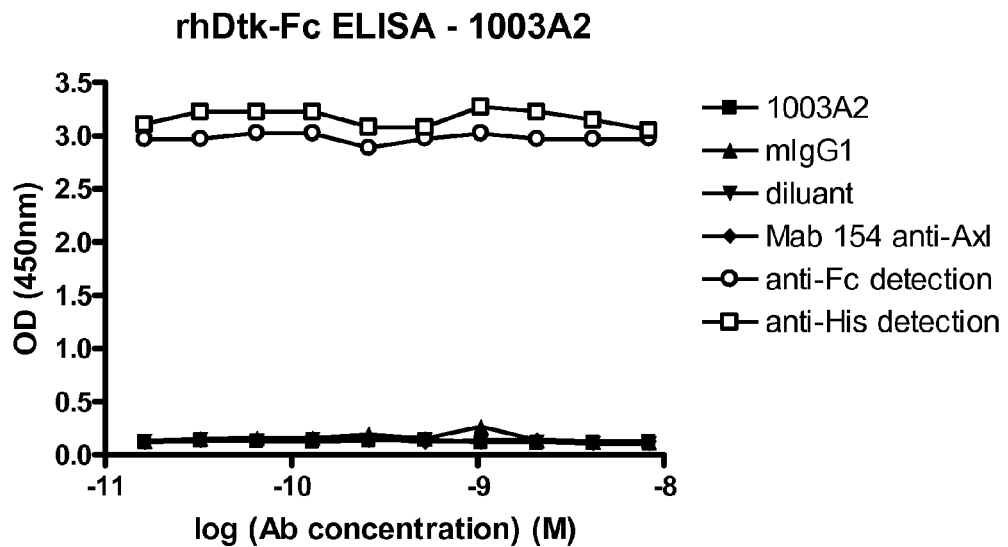
Figure 2F:
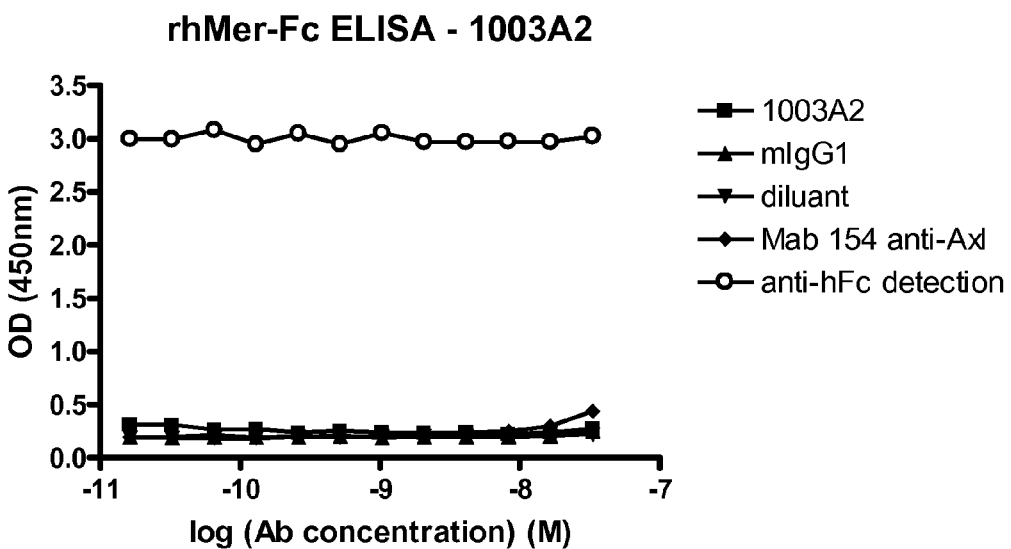
Figure 2G:
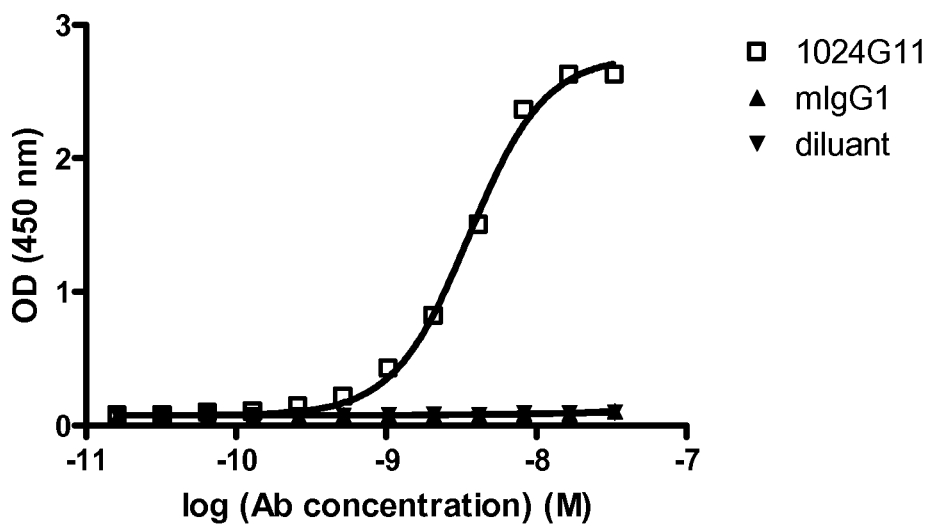
Figure 2H:
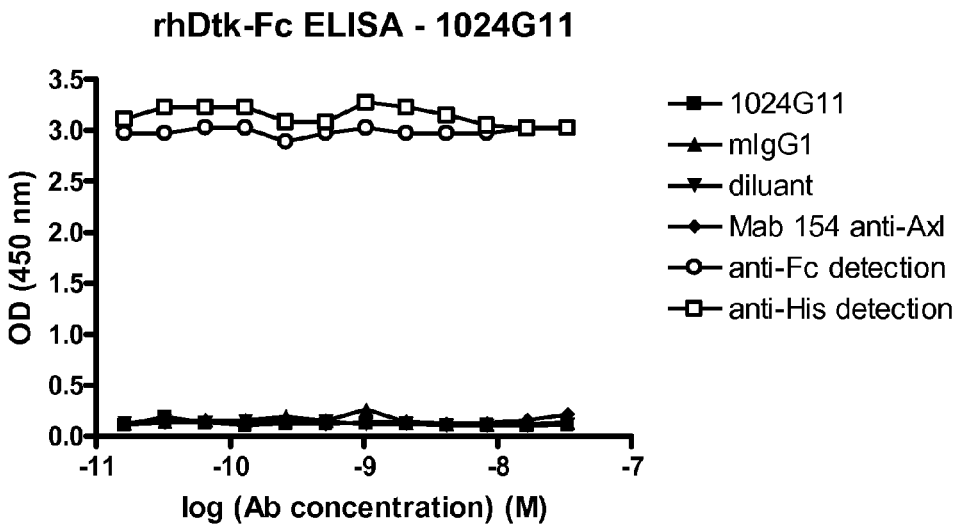
Figure 2I:
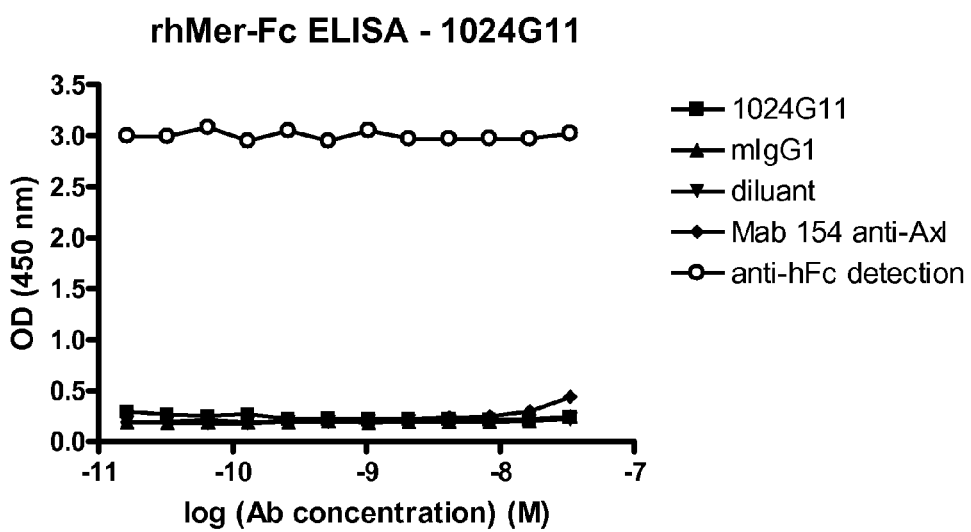

Briefly, the recombinant human Axl-Fc (R and D systems, cat N° 154AL/CF), rhDtk (R and D Systems, cat N° 859-DK) or rh-Mer-Fc (R and D Systems, cat N° 891-MR) proteins were coated overnight at 4° C. to Immulon II 96-well plates and, after a 1 h blocking step with a 0.5% gelatine solution, 110D7, 1003A2, 1024G11 purified antibodies were added, respectively, for an additional 1 h at 37° C. at starting concentration of 5 µg/ml ($3.33 \cdot 10^{-8}$M). Then ½ serial dilutions were done over 12 columns. Then plates were washed and a goat anti-mouse (Jackson) specific IgG-HRP was added for 1 h at 37° C. Reaction development was performed using the TMB substrate solution. The commercial anti-Axl Mab 154 antibody is also used in parallel (data not shown). Coating controls are performed in presence of a goat anti-human IgG Fc polyclonal serum labelled with HRP (Jackson, ref 109-035-098) and/or in presence of a HRP-coupled anti-Histidine antibody (R and D Systems, ref: MAB050H). No non specific binding is observed in absence of primary antibody (diluant). Results for the 110D7 are represented in FIGS. 2A, 2B and 2C, respectively. Results for the 1003A2 are represented in FIGS. 2D, 2E and 2F, respectively. Results for the 1024G11 are represented in FIGS. 2G, 2H and 2I, respectively.

This example shows that the 110D7, 1003A2, 1024G11 antibodies only bind to the rhAxl-Fc protein and do not bind on two other members of the TAM family, rhDtk or rhMer. No cross-specificity of binding of the 110D7, 1003A2, 1024G11 antibodies is observed between TAM members.

Example 4

Axl Detection on Human Tumor Cells

Cell surface Axl expression level on human tumor cells was first established using a commercial Axl antibody (R and D Systems, ref: MAB154) in parallel of calibration beads to allow the quantification of Axl expression level. Secondly, binding of the cell-surface Axl was studied using 110D7, 1003A2 and 1024G11. In both case, the experimental conditions were as briefly described bellow.

For cell surface binding studies, two fold serial dilutions of a 10 μg/ml (6.66 $10^{-8}$ M) primary antibody solution (110D7, 1003A2, 1024G11, MAB154 Axl commercial antibody or mIgG1 isotype control 9G4 Mab) are prepared on 11 points and are applied on $2 \cdot 10^5$ cells for 20 min at 4° C. After 3 washes in phosphate-buffered saline (PBS) supplemented with 1% BSA and 0.01% NaN$_3$, cells were incubated with secondary antibody Goat anti-mouse Alexa 488 (1/500° dilution) for 20 minutes at 4° C. After 3 additional washes in PBS supplemented with 1% BSA and 0.1% NaN$_3$, cells were analyzed by FACS (Facscalibur, Becton-Dickinson). At least 5000 cells were assessed to calculate the mean value of fluorescence intensity.

For quantitative ABC determination using MAB154 Axl antibody, QIFIKIT® calibration beads are used. Then, the cells are incubated, in parallel with the QIFIKIT® beads, with Polyclonal Goat Anti-Mouse Immunoglobulins/FITC, Goat F(ab')$_2$, at saturating concentration. The number of antigenic sites on the specimen cells is then determined by interpolation of the calibration curve (the fluorescence intensity of the individual bead populations against the number of Mab molecules on the beads.

4.1. Quantification of Cell-Surface Axl Expression Level

Axl expression level on the surface of human tumor cells was determined by flow cytometry using indirect immunofluorescence assay (QIFIKIT® method (Dako, Denmark), a quantitative flow cytometry kit for assessing cell surface antigens. A comparison of the mean fluorescence intensity (MFI) of the known antigen levels of the beads via a calibration graph permits determination of the antibody binding capacity (ABC) of the cell lines.

Table 6 presents Axl expression level detected on the surface of various human tumor cell lines (SN12C, Calu-1, A172, A431, DU145, MDA-MB435S, MDA-MB231, PC3, NCI-H226, NCI-H125, MCF7, Panc1) (ATCC, NCI) as determined using QIFIKIT® in presence of the Axl commercial antibody MAB154 (R and D Systems). Values are given as Antigen binding complex (ABC).

labelling were observed, revealing variable levels of cell-surface Axl receptor on human tumor cells. No binding of Axl receptor was observed using MCF7 human breast tumor cell line.

Example 5

110D7, 1003A2, 1024G11 Antibodies Inter-Species Crosspecificity

To address the species cross-specificity of the 110D7, 1003A2 and 1024G11, anti-Axl antibodies, 2 species were considered: mouse and monkey. First the binding on the recombinant mouse (rm) Axl receptor is studied by ELISA (FIGS. 4A to C). Secondly flow cytometry experiments were performed using monkey COS7 cells as these cells expressed the Axl receptor on their surface (FIGS. 5A to C). The COS7 cell line was obtained by immortalizing a CV-1 cell line derived from kidney cells of the African green monkey with a version of the SV40 genome that can produce large T antigen but has a defect in genomic replication.

5.1 rmAxl-Fc ELISA

Briefly, the recombinant mouse Axl-Fc (R and D Systems, cat N° 854-AX/CF) proteins were coated overnight at 4° C. to Immulon II 96-well plates and, after a 1 h blocking step with a 0.5% gelatine solution, the 110D7, 1003A2, 1024G11, purified antibodies, respectively, were added for an additional 1 h at 37° C. at starting concentration of 5 μg/ml (3.33 $10^{-8}$ M). Then ½ serial dilutions were done over 12 columns. Then plates were washed and a goat anti-mouse (Jackson) specific IgG HRP was added for 1 h at 37° C. Reaction development was performed using the TMB substrate solution. The commercial mouse anti-Axl Mab 154 antibody is also used in parallel. Coating controls are performed in presence of a goat anti-human IgG Fc polyclonal serum coupled with HRP (Jackson, ref 109-035-098) and in presence of a HRP-coupled anti-Histidine antibody

TABLE 6

|  | MCF7 | NCI-H125 | MDA-MB-435S | Panc1 | MDA-MB-231 | Calu-1 | SN12C |
|---|---|---|---|---|---|---|---|
| Tumor type/organ | Breast | NSCLC | Breast | Pancreas | Breast | Lung | Renal |
| ABC (Qifikit) | 71 | 5 540 | 17 814 | 36 809 | 61 186 | >100 000 | >100 000 |

|  | A172 | A431 | DU-145 | PC3 | NCI-H226 |
|---|---|---|---|---|---|
| Tumor type/organ | glioblastoma | Epidermoid carcinoma | Prostate | prostate | NSCLC |
| ABC (Qifikit) | 52421 | 3953 | 55268 | 8421 | 32142 |

Results obtained with a commercial Axl monoclonal antibody (MAB154) showed that Axl receptor is expressed at various levels depending of the considered human tumor cell.

4.2. Axl Detection Using 110D7, 1003A2 and 1024G11 Axl Antibodies on Human Tumor Cells More specifically, Axl binding was studied using Axl 110D7, 1003A2 or 1024G11 antibodies. Axl Antibody dose response curves were applied. MFIs obtained using the various human tumor cells were then analysed with Prism software. Data are presented in FIGS. 3A-3C.

Data indicate that the three Axl antibodies bind specifically to the membrane Axl receptor as attested by the saturation curve profiles. However different intensities of (R and D Systems, ref: MAB050H). No specific binding is observed in absence of primary antibody (diluant).

Results are represented in FIG. 4A (110D7), 4B (1003A2) and 4C (1024G11).

The FIG. 4A shows that the 110D7 antibody of the present invention is able to bind to the murine Axl ECD domain only in presence of high antibody concentration (above 8.3 $10^{-9}$ M).

The FIG. 4B shows that the 1003A2 antibody of the present invention does not bind to the murine Axl ECD domain.

The FIG. 4C shows that the 1024G11 antibody of the present invention does not bind to the murine Axl ECD domain.

5.2 FACS COS7

For 110D7, respectively 1003A2 and 1024G11, cellular binding purpose, $2 \cdot 10^5$ cells were incubated with an antibody concentration range prepared by ½ serial dilution (12 points) of a 10 µg/ml (6.66 $10^{-8}$ M) antibody solution of 110D7, respectively 1003A2 and 1024G11, or m9G4 (mIgG1 isotype control Mab) for 20 min at 4° C. After 3 washes in phosphate-buffered saline (PBS) supplemented with 1% BSA and 0.01% $NaN_3$, cells were incubated with secondary antibody goat anti-mouse Alexa 488 (dilution ⅟500) for 20 minutes at 4° C. After 3 additional washes in PBS supplemented with 1% BSA and 0.1% $NaN_3$, cells were analyzed by FACS (Facscalibur, Becton-Dickinson). At least 5000 cells were assessed to calculate the mean value of fluorescence intensity. Data are analyzed using Prism software.

Results are represented in FIGS. 5A (110D7), 5B (1003A2) and 5C (1024G11).

The titration curve established on COS7 cells using 110D7, respectively 1003A2 and 1024G11, antibody and mIgG1 isotype control confirms that 110D7, respectively 1003A2 and 1024G11, are able to recognize monkey cellular form of the Axl receptor expressed on the surface of the COS7 cells.

Plateau is reached for 110D7 antibody concentrations above 156 µg/ml ($10^{-9}$M). Plateau is reached for 1003A2 antibody concentrations above 0.07 µg/ml (5.2 $10^{-10}$M). Plateau is reached for 1024G11 antibody concentrations above 0.07 µg/ml (5.2 $10^{-10}$M).

No binding is observed in presence of the mIgG1 isotype control.

Example 6

Gas6 Competition Experiments Performed in Presence of the 110D7, 1003A2 and 1024G11 Antibodies To further characterize the anti-Axl Mabs, Gas6 competition assays were performed. In this assay, the free rhAxl-Fc protein and the anti-Axl antibody are incubated to form antigen-antibody complex and then the complexes are loaded on Gas6-coated surface in the assay plate. The unbound antibody-antigen complexes are washed off before adding enzyme-linked secondary antibody against the human Fc portion of the rhAxl-Fc protein. The substrate is then added and the antigen concentration can then be determined by the signal strength elicited by the enzyme-substrate reaction.

Briefly reaction mixture comprising the rhAxl-Fc protein in presence or not of the Mabs to be tested, are prepared on a separate saturated (0.5% gelatin in PBS 1×) plate. Serial 1:2 dilutions (starting from 80 µg/ml on 12 columns) of murine Axl antibodies (110D7, 1003A2 and 1024G11) are performed. Then 0.5 µg/ml of the rhAxl-Fc protein is added (R and D Systems, ref 154AL/CF), except to the negative control line that contains only ELISA diluant (0.1% gelatin, 0.05% Tween 20 in PBS 1×). After homogenisation, the competition samples are loaded on Gas6-coated plates with a 6 µg/ml rhGas6 solution in PBS (R and D Systems cat N° 885-GS-CS/CF). After incubation and several washes, bound rhAxl-Fc proteins are detected using a goat anti-Human IgG-HRP (Jackson, ref 109-035-098). Once bound, the TMB substrate is added to the plates. The reaction is stopped by addition of $H_2SO_4$ acid solution and the obtained optical densities read at 450 nm using a microplate reader instrument.

This experiment (FIGS. 6A, 6B and 6C, respectively) shows that 110D7, 1003A2 and 1024G11 are able to compete with the rhAxl-Fc binding on their immobilized ligand. Competition with Gas6 binding occurs in presence of 110D7 antibody concentrations above 2.5 µg/ml (1.67 $10^{-8}$ M). Competition with Gas6 binding occurs in presence of 1003A2 antibody concentrations above 2.5 µg/ml (1.67 $10^{-8}$ M). No more binding of the rhAxl-Fc on the immobilized Gas6 is observed in presence of 1003A2 antibody concentration above 10 µg/ml (6.67 $10^{-8}$ M). Competition with Gas6 binding occurs in presence of 1024G11 antibody concentrations above 2.5 µg/ml (1.67 $10^{-8}$ M). No more binding of the rhAxl-Fc on the immobilized Gas6 is observed in presence of 1024G11 antibody concentration above 10 µg/ml (6.67 $10^{-8}$ M).

The 110D7, 1003A2 and the 1024G11 antibodies block Gas6 binding on rhAxl-Fc.

Example 7

Epitope Recognition by Western Blot

To determine if the 110D7, 1003A2 and 1024G11 anti-Axl antibodies recognize a linear or a conformational epitope, western blot analysis was done using SN12C cell lysates. Samples were differently treated to be in reducing or non reducing conditions. If a band is visualized with reduced sample, the tested antibody targets a linear epitope of the ECD domain; If not, it is raised against a conformation epitope of the Axl ECD.

SN12C cells were seeded in RPMI+10% heat inactivated FBS+2 mM L-glutamine at $5 \cdot 10^4$ cells/cm$^2$ in T162 cm$^2$ flasks for 72 h at 37° C. in a 5% $CO_2$ atmosphere. Then the cells were washed twice with phosphate buffered saline (PBS) and lysed with 1.5 ml of ice-cold lysis buffer [50 mM Tris-HCl (pH7.5); 150 mM NaCl; 1% Nonidet P40; 0.5% deoxycholate; and 1 complete protease inhibitor cocktail tablet plus 1% antiphosphatases]. Cell lysates were shaken for 90 min at 4° C. and cleared at 15 000 rpm for 10 min. Protein concentration was quantified using BCA. Various samples were loaded. First 10 µg of whole cell lysate (10 µg in 20 µl) were prepared in reducing conditions (1× sample buffer (BIORAD)+1× reducing agent (BIORAD)) and loaded on a SDS-PAGE after 2 min incubation at 96° C. Secondly two other samples of 10 µg of whole cell lysate were prepared in non-reducing conditions (in 1× sample buffer (BIORAD) only). Prior to be loaded on the SDS-PAGE gel, one of these two last samples is heated 2 min incubation at 96° C.; the other one is kept on ice. After migration, the proteins are transferred to nitrocellulose membrane. Membranes were saturated for 1 h at RT with TBS-tween 20 0.1% (TBST); 5% non-fat milk and probed with the 110D7, respectively 1003A2 and 1024G11 antibody at 10 µg/ml overnight at 4° C. in TBST-5% non fat dry milk. Antibodies were diluted in Tris-buffered saline—0.1% tween 20 (v/v) (TBST) with 1% non-fat dry milk. Then membranes were washed with TBST and incubated with peroxydase-conjugated secondary antibody (dilution ⅟1000) for 1 h at RT. Immunoreactive proteins were visualized with ECL (Pierce #32209). After Axl visualization, membranes were washed once again with TBST and incubated for 1 h at RT with mouse anti-GAPDH antibody (dilution ⅟200,000) in TBST-5% non fat dry milk. Then membranes were washed in TBST and incubated with peroxydase-conjugated secondary antibody, for 1 h at RT. Membranes were washed and GAPDH was revealed using ECL.

Results are represented in FIGS. 7A (110D7), 7B (1003A2) and 7C (1024G11).

The 110D7, 1003A2 and 1024G11 anti-Axl antibodies recognize a conformational epitope as a specific band is only observed in non-reduced conditions. No band is observed in denaturating migration condition of the SN12C cell lysate.

Example 8

Measurement of Axl Down-Regulation Triggered by the 110D7, 1003A2, 1024G11 Antibodies by Western Blot In the following example, the human renal cell carcinoma cell line SN12C (ATCC) was selected to address the activity of antibodies on Axl receptor expression. The SN12C cell line overexpresses the Axl receptor. The Axl down-regulation was studied by Western-Blot on whole cell extracts in FIGS. 8A-8B (110D7), 8C-8D (1003A2), 8E-8F (1024G11).

SN12C cells were seeded in RPMI+10% heat inactivated FBS+2 mM L-glutamine at $6 \cdot 10^4$ cells/cm$^2$ in six-well plates for 48 h at 37° C. in a 5% $CO_2$ atmosphere. After two washes with phosphate buffer saline (PBS), cells were serum-starved in a medium containing either 800 ng/ml recombinant mouse gas6 ligand (R and D Systems, ref: 986-GS/CF) or 10 µg/ml of a mIgG1 isotype control antibody (9G4) or 10 µg/ml of the anti-Axl antibody of the present invention and incubated for 4 h or 24 additional hours. Then the medium was gently removed and cells washed twice with cold PBS. Cells were lysed with 200 µl of ice-cold lysis buffer [50 mM Tris-HCl (pH7.5); 150 mM NaCl; 1% Nonidet P40; 0.5% deoxycholate; and 1 complete protease inhibitor cocktail tablet plus 1% antiphosphatases]. Cell lysates were shaken for 90 min at 4° C. and cleared at 15 000 rpm for 10 min. Protein concentration was quantified using BCA. Whole cell lysates (10 µg in 20 µl) were separated by SDS-PAGE and transferred to nitrocellulose membrane. Membranes were saturated for 1 h at RT with TBS-Tween 20 0.1% (TBST); 5% non-fat milk and probed with a commercial anti-Axl antibody at 0.5 µg/ml (AbNova H00000558-M02) overnight at 4° C. in TBST-5% non fat dry milk. Antibodies were diluted in Tris-buffered saline—0.1% tween 20 (v/v) (TBST) with 1% non-fat dry milk. Then membranes were washed with TBST and incubated with peroxydase-conjugated secondary antibody (dilution 1/1000) for 1 h at RT. Immunoreactive proteins were visualized with ECL (Pierce #32209). After Axl visualization, membranes were washed once again with TBST and incubated for 1 h at RT with mouse anti-GAPDH antibody (dilution 1/200000) in TBST-5% non fat dry milk. Then membranes were washed in TBST and incubated with peroxydase-conjugated secondary antibodies, for 1h at RT. Membranes were washed and GAPDH was revealed using ECL. Band intensity was quantified by densitometry.

Figure 8A:
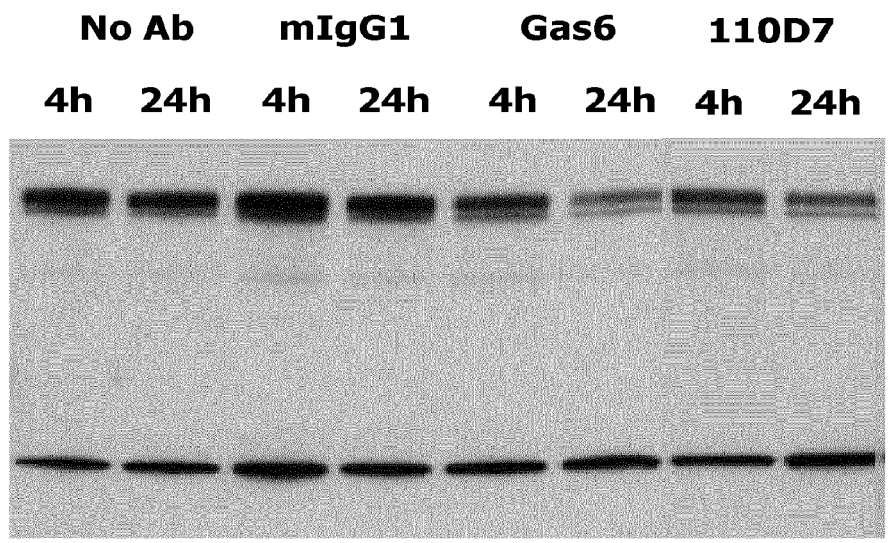
Figure 8B:
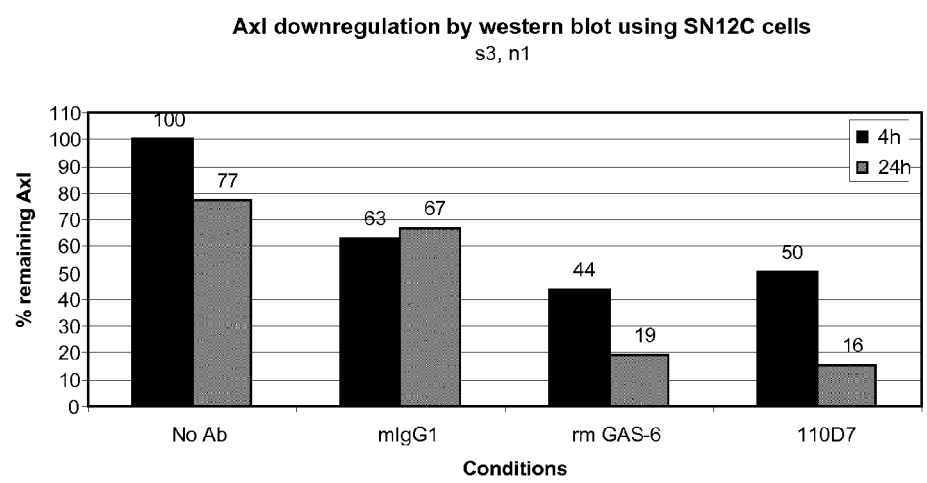

Results presented in FIGS. 8A and 8B are representative of 3 independent experiments and demonstrate that 110D7 is able to down-regulate Axl in an Axl-overexpressing human tumor cell line. At 4 h, the 110D7 antibody triggers a 50% Axl down-regulation, and up to 84% after a 24 hour incubation with the 110D7 antibody.

Figure 8C:
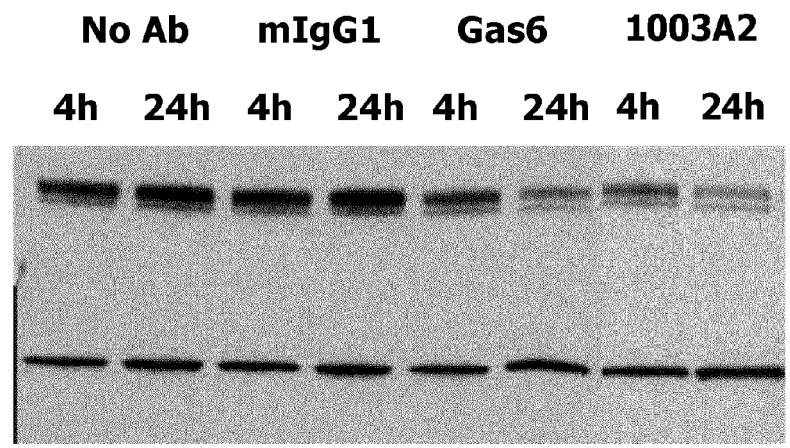
Figure 8D:
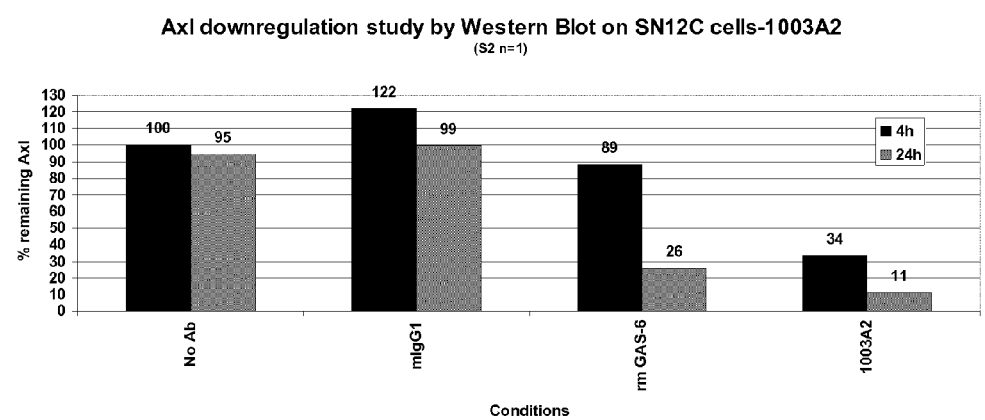

Results presented in FIGS. 8C and 8D are representative of 3 independent experiments and demonstrate that 1003A2 is able to down-regulate Axl in an Axl-overexpressing human tumor cell line. At 4 h, the 1003A2 antibody triggers a 66% Axl down-regulation, and up to 89% after a 24 hour incubation with the 1003A2 antibody.

Figure 8E:
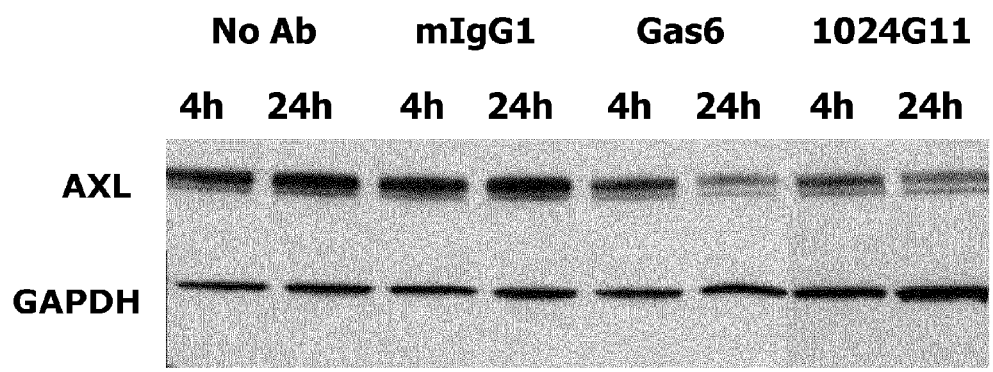
Figure 8F:
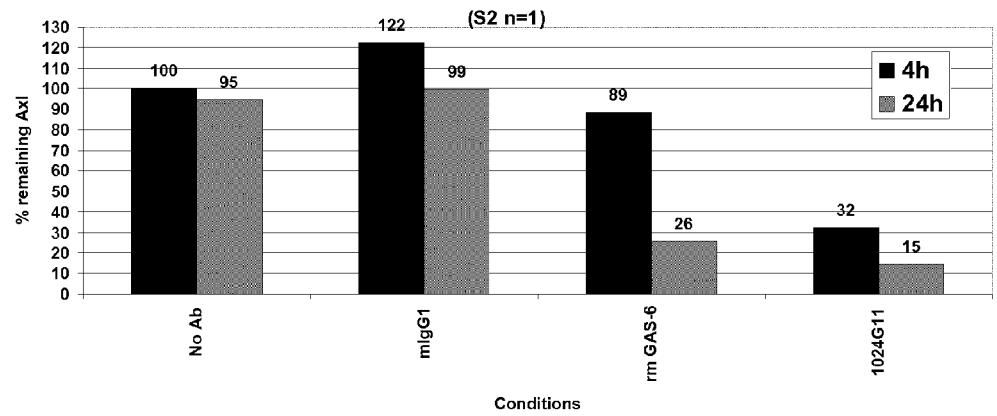

Results presented in FIGS. 8E and 8F are representative of 3 independent experiments and demonstrate that 1024G11 is able to down-regulate Axl in an Axl-overexpressing human tumor cell line. At 4 h, the 1024G11 antibody triggers a 68% Axl down-regulation, and up to 85% after a 24 hour incubation with the 1024G11 antibody.

Example 9

Flow Cytometry Study of Anti-Axl Antibody Effect on Cell Surface Axl Expression

Flow cytometry technique allows labelling of cell-surface Axl receptor. The use of this technique can highlight the effect of antibody on the membrane Axl expression Human renal tumor SN12C cells that express high levels of Axl were used in this example.

SN12C tumor cell line was cultured in RMPI1640 with 1% L-glutamine and 10% of FCS for 3 days before experiment. Cells were then detached using trypsin and plated in 6-multiwell plate in RPMI1640 with 1% L-glutamine and 5% FCS. The next day, antibodies of interest were added at 10 µg/ml. Untreated wells were also included. The cells are incubated at 37° C., 5% $CO_2$. Twenty-four hour later, cells were washed with PBS, detached and incubated with the same antibodies of interest in FACS buffer (PBS, 1% BSA, 0.01% sodium azide). Untreated wells were also stained with the same antibody in order to compare the signal intensity obtained with the same Mab on the treated and the non-treated cells. Cells were incubated for 20 minutes at 4° C. and washed three times with FACS buffer. An Alexa 488 labeled-goat anti-mouse IgG antibody was incubated for 20 minutes and cells were washed three times before FACS analysis on propidium iodide negative cell population. The difference between the staining of a Mab in the untreated cell and the treated condition with the same antibody indicated a down-regulation of the Axl protein on the cell surface of the cells.

Two parameters are determined: (i) the percentage of remaining Axl on the cell surface and ii) the difference of the fluorescent signal detected on the surface of 110D7, respectively 1003A2, 1024G11 treated cells compared to the mIgG1 treated cells at T24 h. % remaining Axl is calculated as follows:

% remaining Axl=(MFI Mab of the invention 24 h/MFI mIgG1 24 h)×100

Data from one representative experiment are presented in Table 7. The results were reproduced in three independent experiments.

The difference of MFI between the staining of a Mab in the untreated cell and the treated condition with the same antibody reflects a down-regulation of the Axl protein on the cell surface of the cells due to the binding of the considered Mab. Conditions without antibody gave similar results to conditions in presence of the isotype control antibody (m9G4).

TABLE 7

| Labelling | Treatment | MFI at T24 h | $\Delta$ (MFI$_{No\ Ab\ 24\ h}$ − MFI$_{Ab\ 24\ h}$) | % remaining Axl |
|---|---|---|---|---|
| 110D7 | No Ab | 838 | 588 | 29.8 |
|  | 110D7 | 250 |  |  |
| 1003A2 | No Ab | 779 | 505 | 35 |
|  | 9G4 | 274 |  |  |

TABLE 7-continued

| Labelling | Treatment | MFI at T24 h | Δ (MFI$_{No\ Ab\ 24\ h}$ - MFI$_{Ab\ 24\ h}$) | % remaining Axl |
|---|---|---|---|---|
| 1024G11 | No Ab | 877 | 478 | 45.5 |
|  | 9G4 | 399 |  |  |
| 9G4 | No Ab | 11 | −2 | 117 |
|  | 9G4 | 13 |  |  |
| MAB154 | No Ab | 950 | ND | ND |
|  | 9G4 | ND |  |  |

ND: not determined

The data demonstrate that the mean fluorescence intensity detected on the surface of the cells treated with 110D7 for 24 hours is reduced (−588) compared to the MFIs obtained with untreated cells labelled with the 110D7 antibody. After a 24 h incubation with the 110D7 antibody, 29.8% of the cell-surface Axl receptor remains at the SN12C cell-surface.

The data demonstrate that the mean fluorescence intensity detected on the surface of the cells treated with 1003A2 for 24 hours is reduced (−505) compared to the MFIs obtained with untreated cells labelled with the 1003A2 antibody. After a 24 h incubation with the 1003A2 antibody, 35% of the cell-surface Axl receptor remains at the SN12C cell-surface.

The data demonstrate that the mean fluorescence intensity detected on the surface of the cells treated with 1024G11 for 24 hours is reduced (−478) compared to the MFIs obtained with untreated cells labelled with the 1024G11 antibody. After a 24 h incubation with the 1024G11 antibody, 45.5% of the cell-surface Axl receptor remains at the SN12C cell-surface.

Example 10

Anti-Axl Antibody Internalization Study Using Fluorescent Immunocytochemistry Labelling Complementary internalization results are obtained by confocal microscopy using indirect fluorescent labelling method.

Briefly, SN12C tumor cell line was cultured in RMPI1640 with 1% L-glutamine and 10% of FCS for 3 days before experiment. Cells were then detached using trypsin and plated in 6-multiwell plate containing coverslide in RPMI1640 with 1% L-glutamine and 5% FCS. The next day, the antibody 110D7, respectively 1003A2 and 1024G11 was added at 10 µg/ml. Cells treated with an irrelevant antibody were also included. The cells were then incubated for 1 h and 2 h at 37° C., 5% CO$_2$. For T 0 h, cells were incubated for 30 minutes at 4° C. to determine antibody binding on cell surface. Cells were washed with PBS and fixed with para-formaldhehyde for 15 minutes. Cells were rinsed and incubated with a goat anti-mouse IgG Alexa 488 antibody for 60 minutes at 4° C. to identify remaining antibody on the cell surface. To follow antibody penetration into the cells, cells were fixed and permeabilized with saponin. A goat anti-mouse IgG Alexa 488 (Invitrogen) was used to stain both the membrane and the intracellular antibody. Early endosomes were identified using a rabbit polyclonal antibody against EEA1 revealed with a goat anti-rabbit IgG-Alexa 555 antibody (Invitrogen). Cells were washed three times and nuclei were stained using Draq5. After staining, cells were mounted in Prolong Gold mounting medium (Invitrogen) and analyzed by using a Zeiss LSM 510 confocal microscope.

Figure 9A:
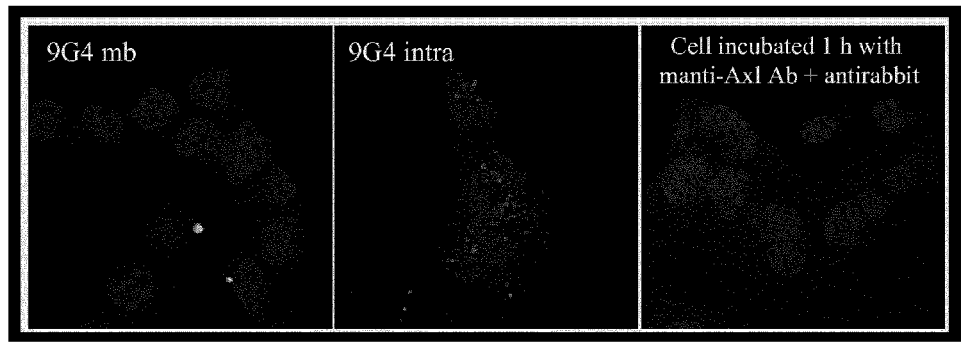
Figure 9B:
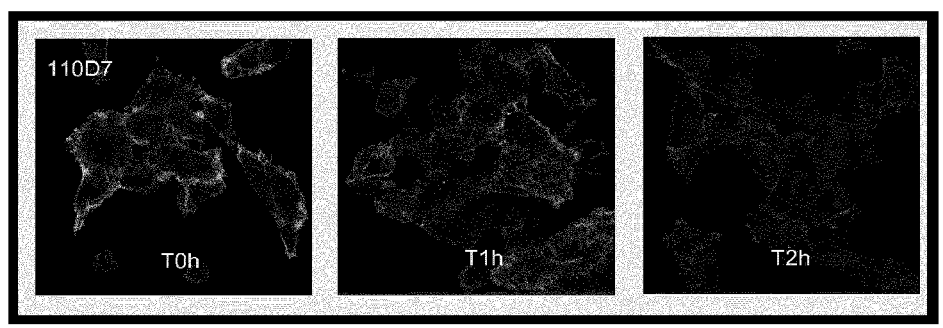
Figure 9C:
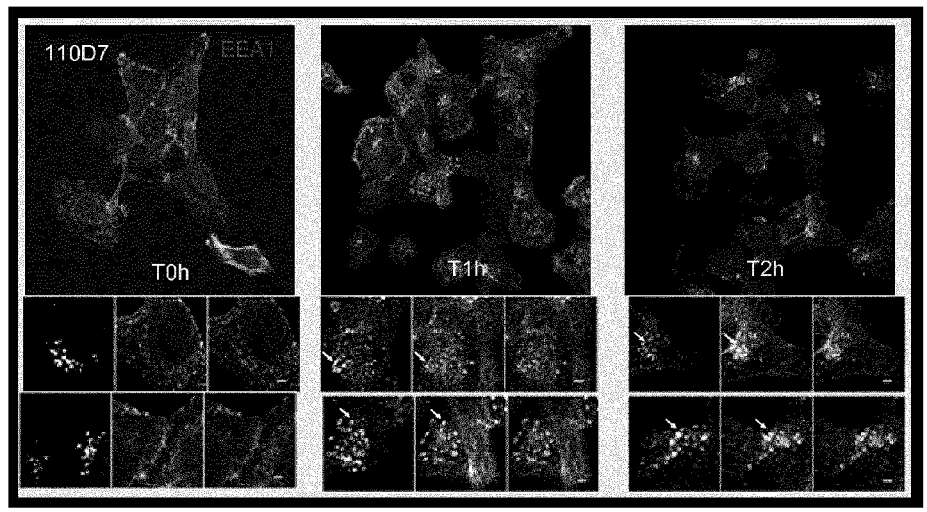

Photographs are presented in FIGS. 9A-9C (110D7), 9D-9F (1003A2) and 9G-9I (1024G11).

Figure 9D:
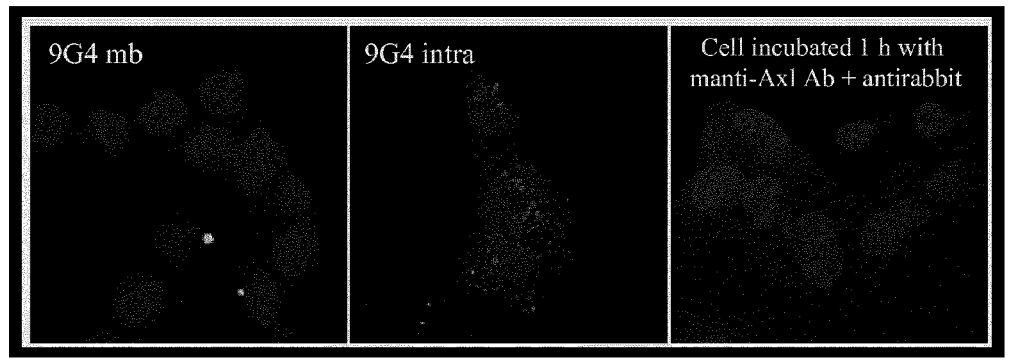
Figure 9E:
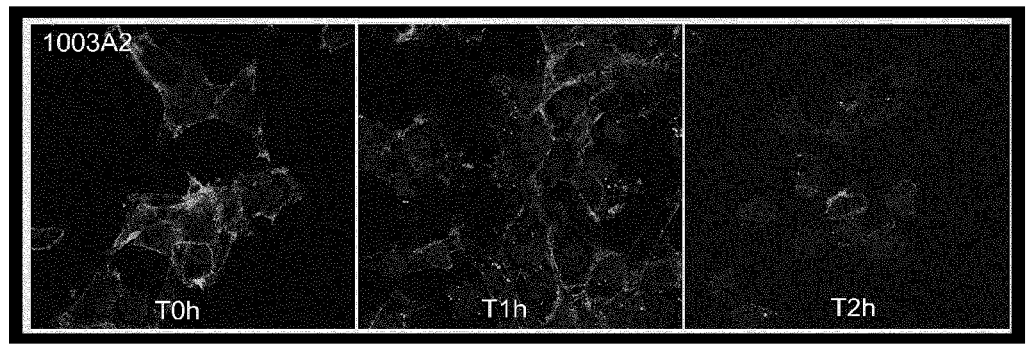
Figure 9F:
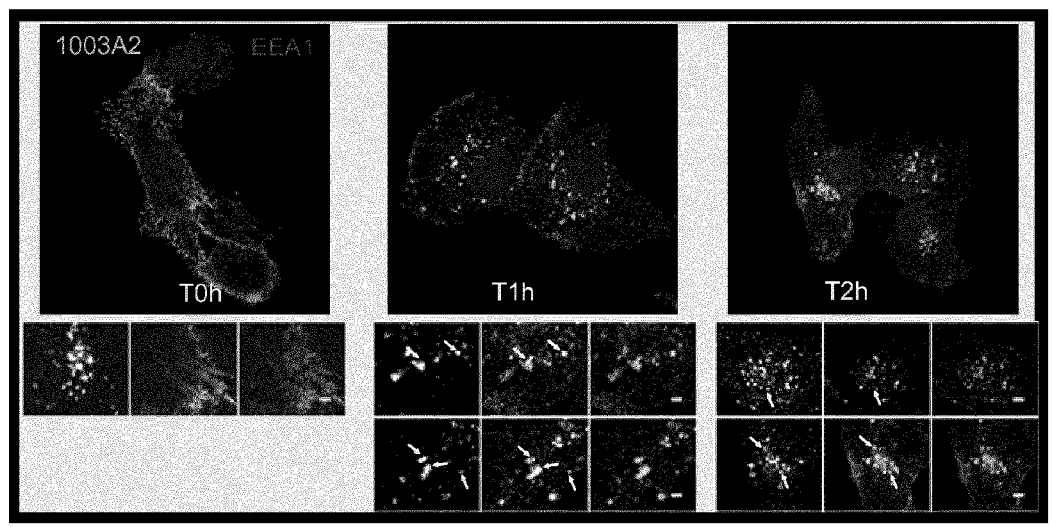
Figure 9G:
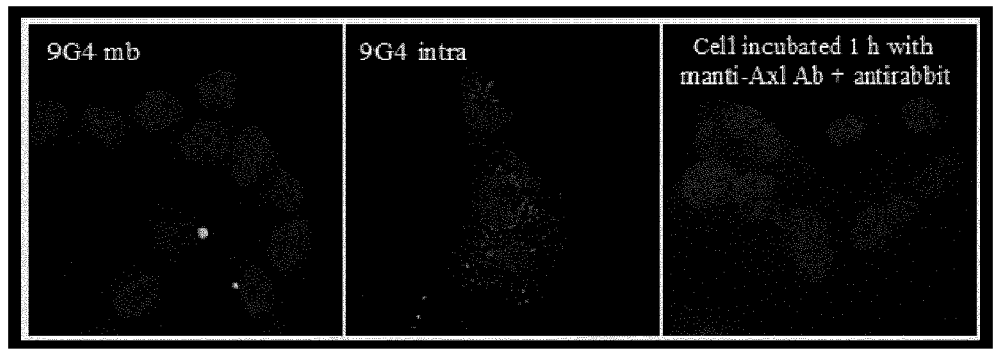
Figure 9H:
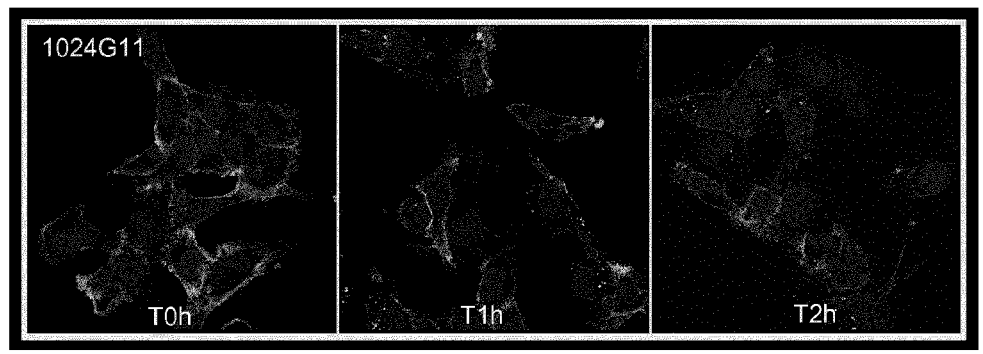
Figure 9I:
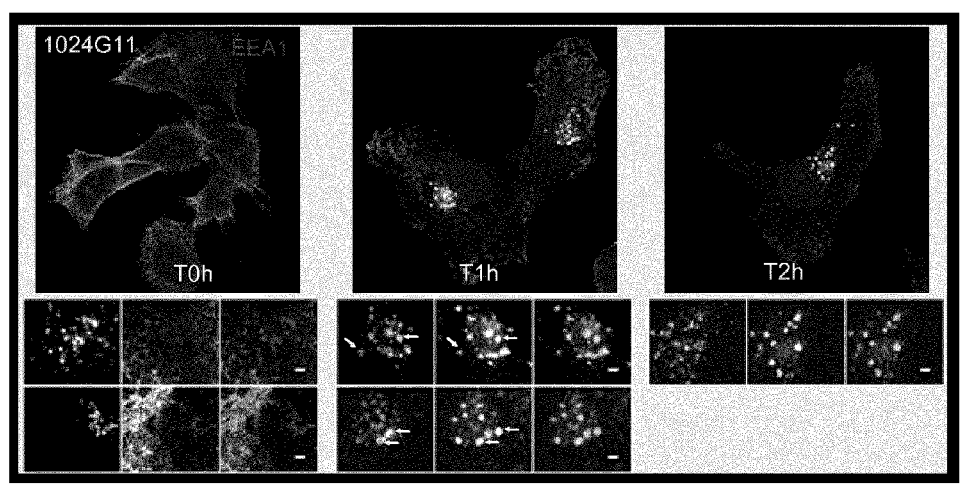

Images were obtained by confocal microscopy. In presence of the mIgG1 isotype control, neither membrane staining nor intracellular labelling is observed (FIGS. 9A, 9D, 9G). A progressive loss of the membrane anti-Axl labeling is observed as soon as after 1 h incubation of the SN12C cells with the 110D7 (FIG. 9B), respectively 1003A2 (FIG. 9E) and 1024G11 (FIG. 9H). Intracellular accumulation of the 110D7 (FIG. 9C), respectively 1003A2 (FIG. 9F) and 1024G11 (FIG. 9I) anti-Axl antibody is more pronounced at 2 h. Intracellular antibody co-localizes with EEA1, an early endosome marker. These photographs confirm the internalization of the anti-Axl mAbs 110D7, 1003A2 and 1024G11 into SN12C cells.

Example 11

In Vitro Anti-Axl Mediated Anti-Tumoral Activity

SN12C Proliferation Assay

Ten thousand SN12C cells per well were seeded in FCS-free medium on 96 well plates over night at 37° C. in a 5% CO$_2$ atmosphere. The next day, cells were pre-incubated with 10 µg/ml of each antibody for 1 h at 37° C. Cells were treated with or without rmGas6 (R and D Systems, cat N° 986-GS/CF), by adding the ligand directly to the well, and then left to grown for 72 h. Proliferation was measured following $^3$H thymidine incorporation.

Data are presented in FIGS. 10A (110D7), 10B (1003A2) and 10C (1024G11). No effect was observed with the 110D7, respectively 1003A2 and 1024G11, which is silent when added to SN12C cells.

Example 12

Cytotoxicity Potency of m110D7-Saporin, 1003A2-Saporin and 1024G11-Saporin Immunoconjugates in Various Human Tumor Cell Lines In the present example, is documented the cytotoxicity potency of the saporin coupled −110D7, −1003A2 or −1024G11 antibodies. For this purpose in vitro cytotoxicity assays using a large panel of human tumor cell lines were performed (FIGS. 11A-11K). This humor tumor cell line panel covers various Axl expressions.

Briefly, 5000 cells were seeded in 96 well culture plates in 100 µl of 5% FBS adequate culture medium. After 24 hour incubation in a 5% CO$_2$ atmosphere at 37° C., a range of concentration of the immunoconjugate (mAxl Ab-saporin or m9G4-saporin) is applied to the cells. Culture plates are then incubated at 37° C. in a humidified 5% CO$_2$ incubator for 72 hours.

At D4, the cell viability is assessed using the CellTiter-Glo® Luminescent Cell Viability kit (Promega Corp., Madison, Wis.) that allows determining the number of viable cells in culture based on quantification of the ATP present, an indicator of metabolically active cells. Luminescent emissions are recorded by a luminometer device.

From luminescence output is calculated the percentage of cytotoxicity using the following formula:

$$\% \text{ cytotoxicity} = 100 - [(RLU_{ab\text{-}sap} \times 100)/RLU_{No\ Ab}]$$

The FIGS. 11A-11K shows that the 110D7-saporin, 1003A2-saporin and 1024G11-saporin immunoconjugates triggered cytotoxicity in these different human tumor cell lines. The potency of the resulting cytotoxicity effect depends on the human tumor cell line.

The invention claimed is:

1. An antigen binding protein that binds Axl and that is selected from the group consisting of:
   a) an antibody comprising the three light chain CDRs comprising the sequences SEQ ID NOs. 1, 2 and 3; and the three heavy chain CDRs comprising the sequences SEQ ID NOs. 4 5 and 6;
   b) an antibody comprising the three light chain CDRs comprising the sequences SEQ ID NOs. 36, 37 and 38; and the three heavy chain CDRs comprising the sequences SEQ ID NOs. 39, 40 and 41; and
   c) an antibody comprising the three light chain CDRs comprising the sequences SEQ ID NOs. 64, 65 and 66; and the three heavy chain CDRs comprising the sequences SEQ ID NOs. 67, 68 and 69;
   or an antigen binding fragment of the antibody of a), b), or c).

2. The antigen binding protein, or any antigen binding fragment thereof, according to claim 1 characterized in that it comprises the three light chain CDRs comprising the sequences SEQ ID NOs. 1, 2 and 3; and a heavy chain variable domain of sequence SEQ ID NO. 8, or any sequence exhibiting at least 80% identity with SEQ ID NO. 8.

3. The antigen binding protein, or any antigen binding fragment thereof, according to claim 1, characterized in that it comprises a light chain variable domain of sequence SEQ ID NO. 7, or any sequence exhibiting at least 80% identity with SEQ ID NO. 7; and the three heavy chain CDRs comprising the sequences SEQ ID NOs. 4, 5 and 6.

4. The antigen binding protein, or any antigen binding fragment thereof, according to claim 1 characterized in that it comprises the three light chain CDRs comprising the sequences SEQ ID NOs. 36, 37 and 38; and a heavy chain variable domain of sequence SEQ ID NO. 43, or any sequence exhibiting at least 80% identity with SEQ ID NO. 43.

5. The antigen binding protein, or an antigen binding fragment thereof, according to claim 1, characterized in that it comprises a light chain variable domain of sequence SEQ ID NO. 42, or any sequence exhibiting at least 80% identity with SEQ ID NO. 42; and the three heavy chain CDRs comprising the sequences SEQ ID NOs. 39, 40 and 41.

6. The antigen binding protein, or an antigen binding fragment thereof, according to claim 1, characterized in that it comprises the three light chain CDRs comprising the sequences SEQ ID NOs. 64, 65 and 66; and a heavy chain variable domain of sequence SEQ ID NO. 71, or any sequence exhibiting at least 80% identity with SEQ ID NO. 71.

7. The antigen binding protein, or an antigen binding fragment thereof, according to claim 1, characterized in that it comprises a light chain variable domain of sequence SEQ ID NO. 70, or any sequence exhibiting at least 80% identity with SEQ ID NO. 70; and the three heavy chain CDRs comprising the sequences SEQ ID NOs. 67, 68 and 69.

8. The antigen binding protein, or an antigen binding fragment thereof, according to claim 1, characterized in that it comprises a light chain variable domain of sequence SEQ ID NO. 7 or any sequence exhibiting at least 80% identity with SEQ ID NO. 7; and a heavy chain variable domain of sequence SEQ ID NO. 8 or any sequence exhibiting at least 80% identity with SEQ ID NO. 8.

9. The antigen binding protein, or an antigen binding fragment thereof, according to claim 1, characterized in that it comprises a light chain variable domain of sequence SEQ ID NO. 42, or any sequence exhibiting at least 80% identity with SEQ ID NO. 42 and a heavy chain variable domain of sequence SEQ ID NO. 43, or any sequence exhibiting at least 80% identity with SEQ ID NO. 43.

10. The antigen binding protein, or an antigen binding fragment thereof, according to claim 1, characterized in that it comprises a light chain variable domain of sequence SEQ ID NO. 70, or any sequence exhibiting at least 80% identity with SEQ ID NO. 70 and a heavy chain variable domain of sequence SEQ ID NO. 71, or any sequence exhibiting at least 80% identity with SEQ ID NO. 71.

11. The antigen binding protein according to claim 1, wherein the antigen binding protein is selected from the group consisting of:
   a) the monoclonal antibody 110D7 produced by the hybridoma l-3959 deposited at the CNCM, Institut Pasteur, France, on 2 Apr. 2008, or an antigen binding fragment thereof;
   b) the monoclonal antibody 1003A2 produced by the hybridoma l-4499 deposited at the CNCM, Institut Pasteur, France, on 28 Jul. 2011, or an antigen binding fragment thereof; and
   c) the monoclonal antibody 1024G11 produced by the hybridoma l-4501 deposited at the CNCM, Institut Pasteur, France, on 28 Jul. 2011, or an antigen binding fragment thereof.

12. A murine hybridoma selected from the group consisting of:
   a) the murine hybridoma l-3959 deposited at the CNCM, Institut Pasteur, France, on 2 Apr. 2008;
   b) the murine hybridoma l-4499 deposited at the CNCM, Institut Pasteur, France, on 28 Jul. 2011; and
   c) the murine hybridoma l-4501 deposited at the CNCM, Institut Pasteur, France, on 28 Jul. 2011.

13. An immunoconjugate comprising the antigen binding protein, or an antigen binding fragment thereof, according to claim 1 conjugated to a cytotoxic agent.

14. Pharmaceutical composition comprising the immunoconjugate of claim 13 and at least an excipient and/or a pharmaceutical acceptable vehicle.

* * * * *